(12) United States Patent
Beernink et al.

(10) Patent No.: US 10,905,754 B2
(45) Date of Patent: Feb. 2, 2021

(54) FACTOR H BINDING PROTEINS (FHBP) WITH ALTERED PROPERTIES AND METHODS OF USE THEREOF

(71) Applicant: CHILDREN'S HOSPITAL & RESEARCH CENTER AT OAKLAND, Oakland, CA (US)

(72) Inventors: Peter T. Beernink, Walnut Creek, CA (US); Dan M. Granoff, San Francisco, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 0 days.

(21) Appl. No.: 16/417,308

(22) Filed: May 20, 2019

(65) Prior Publication Data
US 2020/0000907 A1  Jan. 2, 2020

Related U.S. Application Data

(60) Division of application No. 15/792,519, filed on Oct. 24, 2017, now Pat. No. 10,342,860, which is a continuation of application No. 13/074,957, filed on Mar. 29, 2011, now Pat. No. 9,827,300.

(60) Provisional application No. 61/440,227, filed on Feb. 7, 2011, provisional application No. 61/423,757, filed on Dec. 16, 2010, provisional application No. 61/381,025, filed on Sep. 8, 2010, provisional application No. 61/334,542, filed on May 13, 2010, provisional application No. 61/319,181, filed on Mar. 30, 2010.

(51) Int. Cl.
*A61K 39/05* (2006.01)
*C07K 14/22* (2006.01)
*A61K 39/00* (2006.01)
*A61K 39/095* (2006.01)

(52) U.S. Cl.
CPC ............ *A61K 39/095* (2013.01); *C07K 14/22* (2013.01); *A61K 2039/55505* (2013.01); *A61K 2039/55566* (2013.01)

(58) Field of Classification Search
CPC ........ A61K 39/095; A61K 2039/55505; A61K 2039/55566; A61K 2039/575; A61K 2039/523; A61K 2039/55511; A61K 2039/70; A61K 2039/53; C07K 14/22; C07K 2319/33
See application file for complete search history.

(56) References Cited

U.S. PATENT DOCUMENTS

| 7,628,995 | B2 | 12/2009 | Bos et al. |
|---|---|---|---|
| 8,101,194 | B2 | 1/2012 | Zlotnick et al. |
| 8,470,340 | B2 | 6/2013 | Beernink et al. |
| 8,968,748 | B2 | 3/2015 | Granoff et al. |
| 9,266,942 | B2 | 2/2016 | Granoff et al. |
| 9,827,300 | B2 | 11/2017 | Beernink et al. |
| 10,266,572 | B2 | 4/2019 | Beernink et al. |
| 2004/0167068 | A1 | 8/2004 | Zlotnick et al. |
| 2006/0171957 | A1 | 8/2006 | Pizza et al. |
| 2006/0251670 | A1 | 11/2006 | Comanducci et al. |
| 2006/0257413 | A1 | 11/2006 | Zlotnick et al. |
| 2007/0026021 | A1 | 2/2007 | Fraser et al. |
| 2008/0248065 | A1 | 10/2008 | Granoff et al. |
| 2009/0035328 | A1 | 2/2009 | Granoff et al. |
| 2011/0256180 | A1 | 10/2011 | Beernink et al. |
| 2011/0318378 | A1 | 12/2011 | Beernink et al. |
| 2012/0052092 | A1 | 3/2012 | Exley et al. |
| 2012/0107339 | A1 | 5/2012 | Granfoff et al. |
| 2012/0288517 | A1 | 11/2012 | Beernink et al. |
| 2013/0022633 | A1 | 1/2013 | Banci et al. |
| 2013/0149326 | A1 | 6/2013 | Contorni et al. |
| 2013/0217859 | A1 | 8/2013 | Masignani et al. |
| 2014/0294886 | A1 | 10/2014 | Pizza |

FOREIGN PATENT DOCUMENTS

| AU | 2013206190 | 6/2013 |
|---|---|---|
| WO | WO 1999057280 | 11/1999 |
| WO | WO 2001052885 | 7/2001 |
| WO | WO 2003063766 | 8/2003 |
| WO | WO 2004048404 | 10/2004 |
| WO | WO 2005102384 | 11/2005 |
| WO | WO 2006024954 | 3/2006 |
| WO | WO 2006081259 | 8/2006 |
| WO | WO 2007060548 | 5/2007 |
| WO | WO 2009038889 | 3/2009 |
| WO | WO 2009104097 | 8/2009 |
| WO | WO 2009114485 | 9/2009 |
| WO | WO 2010027872 | 3/2010 |
| WO | WO 2010028096 | 3/2010 |
| WO | WO 2010028859 | 3/2010 |
| WO | WO 2010046715 | 4/2010 |
| WO | WO 2010127172 | 11/2010 |
| WO | WO 2011051893 | 5/2011 |
| WO | WO 2013006055 | 1/2013 |
| WO | WO 2013078223 | 5/2013 |
| WO | WO 2016008960 | 1/2016 |

OTHER PUBLICATIONS

Beernink et al (2010) "Impaired immunogenicity of a meningococcal factor H-binding protein vaccine engineered to eliminate factor h binding" Clin Vaccine Immunol 17(7):1074-1078.
Beernink et al. (2011) "A Meningococcal Factor H Binding Protein Mutant That E

(56) References Cited

OTHER PUBLICATIONS

Beernink et al. In: Program and Abstract Guide, 17th International Pathogenic Neisseria Conference, Banff, Alberta, Canada, p. 58, #OM42, Sep. 11-16, 2010.

Beernink, et al (2006) "Rapid Genetic Grouping of Factor h-binding Protein (Genome-Derived neisserial antigen 1870), a Promising Group B Meningoccal Vaccine Candidate", *Clin. Vaccine Immunol.* 13(7):758-763.

Beernink, et al., "A Region of the N-Terminal Domain of Meningococcal Factor H-Binding Protein that Elicits Bactericidal Antibody Across Antigenic Variant Groups", Molecular Immunology, 2009, 46(8-9):1647-1653.

Beernink, et al., "Fine Antigenic Specificity and Cooperative Bactericidal Activity of Monoclonal Antibodies Directed at the Meningococcal Vaccine Candidate Factor H-Binding Protein", Infection and Immunity, 2008, 76(9):4232-4940.

Beernink, et al., "Prevalence of Factor H-Binding Protein Variants and NadA Among Meningococcal Group B Isolates from the United States: Implications for the Development of a Multicomponent Group B Vaccine", Journal of Infectious Disease, 2007, 195(10):1472-1479.

Beernink, et al., The Modular Architecture of Meningococcal Factor H-Binging Protein, Microbiology, 2009, 155:2873-2883.

Beernink, et al., Factor H Binding Protein. GenBank Direct Submission Accession ACJ45782 [online]. Nov. 23, 2009 [retrieved on Aug. 2, 2011], retrieved from the Internet:URL:http://www.ncbi.nlm.nih.gov/proteinacj45782, p. 1.

Beernink. et al., "Bactericidal Antibody Responses Induced by Meningococcal Recombinant Chimeric Factor H-Binding Protein Vaccines", Infection and Immunity, 2008, 76(6):2568-2575.

Borrow et al., "Serological Basis for Use of Meningococcal Serogroup C Conjugate Vaccines in the United Kingdom: Reevaluation of Correlates of Protection", Infect. Immun. (2001) 69(3):1568-1573.

Davila et al. (2010) "Genome-wide association study identifies variants in the CFH region associated with host susceptibility to meningococcal disease" *Nat Genetics* 42(9):772-776. doi:10.1038/ng.640.

De Filippis, et al., Factor H Binding Protein. Gen Bank Direct Submission Accession ACZ93150 [online]. Dec. 15, 2009 [retrieved on Aug. 2, 2011], retrieved from the internet:URL:http://www.ncbi.nlm.nih.gov/protein/acz93150,p. 1.

De Filippis, et al., Factor H Binding Protein. GenBank Direct Submission Accession ACZ93290 [online]. Dec. 15, 2009] retrieved on Aug. 2, 2011, retrieved from the Internet:URL:http://www.ncbi.nlm.nih.gov/protein/acz93290, p. 1.

Dunphy, et al., "Effect of Factor H-Binding Protein Sequence Variation on Factor H Binding and Survival of *Neisseria meningitidis* in Human Blood", 2011, Infection and Immunity, vol. 79, No. 1, pp. 353-359.

Fletcher, et al. (2004) "Vaccine potential of the Neisseria meningitidis 2086 lipoprotein" *Infect Immun.* 72(4):2088-2100.

Fukasawa, et al., Immune Response to Naitive NadA from Neisseria Meningitidis and its Expression in Clinical Isolates in Mrazil, Journal of Medical Microbiology, 2003, 52:121-125.

Genbank Accession No. AAW88802, Factor H binding protein from *Neisseria gonorrhoeae* (strain ATCC 700825/FA 1090) Mar. 15, 2005.

GenBank Accession No. AY548370 "Neisseria meningitidis strain H44/76 lipoprotein (gna1870) gene, complete cds" (AAT01289.1) (from N. meningitidis strain H44/76), dated May 1, 2004.

GenBank Accession No. AY548371 "Neisseria meningitidis strain CU385 lipoprotein (gna1870) gene, complete cd" (AAT01290.1) (from N. meningitidis strain CU385), dated May 1, 2004.

GenBank Accession No. AY548372 "Neisseria meningitidis strain BZ83 lipoprotein GNA1870 (gna1870) gene, complete cd" (AAS56915.1) (from N. meningitidis strain BZ83), dated Apr. 22, 2004.

GenBank Accession No. AY548373 "Neisseria meningitidis strain 4243 lipoprotein GNA1870 (gna1870) gene, complete cd" (AAS56916.1) (from N. meningitidis strain 4243), dated Apr. 22, 2004.

GenBank Accession No. AY548374 "Neisseria meningitidis strain M6190 lipoprotein GNA1870 (gna1870) gene, complete cd" (AAS56917.1) (from N. meningitidis strain M6190), dated Apr. 22, 2004.

GenBank Accession No. AY548375 "Neisseria meningitidis strain N98/254 lipoprotein GNA1870 (gna1870) gene, complete cd" (AAS56918.1) (from N. meningitidis strain NZ98/254), dated Apr. 22, 2004.

GenBank Accession No. AY548376 "Neisseria meningitidis strain M1390 lipoprotein GNA1870 (gna1870) gene, complete cds" (AAS56919.1) (from N. meningitidis strain M1390), dated Apr. 22, 2004.

GenBank Accession No. AY548377 "Neisseria meningitidis strain M4105 lipoprotein GNA1870 (gna1870) gene, complete cd" (AAS56920.1) (fHbp ID 4 from N. meningitidis strain M4105), dated Apr. 22, 2004.

GenBank Accession No. NC_003112, "Neisseria meningitidis MC58, complete genom" GeneID: 904318 (NCBI Ref. NP_274866), fHbp ID 1 from N. meningitidis strain MC58, ), dated May 24, 2010.

GenBank Accession No. NP_000177 (P08603), and its encoding nucleic acid as NM_000186, "complement factor H isoform a precursor [*Homo sapiens*]" dated Mar. 21, 2010.

Giuliani, et al. (2005) "The region comprising amino acids 100 to 255 of Neisseria meningitidis lipoprotein GNA 1870 elicits bactericidal antibodies" *Infect. Immun.* 73(2):1151-1160.

Goldschneider, et al. (1969) "Human Immunity to the Meningococcus: I. The Role of the Humoral Antibodies" *J. Exp. Med.* 129(6):1307-1326.

Granoff, et al. (1998) "Bacterial Monoclonal Antibodies That Define Unique Meningococcal B Polysaccharide Epitopes That Do Not Cross-React with Human Polysialic Acid" *J. Immunol.* 160(10):5028-5036.

Granoff, et al. (2009) "Binding of complement factor H (fH) to Neisseria meningitidis is specific for human fH and inhibits complement activation by rat and rabbit sera" *Infect. Immun.* 77(2):764-769.

Huo et al. (2005) "Protective antibody responses elicited by a meningococcal outer membrane vesicle vaccine with overexpressed genome-derived neisserial antigen 1870" Journal of Infectious Diseases; 192(4):580-590.

Johnson S. et al., "Design and Evaluation of Meningococcal Vaccines through Structure-Based Modification of Host and Pathogen Molecules", PLOS Pathogens (2012) 8(10): e1002981.

Konar et al. (2015) "A Mutant Library Approach to Identify Improved Meningococcal Factor H Binding Protein Vaccine Antigens" PLoS One. 10(6):e0128185.

Lazar et al. (1988) "Transforming Growth Factor alpha: Mutation of Aspartic Acid 47 and Leucine 48 Results in Different Biological Activities" Cellular Biol. 8(3):1247-1252.

Lewis, et al., The Meningococcal Vaccine Candidate Neisserial Surface Protein A (NspA) Binds to Factor H and Enhances Meningococcal Resistance to Complement, PLOS Pathogens, 2010, 6(7):1-20.

Madico, et al., "The Meningococcal Vaccine Candidate GNA1870 Binds the Complement Regulatory Protein Factor H and Enhances Serum Resistance", 2006, The Journal of Immunology, 177:501-510.

Madico, et al., Factor H Binding Protein. GenBank Direct Submission Accession ABC59063 [online], Jun. 20, 2006 [retrieved on Aug. 2, 2011], retrieved from the Internet:URL:http://www.ncbi.nlm.nih.gov/protein/abc59063, p. 1.

Mascioni et al. (2009) "Structural Basis for the Immunogenic Properties of the Meningococcal Vaccine Candidate LP2086" Journal of Bio. Chem.; 284(13):8738-8746.

Masignani, et al., "Vaccination against Neisseria meningitides Using Three Variants of the Lipoprotein GNA1879," Journal Exp. Med., 2003, 197(6):789-799.

Maslanka, et al., "Standardization and a Multilaboratory Comparison of Neisseria Meningitidis Serogroup A and C Serum Bactericidal Assays", Clinical Diagnostic Laboratory Immunology, 1997, 4(2):156-157.

McDowell, et al., "Demonstration of the Involvement of Outer Surface Protein E Coiled Coil Structure and Higher Order Structural Elements in the Binding of Infection-Induced Antibody and the

(56) References Cited

OTHER PUBLICATIONS

Complement-Regulatory Protein, Factor H", Journal of Immunology, 2004, vol. 173, pp. 7471-7480.

Morrison, K.L., et al., "Combination alanine-scanning," Curr. Opin. Chem. Biol. (2001) 5:302.307.

Murphy, et al., Factor H Binding Protein Variant A72_001. GenBank Direct Submission Accession ACI46937 [online]. Aug. 4, 2009 [retrieved from the internet]:URL:http://www.ncbi.nim.nih.gov/protein/aci46937, p. 1.

Murphy, et al., "Sequence Diversity of the Factor H Binding Protein Vaccine Candidate in Epidemiologically Relevant Strains of Serogroup B Neisseria meningitidis", The Journal of Infectious Diseases, 2009, pp. 379-389.

Ngampasutadol et al., "A Novel Interaction Between Factor H SCR 6 and the Meningococcal Vaccine Candidate GNA 1870: Implications for Meningococcal Pathogenesis and Vaccine Development", Molecular Immunology, 2007, 44(1-3):220.

Ngampasutadol et al., "Human Factor H Interacts Selectively with Neisseria Gonorrhoeae and Results in Species-Specific Complement Evasion", The Journal of Immunology, 2008, 180(5):3426-3435.

Pajon, et al. "Design of meningococcal factor H binding protein mutant vaccines that do not bind human complement factor H", Infect Immun. (2012) 80(8):2667-77.
Pajon, et al. (2010) "Frequency of factor H-binding protein modular groups and susceptibility to cross-reactive bactericidal activity in invasive meningococcal isolates" *Vaccine* 28(9):2122-2129.
Scarselli, et al. (2009) "Epitope mapping of a bactericidal monoclonal antibody against the factor H binding protein of Neisseria meningitidis" *J. Mol. Biol.* 386(1):97-108.
Schneider, et al. "Supplemental Methods for Neisseria Meningitides Recruits Factor H Using Protein Mimicry of Host Carbohydrates", Nature, 2009, 1-17.
Schneider, et al. "Neisseria Meningitides Recruits Factor H Using Protein Mimicry of Host Carbohydrates", Nature, 2009, 458:890-895.
Seib, et al., "Characterization of Diverse Subvariants of the Meningococcal Factor H (fH) Binding Protein for Their Ability to Bind fH, to Mediate Serum Resistance, and to Induce Bactericidal Antibodies", 2011, Infection and Immunity, vol. 79, No. 2, pp. 970-981.
Shaughnessy, et al. (2009) "Functional comparison of the binding of factor H short consensus repeat 6 (SCR 6) to factor H binding protein from Neisseria meningitidis and the binding of factor H SCR 18 to 20 to Neisseria gonorrhoeae porin" *Infect. Immun.* 77(5):2094-2103.
Skolnick et al. (2000) "From genes to protein structure and function: novel applications of computational approaches in the genomic era" Trends in Biotechnology. 18:34-39.
Tettelin, et al., Uniprot Q9JXV4 [online] Oct. 1, 2000 [retrieved on Aug. 2, 2011], retrieved from the internet: URL:http://www.uniprot.org/uniprot/Q9JXV4.txt, p. 1.
Vu et al., "A Broadly Cross-Reactive Monoclonal Antibody Against an Epitope on the N-terminus of Meningococcal fHbp",Scientic Reports (2012) 2(341):1-8.
Welsch, et al., Complement-Dependent Synergistic Bactericidal Activity of Antibodies Against Factor H-Binding Protein, a Sparsely Distributed Meningococcal Vaccine Antigen, The Journal of Infectious Disease, 2008, 197:1053-61.
Welsch, et al., "Protective Activity of Monoclonal Antibodies to Genome-Derived Neisserial Antigen 1870, a Neisseria Meningitidis Candidate Vaccine", Journal of Immunology, 2004, 172:5606-5615.
Welsch, et al., Lipoprotein GNA1870. GenBank Direct Submission Accession AAS56918 [online], Apr. 22, 2004 [retrieved on Aug. 2, 2011], retrieved from the Internet:<URL:http://www.ncbi.nlm.nih.gov/protein/AAS56918, p. 1.

fH, JAR4, and JAR5 binding to fHbp ID 1 wildtype and mutants

```
MRLLAKIICLMLWAICVAEDCNELPPRRNTEILTGSWSDQTYPEGTQAIYKCRPGYRSLG    60
NVIMVCRKGEWVALNPLRKCQKRPCGHPGDTPFGTFTLTGGNVFEYGVKAVYTCNEGYQL   120
LGEINYRECDTDGWTNDIPICEVVKCLPVTAPENGKIVSSAMEPDREYHFGQAVRFVCNS   180
GYKIEGDEEMHCSDDGFWSKEKPKCVEISCKSPDVINGSPISQKIIYKENERFQYKCNMG   240
YEYSERGDAVCTESGWRPLPSCEEKSCDNPYIPNGDYSPLRIKHRTGDEITYQCRNGFYP   300
ATRGNTAKCTSTGWIPAPRCTLKPCDYPDIKHGGLYHENMRRPYFPVAVGKYYSYYCDEH   360
FETPSGSYWDHIHCTQDGWSPAVPCLRKCYFPYLENGYNQNYGRKFVQGKSIDVACHPGY   420
ALPKAQTTVTCMENGWSPTPRCIRVKTCSKSSIDIENGFISESQYTYALKEKAKYQCKLG   480
YVTADGETSGSITCGKDGWSAQPTCIKSCDIPVFMNARTKNDFTWFKLNDTLDYECHDGY   540
ESNTGSTTGSIVCGYNGWSDLPICYERECELPKIDVHLVPDRKKDQYKVGEVLKFSCKPG   600
FTIVGPNSVQCYHFGLSPDLPICKEQVQSCGPPPELLNGNVKEKTKEEYGHSEVVEYYCN   660
PRFLMKGPNKIQCVDGEWTTLPVCIVEESTCGDIPELEHGWAQLSSPPYYYGDSVEFNCS   720
ESFTMIGHRSITCIHGVWTQLPQCVAIDKLKKCKSSNLIILEEHLKNKKEFDHNSNIRYR   780
CRGKEGWIHTVCINGRWDPEVNCSMAQIQLCPPPPQIPNSHNMTTTLNYRDGEKVSVLCQ   840
ENYLIQEGEEITCKDGRWQSIPLCVEKIPCSQPPQIEHGTINSSRSSQESYAHGTKLSYT   900
CEGGFRISEENETTCYMGKWSSPPQCEGLPCKSPPEISHGVVAHMSDSYQYGEEVTYKCF   960
EGFGIDGPAIAKCLGEKWSHPPSCIKTDCLSLPSFENAIPMGEKKDVYKAGEQVTYTCAT  1020
YYKMDGASNVTCINSRWTGRPTCRDTSCVNPPTVQNAYIVSRQMSKYPSGERVRYQCRSP  1080
YEMFGDEEVMCLNGNWTEPPQCKDSTGKCGPPPPIDNGDITSFPLSVYAPASSVEYQCQN  1140
LYQLEGNKRITCRNGQWSEPPKCLHPCVISREIMENYNIALRWTAKQKLYSRTGESVEFV  1200
CKRGYRLSSRSHTLRTTCWDGKLEYPTCAKR  1231 (SEQ ID NO:9)
```

FIG. 9B

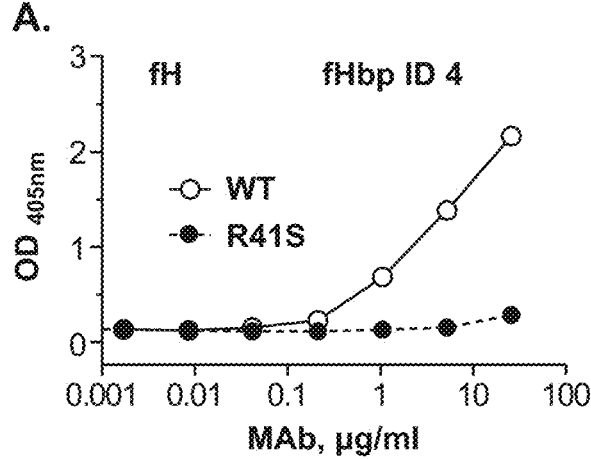
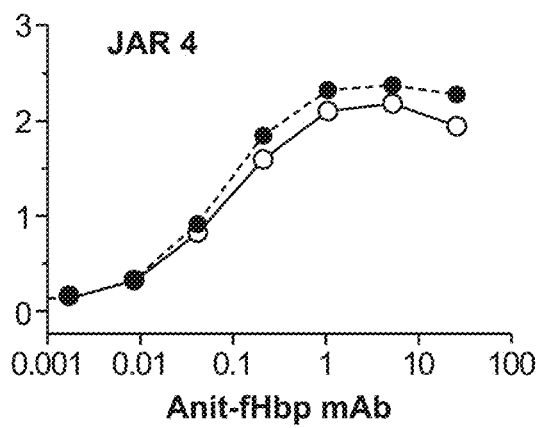
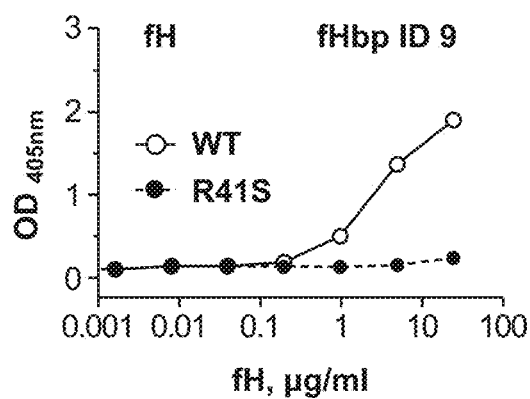
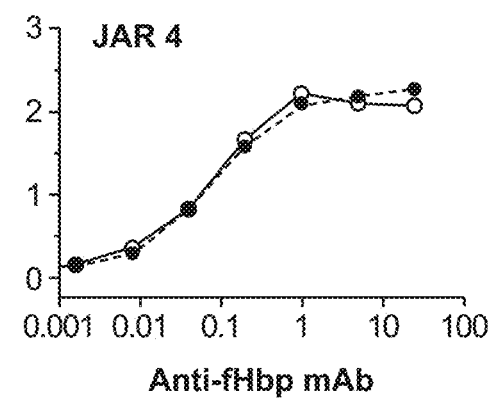
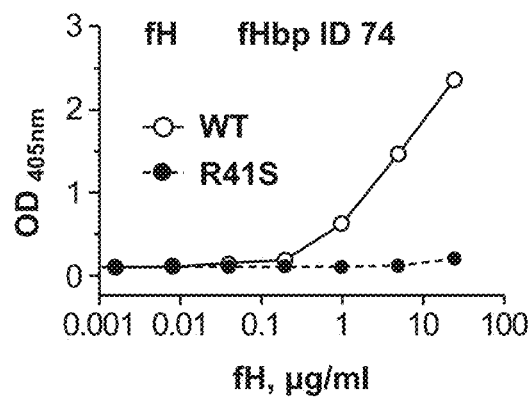
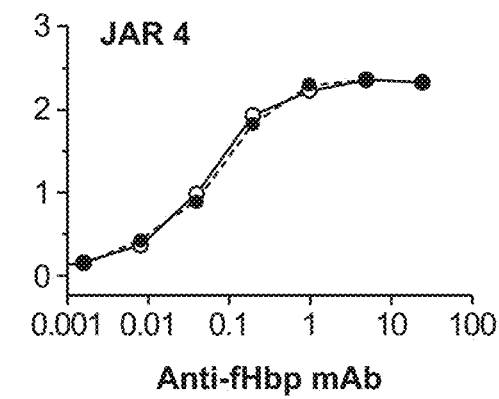
FIG. 11 fH and JAR5 binding to fHbp ID 1 wildtype and mutant fH and JAR5 binding to fHbp ID 15 wildtype and mutant

| Modular Group | Variant Group | Modular Segment $V_A$ | $V_B$ | $V_C$ | $V_D$ | $V_E$ | No. |
|---|---|---|---|---|---|---|---|
| I | 1 | ▓▓▓ | △ | ◯ | ◇ | ▓▓▓ | 33 |
| II | 3 | ☐ | △ | ◯ | ◇ | ☐ | 7 |
| III | 2 | ▓▓▓ | △ | ◯ | ◇ | ☐ | 5 |
| IV | 1 | ☐ | △ | ◯ | ◇ | ▓▓▓ | 5 |
| V | 3 | ☐ | △ | ◯ | ◇ | ☐ | 10 |
| VI | 2 | ▓▓▓ | △ | ◯ | ◇ | ☐ | 10 |
| Chimera | 1/2 | ▓▓▓ | △ | ◯ | ◇ | ☐ | |

FIG. 16

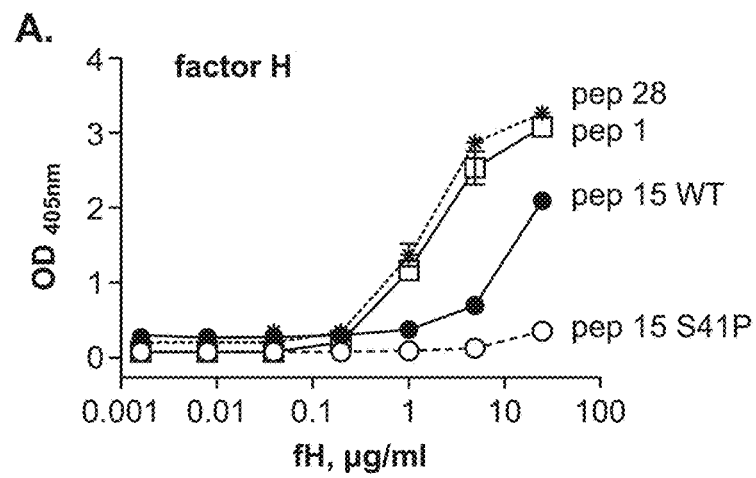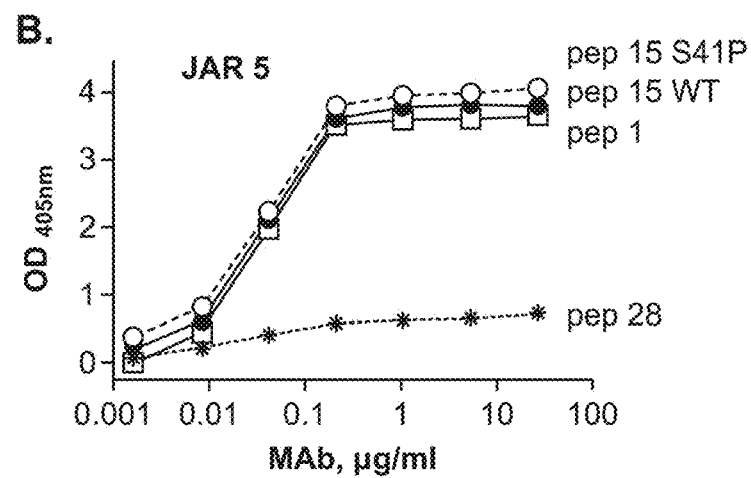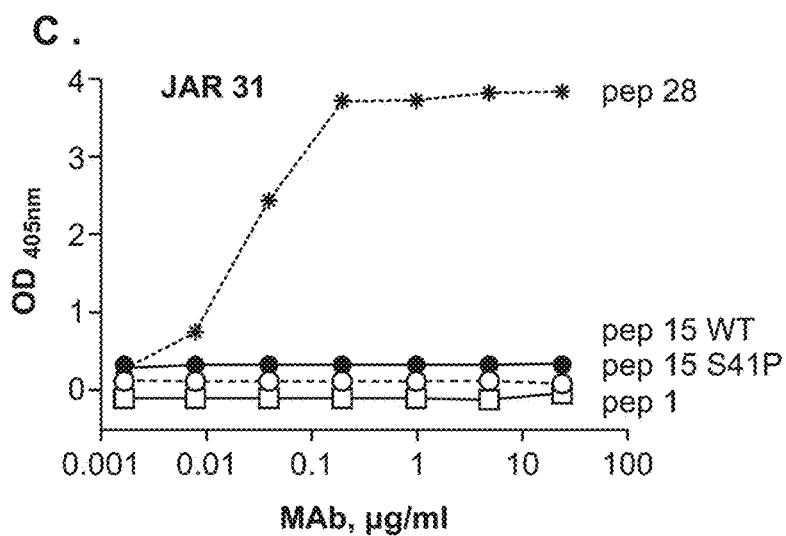
FIG. 17

```
ID15      CSSGGGGSGGGGVAADIGAGLADADALTAPLDHEDKGLKSLTTLESSTHQMGTLTLSAQGAEK
ID1       CSSGGGG------VAADIGAGLADADALTAPLDHKDKGLKSLTTLESSTHQMGTLTLSAQGAEK
Chimera   CSSGGGG------VAADIGAGLADADALTAPLDHKDKGLQSLTLDQSVRKMEKLKLAAGGAEK
ID77      CSSGGGG------VAADIGARLADALTAPLDHKDKGLQSLTLDQSVRKNEKLKLAAQGAEK
ID28      CSSGGGGSGGGGVAADIGTGLADADALTAPLDHKDKGLKSLTFLEDSTPQNGTLTLSAQGAEK
ID22      CSSGGGG------VAADIGAGLADADALTAPLDHKDKSLQSLTLDQSVRKMEKLKLAAQGAEK ID15      TFKAGDKDNSLNTGKLKNDKISREDFIRQIEVDGQLITLESGEFQVYKQSHSALTALQTE
ID1       TYGNGD----SLNTGKLKNDKVSRFDFTRQIEVDGQLITLESGEFQVYKQSHSALTAFQTE
Chimera   TYGNGD----SLNTGKLKNDKVSRFDFTRQIEVDGQLITLESGEFQVYKQSHSALTAFQTE
ID77      TYGNGD----SLNTGKLKNDKVSRFDFTRQIEVDGQLITLESGEFQIYKQDHSAVVALQIE
ID28      TFKAGDKDNSLNTGKLKNDKISREDFVQKIEVDGQITLASGEFQIYKQMHSAVVALQIE
ID22      TYGNGD----SLNTGKLKNDKVSRFDFTRQIEVDGQLITLESGEFQIYKQDHSAVVALQIE ID15      QVQDSEHSGKMVAKRQFRIGDIVGEHTSTGKLPKATYRGTAFGSDDAGGKLTYTIDF
ID1       QIQDSEHSGKMVAKRQFRIGDIAGEHTSFDKLPEGGRATYRGTAFGSDDAGGKLTYTIDF
Chimera   QIQDSEHSGKMVAKRQFRIGDIAGEHTAFMQLP--DGKAEYHGKAFSSDDAGGKLTYTIDF
ID77      KINNPDKIDSLINQRSFLVSGLGGEHTAFMQLP--DGKAEYHGKAFSSDDAGGKLTYTIDF
ID28      KINNPDKTDSLTNQRSFLVSGLGGEHTAFMQLP--GGKAEYHGKAFSSDDPMGRLHYSIDF
ID22      KINNPDKIDSLINQRSFLVSGLGGEHTAFMQLP--SGKAEYHGKAFSSDDPMGRLHYSIDF ID15      AAKQGMGKIEHLKSPELNVDLAAADIKPDEKHHAVISGSVLYNQEKGSYSLGIFGGQAQ
ID1       AAKQGNGKIEHLKSPELMVDLAAADIKPDGKRHAVISGSVLYNQEKGSYSLGIFGGKAQ
Chimera   AAKQGHGKIEHLKTPEQWVELAAAELKADEKSHAVILGDTRYGSHEKGTYHLALFGDRAQ
ID77      AAKQGHGKIEHLKTPEQWVELAAAELKADEKSHAVILGDTRYGSEKGTYHLALFGDRAQ
ID28      TKKQGYGRIERLKTLEQWVELAAAELKADEKSHAVILGDTRYGSEKGTYHLALFGDRAQ
ID22      TKKQGYGRIEHLKTPEQWVELASAELKADEKSHAVILGDTRYGGEKGTYHLALFGDRAQ ID15      EVAGSAEMTVNGIRHIGLAAKQ     263 (SEQ ID NO:5)
ID1       EVAGSAEVKTVNGIRHHIGLAAKQ   255 (SEQ ID NO:1)
Chimera   EIAGSATVKIGEKVHEIGIAGKQ    254 (SEQ ID NO:8)
ID77      EIAGSATVKIGEKVHEIGIAGKQ    254 (SEQ ID NO:4)
ID28      EIAGSATVKIGEKVHEIGIAGNQ    262 (SEQ ID NO:3)
ID22      EIAGSATVKIREKVHEIGIAGKQ    254 (SEQ ID NO:2)
```

FIG. 19A

```
(A1,2)
ID  1        VAADIGAGLA DALTAPLDHK DKGLQSLTLD QSVPRNEKLK LAAQGAENTY GNGD----SLN TGKLKNDKV  (SEQ ID NO:28)
ID 77        VAADIGARLA DALTAPLDHK DKGLQSLTLD QSVPRNEKLK LAAQGAENTY GNGD----SLN TGKLKNDKV  (SEQ ID NO:29)
(A1,5)
```

FIG. 19B

```
ID  1 (C1,5)  VYKQSRSALT AFQTEQIQDS EHSGKMVAKR QFPIGDIAGE RTSFDKLFKG GRATYRGTAF  (SEQ ID NO:30)
ID 77 (C2,4)  VYKQSRSALT ALQTEQVQDS EHSGMVAKR  QFKIGDIV   RTSFGKLFKD VMATYRGTAF  (SEQ ID NO:31)
```

FIG. 19C

| ID | MG | VG | | | |
|---|---|---|---|---|---|
| 1 | I | 1 | TAPLDHKDKG LQSLTLDQSV | RKNEKLKLAAQGAEKTYGNGD----SLNTGKLKN | SEQ ID NO:10 |
| 4 | I | 1 | TAPLDHKDKS LQSLTLDQSV | RKNEKLKLAAQGAEKTYGNGD----SLNTGKLKN | SEQ ID NO:11 |
| 9 | I | 1 | TAPLDHKDKG LQSLTLDQSV | RKNEKLKLAAQGAEKTYGNGD----SLNTGKLKN | SEQ ID NO:10 |
| 74 | I | 1 | TAPLDHKDKS LQSLTLDQSV | RKNEKLKLAAQGAEKTYGNGD----SLNTGKLKN | SEQ ID NO:11 |
| 15 | IV | 1 | TAPLDHKDKG LKSLTLEDSI | SQNGTLTLSAQGAERTFKAGDKDNSLNTGKLKN | SEQ ID NO:12 |
| 55 | IV | 1 | TAPLDHKDKG LKSLTLEDSI | SQNGTLTLSAQGAERTFKAGDKDNSLNTGKLKN | SEQ ID NO:12 |
| 22 | III | 2 | TAPLDHKDKS LQSLTLEDSI | SQNGTLTLSAQGAERTFKAGDKDNSLNTGKLKN | SEQ ID NO:13 |
| 19 | VI | 2 | TAPLDHKDKS LQSLTLDQSV | RKNEKLKLAAQGAEKTYGNGD----SLNTGKLKN | SEQ ID NO:11 |
| 77 | VI | 2 | TAPLDHKDKS LQSLTLDQSV | RKNEKLKLAAQGAEKTYGNGD----SLNTGKLKN | SEQ ID NO:11 |
| 28 | II | 3 | TAPLDHKDKG LKSLTLEDSI | PQNGTLTLSAQGAERTFKAGDKDNSLNTGKLKN | SEQ ID NO:14 |

```
ID 1 (v.1)   CSSGGGG---  ---VAADIGAG  LADALTAPLD  HKDKGLQSLT  LDQSVRKNEK  LKLAAQGAEK   55
ID 77(v.2)   CSSGGGG---  ---VAADIGAR  LADALTAPLD  HKDKGLQSLT  LDQSVRKNEK  LKLAAQGAEK   55
Chimera 1    CSSGGGG---  ---VAADIGAG  LADALTAPLD  HKDKGLQSLT  LDQSVRKNEK  LKLAAQGAEK   55

ID 1         TYGNGD----S  LNTGKLKNDK  VSRFDFIRQI  EVDGQLITLE  SGEFQVYKQS  HSALTAFQTE  112
ID 77        TYGNGD----S  LNTGKLKNDK  VSRFDFIRQI  EVDGQLITLE  SGEFQVYKQ   HSA A  E    112
Chimera      TYGNGD----S  LNTGKLKNDK  VSRFDFIRQI  EVDGQLITLE  SGEFQVYKQS  HSALTAFQTE  112

ID 1         QIQDSEHSGK  MVAKRQFRIG  DIA  GEHT  SFD  KLPEGGRATY  RGTAFGSSDDA  GGKLTYTIDF  172
ID 77                                    GEHT  AFN  QLP-DGKAEY  HGKAFSSDDA   GGKLTYTIDF  171
Chimera      QIQDSEHSGK  MVAKRQFRIG  DIA  GEHT  AFN  QLP-DGKAEY  HGKAFSSDDA   GGKLTYTIDF  171

ID 1         AAKQGNGKIE  HLKSPELNVD  LAAAADIKPDG  KRHAVISGSY  LYNQAERGSY  SLGIFGGKAQ  232
ID 77        AAKQGHGRIE  HLKTPEQNVE  LAAAAELKADE  KSHAVILGDT  RYGSEEKGTY  HLALFGDRAQ  231
Chimera      AAKQGHGKIE  HLKTPEQNVE  LAAAAELKADE  KSHAVILGDT  RYGSEEKGTY  HLALFGDRAQ  231

ID 1         EVAGSAEVKT  VNGIRHIGLA  AKQ  255  (SEQ ID NO:1)
ID 77        EIAGSATVKI  GEKVHEIGIA  GKQ  254  (SEQ ID NO:4)
Chimera      EIAGSATVKI  GEKVHEIGIA  GKQ  254  (SEQ ID NO:8)
```

FIG. 19E

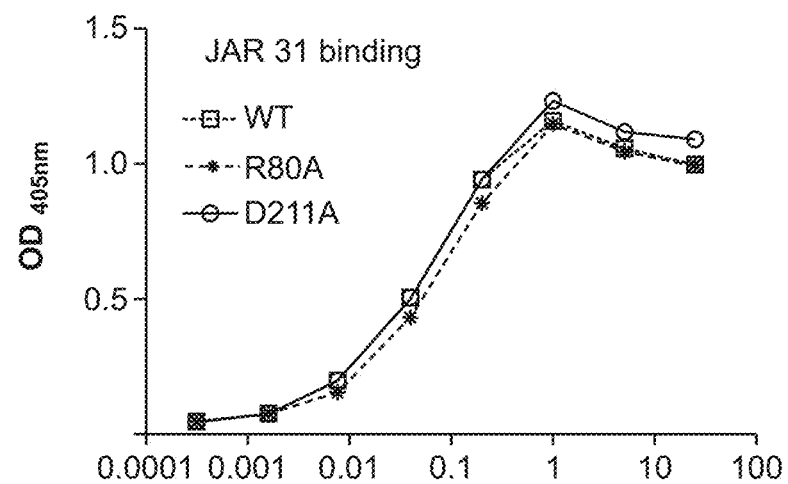
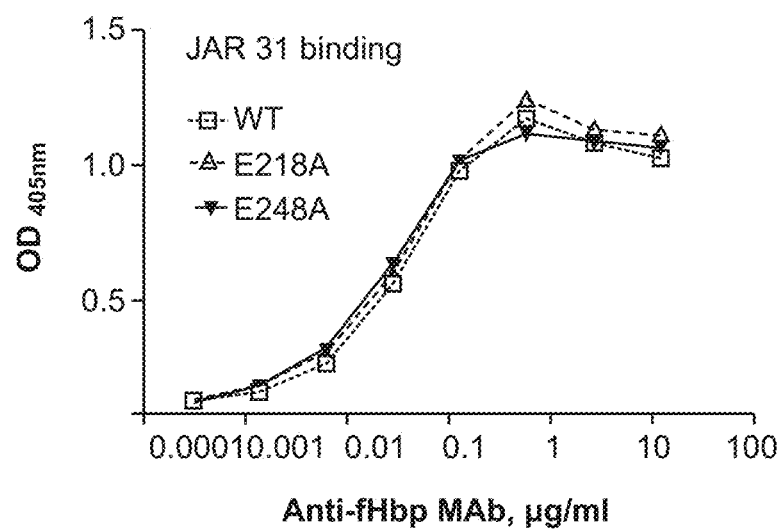
FIG. 24

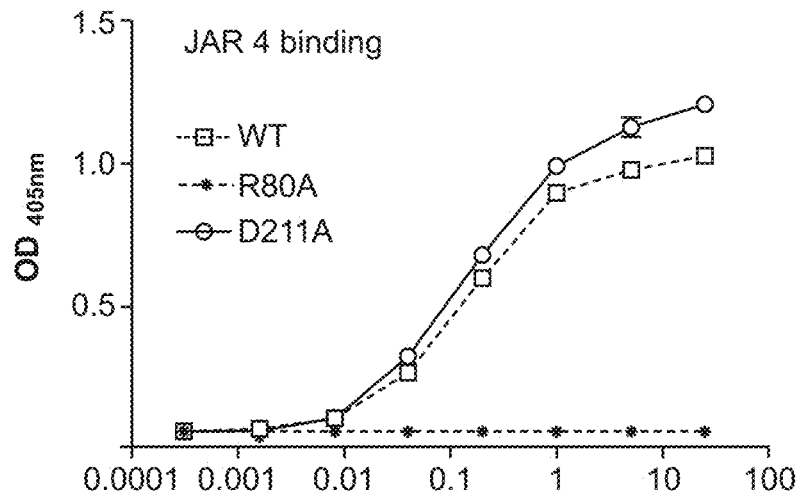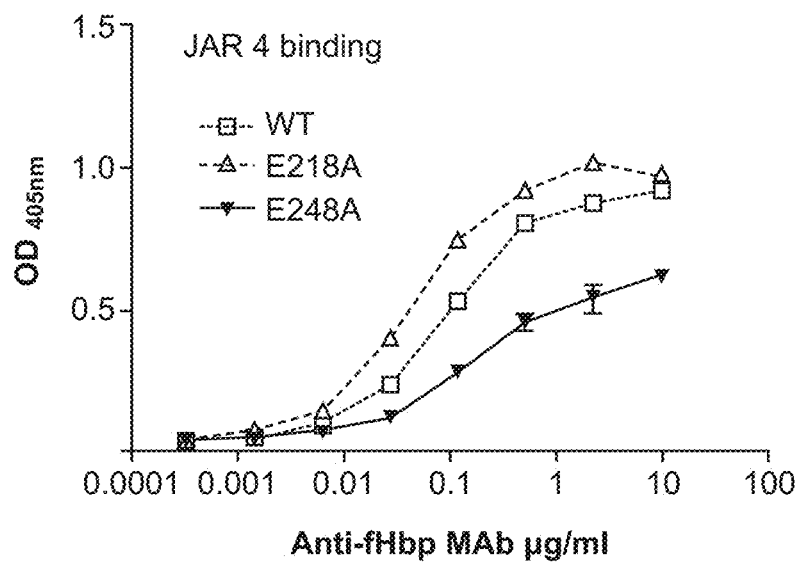
FIG. 25

JAR 35 binding to fHbp ID 22 wildtype and mutants

Panel A

JAR 35 binding
- WT
- R80A
- D211A

Panel B

JAR 35 binding
- WT
- E218A
- E248A

Anti-fHbp MAb µg/ml

FIG. 26

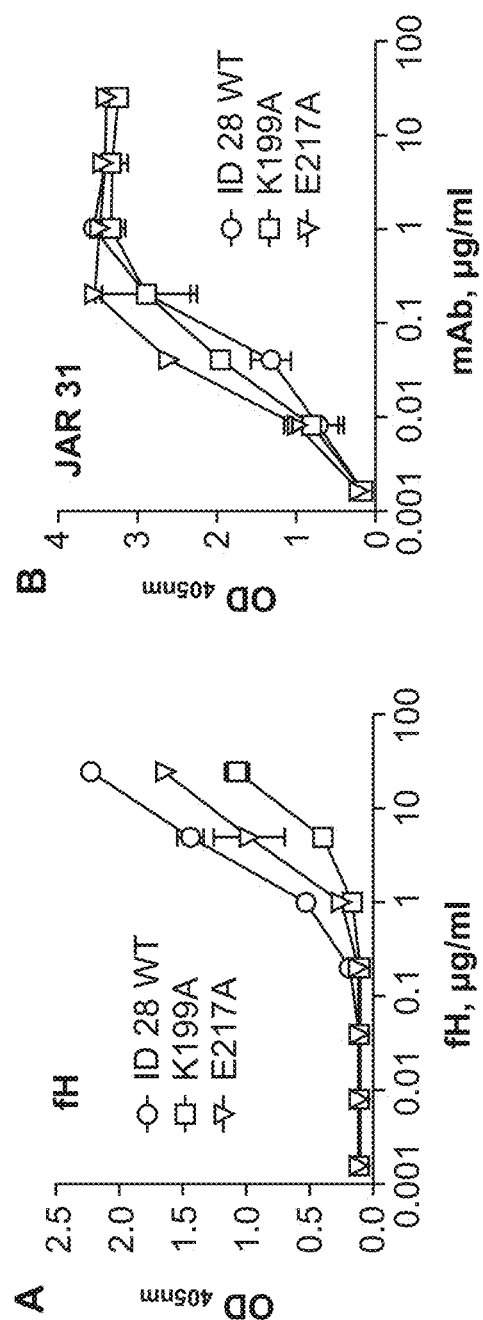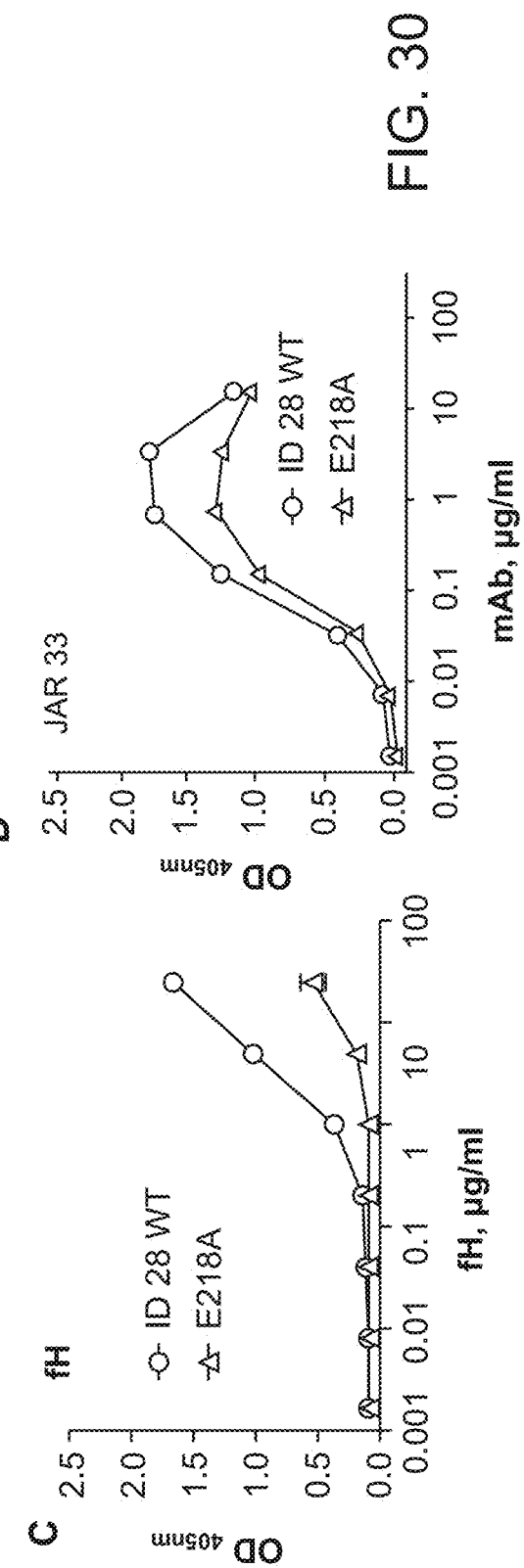
FIG. 30

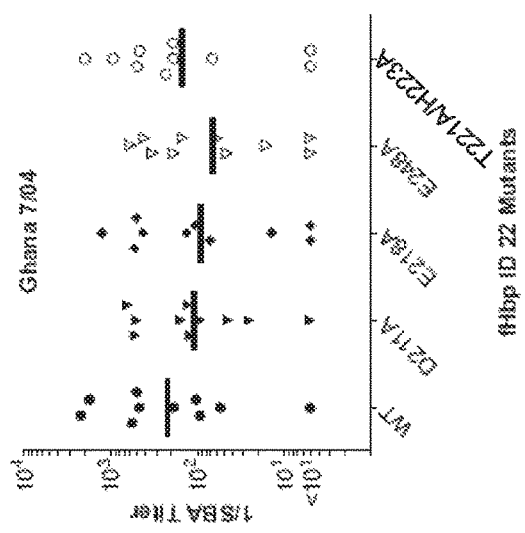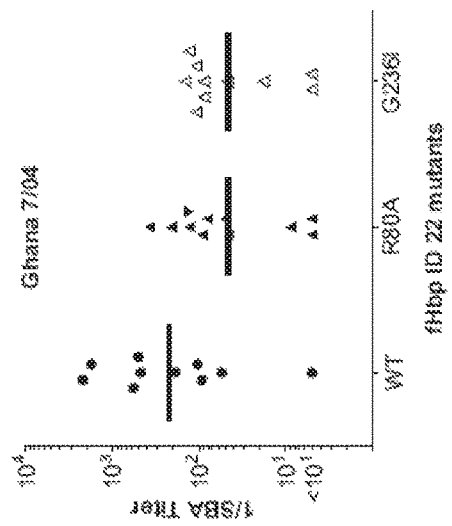
FIG. 32

```
ID_1 (v.1)        CSSGGGG-----VAADIGAGLADALTAPLDHKDKGLQSLTLDQSVRXXXEKLKLAAQGAEK  55
ID_22(v.2)        CSS---------GGGGVAADIGAGLADALTAPLDHKDKSLQSLTLDQSVRKNEKLKLAAQGAEK  55
ID_77(v.2)        CSS---------GGGGVAADIGARLADALTAPLDHKDKSLQSLTLDQSVRKNEKLKLAAQGAEK  55
ID_28(v.3)        CSSGGGGSGGGGVAADIGTGLADALTAPLDHKDKGLKSLTLEDSIPQNGTLTLSAQGAEK  60
Chimera(ID 1/77)  CSS---------GGGGVAADIGAGLADALTAPLDHKDKGLQSLTLDQSVRKNEKLKLAAQGAEK  55

ID_1              TYGNGD----SLNTGKLKNDKVSRFDEIRQIEVDGQLITTLESGEFQVYKQSHSALTAFQTE  112
ID_22             TYGNGD----SLNTGKLKNDKVSRFDEIRQIEVDGQLITTLESGEFQIYKQDHSAVVALQIE  112
ID_77             TYGNGD----SLNTGKLKNDKISRFDEIRQIEVDGQLITTLESGEFQIYKQDHSAVVALQIE  112
ID_28             TFKAGDKDNSLNTGKLKNDKVSRFDEFVQKIEVDGQTITTLASGEFQIYKQNHSAVVALQIE  120
Chimera           TYGNGD----SLNTGKLKNDKVSRFDEIRQIEVDGQLITTLESGEFQVYKQSHSALTAFQTE  112

ID_1              QIQDSEHSGKMVAKRQFRIGDIAGEHTSFDKLPEGGRATYRGTAFGSDDAGGKLTYTIDF  172
ID_22             KINNPDKIDSLINQRSFLVSGLGGEHTAFNQLP-SGKAEYHGKAFSSDDPNGRLHYSIDF  171
ID_77             KINNPDKIDSLINQRSFLVSGLGGEHTAFNQLP-DGKAEYHGKAFSSDDAGGKLTYTIDF  171
ID_28             TFKAGDKDNSLINQRSFLVSGLGGEHTAFNQLP-GGKAEYHGKAFSSDDPNGRLHYSIDE  179
Chimera           QIQDSEHSGKMVAKRQFRIGDIAGEHTAFNQLP-DGKAEYHGKAFSSDDAGGKLTYTIDF  171

ID_1              AAKQGNGKIEHLKSPELNVDLAAAIDIKPGKRHATISGSVLYNQAKGSYSLGIFGGKAQ  232
ID_22             TKKQGYGRIEHLKTPEQNVELASAELKADEKSHAVILGDTRYGSEEKGTYHLALFGDRAQ  231
ID_77             AAKQGHGKIEHLKTPEQNVELAAAELKADEKSHAVILGDTRYGSEEKGTYHLALFGDRAQ  231
ID_28             TKKQGYGRIEHLKTLEQNVELAAAELKADEKSHAVILGDTRYGSEEKGTYHLALFGDRAQ  239
Chimera           AAKQGHGKIEHLKTPEQNVELAAAELKADEKSHAVILGDTRYGSEEKGTYHLALFGDRAQ  231

ID_1              EVAGSAVVTVNGIRHIGLAAKQ  255
ID_22             EIAGSATVKIREKVHEIGIAGKQ  254
ID_77             EIAGSATVKIGEKVHEIGIAGKQ  254
ID_28             EIAGSATVKIGEKVHEIGIAGKQ  262
Chimera           EIAGSATVKIGEKVHEIGIAGKQ  254
```

FIG. 34

```
ID_1       CSSGGGGG------VAADIGAGLADALTAPLDHKDGLQSLTLDQSVKKNEKLKLAAQGAEK  55
ID_22      CSS-------GGGGVAADIGAGLADALTAPLDHKDKSLQSLTLDQSVKKNEKLKLAAQGAEK
ID_77      CSS-------GGGGVAADIGARLADALTAPLDHKDKSLQSLTLDQSVKKNEKLKLAAQGAEK
ID_28      CSSGGGGSGGGGVAADIGTGLADALTAPLDHKDKGLKSLTLEDSIPQNGTLTLSAQGAEK
Chimera    CSS-------GGGGVAADIGAGLADALTAPLDHKDKGLQSLTLDQSVKKNEKLKLAAQGAEK ID_1       TYGNGD----SLNTGKLKNDKVSRFDFTRQIEVDGLITLESGEFQVYKQSHSALTAFQTE   112
ID_22      TYGNGD----SLNTGKLKNDKVSRFDFTRQIEVDGQLITLESGEFQIYKQDHSAVVALQIE
ID_77      TYGNGD----SLNTGKLKNDKVSRFDFTRQIEVDGQLITLESGEFQIYKQDHSAVVALQIE
ID_28      TFKAGDKDNSLNTGKLKNDKISRFDFVQKIEVDGQTITLASGEFQIYKQNHSAVVALQIE
Chimera    TYGNGD----SLNTGKLKNDKVSRFDFTRQIEVDGQLITLESGEFQVYKQSHSALTAFQTE ID_1       IQDEHSKMVAKRQFIGDIAGEHTSFDKLPEGGRATYRGTAFGSDDAGGKLTYTIDF  172
ID_22      KINNPDKIDSLINQRSFLVSGLGGEHTAFNQLP-SGKAEYHGKAFSSDDPNGRLHYSIDF
ID_77      KINNPDKIDSLINQRSFLVSGLGGEHTAFNQLP-DGKAEYHGKAFSSDDAGGKLTYTIDF
ID_28      KINNPDKTDSLINQRSFLVSGLGGEHTAFNQLP-GGKAEYHGKAFSSDDPNGRLHYSIDF
Chimera    QIQDSEHSGKMVAKRQFRIGDIAGEHTAFNQLP-DGKAEYHGKAFSSDDAGGKLTYTIDF ID_1       AAKQGNGKIEHLKSPELNVDLAAADIKPDGKRHAVISGSVLYNQAKGSYSLGIFGGKAQ   232
ID_22      TKKQGYGRIEHLKTPEQNVEILASAELKASELKADEKSHAVILGDTRYGGEKGYYHLALFGDRAQ
ID_77      AAKQGHGKIEHLKTPEQNVEILAAAELKADEKSHAVILGDTRYGSEEKGTYHLALFGDRAQ
ID_28      TKKQGYGRIEHLKTLEQNVEILAAAELKADEKSHAVILGDTRYGSEKGTYHLALFGDRAQ
Chimera    AAKQGHGKIEHLKTPEQNVEILAAAELKADEKSHAVILGDTRYGSEEKGTYHLALFGDRAQ ID_1       EVAGSAVTVNGIRHIGLAAKQ  255
ID_22      EISSATVKIREKVHEIGIAGKQ
ID_77      EIAGSATVKIGEKVHEIGIAGKQ
ID_28      EIAGSATVKIGEKVHEIGIAGKQ
Chimera    EIAGSATVKIGEKVHEIGIAGKQ
```

FIG. 35

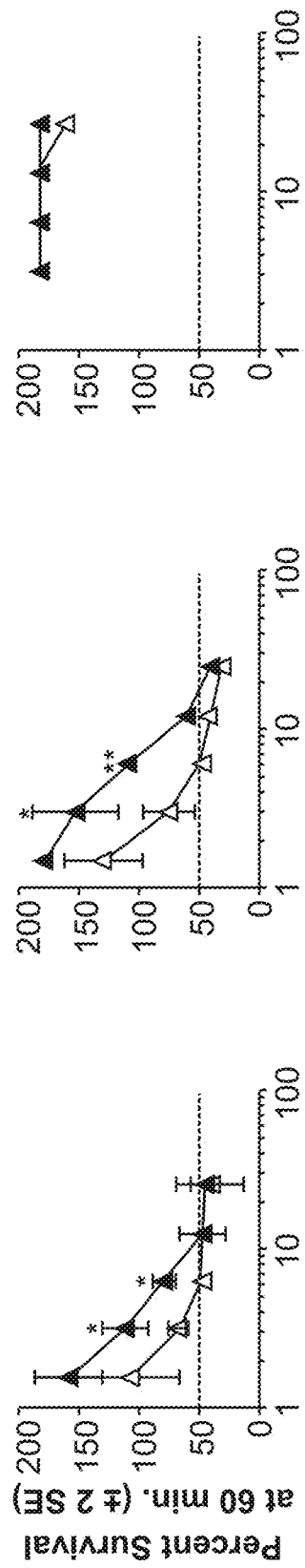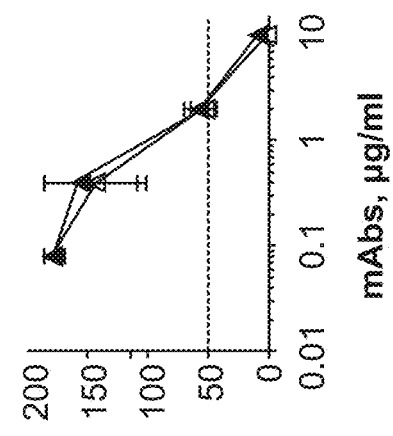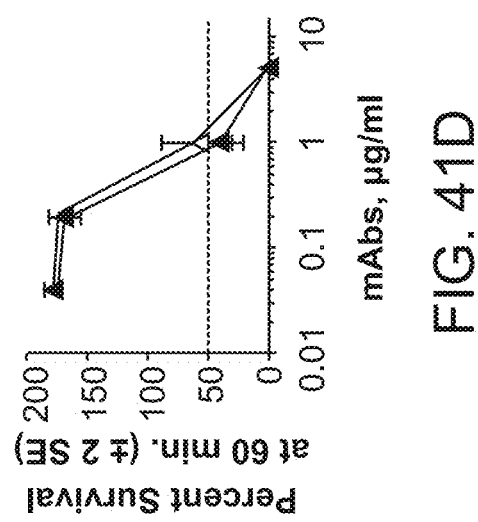

mkkalatlia lalpaaalae gasgfyvqad aahakasssl gsakgfspri sagyrindlr
61 favdytrykn ykapstdfkl ysigasaiyd fdtqspvkpy lgarlslnra svdlggsdsf
121 s

FIG. 45

Peptide ID 1
CSSGGGGVAADIGAGLADADALTAPLDHKDKGLQSLTLDQSVRKNEKLKLAAQGAEKTYGNGDSLNTGKLKN 70
DKVSRFDFIRQIEVDGQLITLESGEFQVYKQSHSALTAFQTEQIQDSEHSGKMVAKRQFRIGDIAGEHTS 140
FDKLPEGGRATYRGTAFGSDDAGGKLTYTIDFAAKQGNGKIEHLKSPELNVDLAAADIKPDGKRHAVISG 210
SVLYNQAEKGSYSLGIFGGKAQEVAGSAEVKTVNGIRHIGLAAKQ (SEQ ID NO: 1)

Peptide ID 22
CSSGGGGVAADIGAGLADADALTAPLDHKDKSLQSLTLDQSVRKNEKLKLAAQGAEKTYGNGDSLNTGKLKN 70
DKVSRFDFIRQIEVDGQLITLESGEFQIYKQDHSAVVALQIEKINNPDKIDSLINQRSFLVSGLGGEHTA 140
FNQLPSGKAEYHGKAFSSDDPNGRLHYSIDFTKKQGYGRIEHLKTPEQNVELASAELKADEKSHAVILGD 210
TRYGGEEKGTYHLALFGDRAQEIAGSATVKIREKVHEIGIAGKQ (SEQ ID NO: 2)

Peptide ID 28
CSSGGGGSGGGVAADIGTGLADADALTAPLDHKDKGLKSLTLEDSIPQNGTLTLSAQGAEKTFKAGDKDNS 70
LNTGKLKNDKISRFDFVQKIEVDGQTITLASGEFQIYKQNHSAVVALQIEKINNPDKTDSLINQRSFLVS 140
GLGGEHTAFNQLPGGKAEYHGKAFSSDDPNGRLHYSIDFTKKQGYGRIEHLKTLEQNVELAAAELKADEK 210
SHAVILGDTRYGSEEKGTYHLALFGDRAQEIAGSATVKIGEKVHEIGIAGKQ (SEQ ID NO: 3)

Peptide ID 77
CSSGGGGSGGGVAADIGARLADADALTAPLDHKDKSLQSLTLDQSVRKNEKLKLAAQGAEKTYGNGDSLNTGKLKN 70
DKVSRFDFIRQIEVDGQLITLESGEFQIYKQDHSAVVALQIEKINNPDKIDSLINQRSFLVSGLGGEHTA 140
FNQLPDGKAEYHGKAFSSDDAGGKLTYTIDFAAKQGHGKIEHLKTPEQNVELAAAELKADEKSHAVILGD 210
TRYGSEEKGTYHLALFGDRAQEIAGSATVKIGEKVHEIGIAGKQ (SEQ ID NO: 4)

Peptide ID 15
CSSGGGGSGGGVAADIGAGLADADALTAPLDHKDKGLKSLTLEDSISQNGTLTLSAQGAERTFKAGDKDNS 70
LNTGKLKNDKISRFDFIRQIEVDGQLITLESGEFQVYKQSHSALTALQTEQVQDSEHSGKMVAKRQFRIG 140
DIVGEHTSFGKLPKDVMATYRGTAFGSDDAGGKLTYTIDFAAKQGHGKIEHLKSPELNVDLAAADIKPDE 210
KHHAVISGSVLYNQAEKGSYSLGIFGGQAQEVAGSAEVETANGIRHIGLAA
KQ (SEQ ID NO: 5)

Chimera 1
cssgggvaadigagladadaltapldhkdkglqsltldqsvrkneklklaaqgaektygngdslntgklkn 70
dkvsrfdfirqievdgqlitlesgefqvykqshsaltafqteqiqdsehsgkmvakrqfrigdiaGEHTA 140
FNQLPDGKAEYHGKAFSSDDAGGKLTYTIDFAAKQGHGKIEHLKTPEQNVELAAAELKADEKSHAVILGD 210
TRYGSEEKGTYHLALFGDRAQEIAGSATVKIGEKVHEIGIAGKQ (SEQ ID NO: 8)

FACTOR H BINDING PROTEINS (FHBP) WITH ALTERED PROPERTIES AND METHODS OF USE THEREOF

CROSS REFERENCE

This application is a divisional of U.S. patent application Ser. No. 15/792,519, now U.S. Pat. No. 10,342,860, which claims the benefit of continuation U.S. patent application Ser. No. 13/074,957, now U.S. Pat. No. 9,827,300, which claims the benefit of U.S. Provisional Patent Application Nos. 61/319,181, filed Mar. 30, 2010, 61/334,542, filed May 13, 2010, 61/381,025, filed Sep. 8, 2010, 61/423,757, filed Dec. 16, 2010, and 61/440,227, filed Feb. 7, 2011, each of which applications is incorporated herein by reference in its entirety.

STATEMENT REGARDING FEDERALLY SPONSORED RESEARCH

This invention was made with government support under grant nos. RO1 AI 046464, RO1 AI 082263, and AI 070955 awarded by the National Institute of Allergy and Infectious Diseases, National Institutes of Health. The government has certain rights in the invention.

INTRODUCTION

*Neisseria meningitidis* is a Gram-negative bacterium which colonizes the human upper respiratory tract and is responsible for worldwide sporadic and cyclical epidemic outbreaks of, most notably, meningitis and sepsis. The attack and morbidity rates are highest in children under 2 years of age. Like other Gram-negative bacteria, *Neisseria meningitidis* typically possess a cytoplasmic membrane, a peptidoglycan layer, an outer membrane which together with the capsular polysaccharide constitute the bacterial wall, and pili, which project into the outside environment. Encapsulated strains of *Neisseria meningitidis* are a major cause of bacterial meningitis and septicemia in children and young adults. The prevalence and economic importance of invasive *Neisseria meningitidis* infections have driven the search for effective vaccines that can confer immunity across different strains, and particularly across genetically diverse group B strains with different serotypes or serosubtypes.

Factor H Binding Protein (fHbp, also referred to in the art as lipoprotein 2086 (Fletcher et al (2004) *Infect Immun* 72:2088-2100), Genome-derived Neisserial antigen (GNA) 1870 (Masignani et al. (2003) *J Exp Med* 197:789-99) or "741") is an *N. meningitidis* protein which is expressed in the bacterium as a surface-exposed lipoprotein. An important function of fHbp is to bind human complement factor H (fH), which down-regulates complement activation. Binding of fH to the bacterial surface is an important mechanism by which the pathogen survives in non-immune human serum or blood and evades innate host defenses. Recently, genetic variation in the human factor H gene cluster was found to affect susceptibility to developing meningococcal disease (Davila S et al. (2010) Nat Genetics doi:10.1038/ng.640). Binding of fH to fHbp is specific for human fH and could account for why *Neisseria meningitidis* is strictly a human pathogen.

There remains a need for a fHbp polypeptide that can elicit effective bactericidal antibody responses.

SUMMARY

Factor H binding proteins that can elicit antibodies that are bactericidal for at least one strain of *N. meningitidis*, and methods of use of such proteins, are provided.

BRIEF DESCRIPTION OF THE DRAWINGS

FIG. 4. Binding of human fH, and anti-fHbp mAbs, JAR 4, and JAR 5, by wild-type and mutant fHbps (mutants of fHbp ID1 containing Glu to Ala substitutions) as measured by enzyme-linked immunosorbent assay (ELISA).

FIG. 5. SDS-PAGE size and purity analysis of WT fHbp ID 1 and a double mutant of ID 1, E218A/E239A. The molecular masses in kDa are indicated on the left.

FIGS. 7A and 7B depict differential scanning calorimetry of fHbp ID 1 wildtype and E218A/E239A double mutant protein (FIG. 7A) and of fHbp ID 1 wildtype and R41S mutant protein (FIG. 7B). FIG. 7C depicts anti-fHbp IgG antibody titers of mice immunized with fHbp ID 1 wildtype or E218A/E239A double mutant protein determined by ELISA. IgG Anti-fHbp antibody responses of mice immunized with WT or mutant fHbp. In Study 3, mice were immunized with three doses of recombinant WT or mutant fHbp adsorbed with Freund's Adjuvant (FA) or aluminum hydroxide (Al(OH)$_3$); in Study 4, CD-1 mice were immunized with one dose of WT or mutant fHbp adsorbed with aluminum hydroxide (Al(OH)$_3$); in Study 5, BALB/c mice were immunized with three doses of WT or mutant fHbp adsorbed with aluminum hydroxide (Al(OH)$_3$). Shaded bars, WT fHbp; open bars, E218A/E239A mutant fHbp. FIG. 7D depicts anti-fHbp IgG titers of BALB/c mice that were given two doses of fHbp vaccine in Study 6.

Binding of human fH was measured as described in the Examples section. Panels B and C depict binding of the variants fHbp IDs 1, 14, and 15 to MAb JAR4 and JAR5, respectively.

Figure 9A:
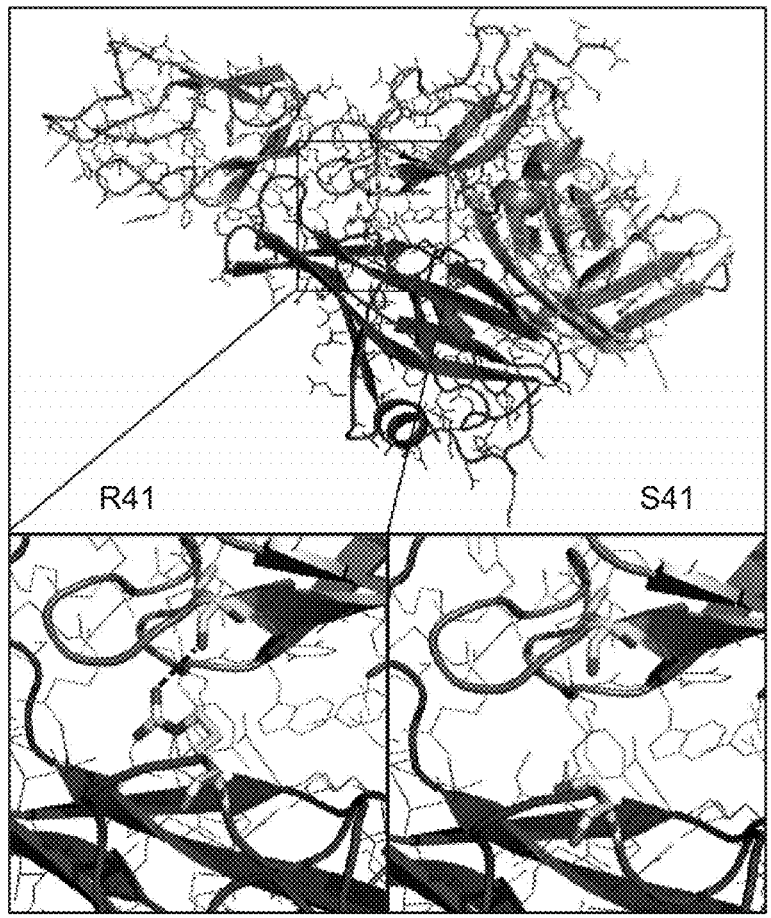

FIG. 9A. Structure of the complex between fHbp and a fragment of human fH. fHbp is shown on the bottom in black with fH shown at the top in grey in cartoon representation. Structural model of fHbp bound to a fragment of fH based on published atomic coordinates (Schneider et al. ((2009) *Nature* 458:890-3)). The black ribbons represent the respective N- and C-terminal domains of the fHbp molecule. The gray ribbon represents the sixth and seventh short consensus repeat domains of human fH previously shown to mediate the interaction of human fH and fHbp (Schneider et al. ((2009) *Nature* 458:890-3). The zoomed-in view on the left focuses on the arginine residue at position 41, showing a charged H-bond with fH, which was predicted to be eliminated when arginine was replaced by serine (right lower inset). The figure was generated using MacPyMol (www.pymol.org).

FIG. 9B shows the amino acid sequence of human factor H (fH), which is also known as GenBank accession no. NP_000177 (P08603), and its encoding nucleic acid as NM_000186.

Figure 10:
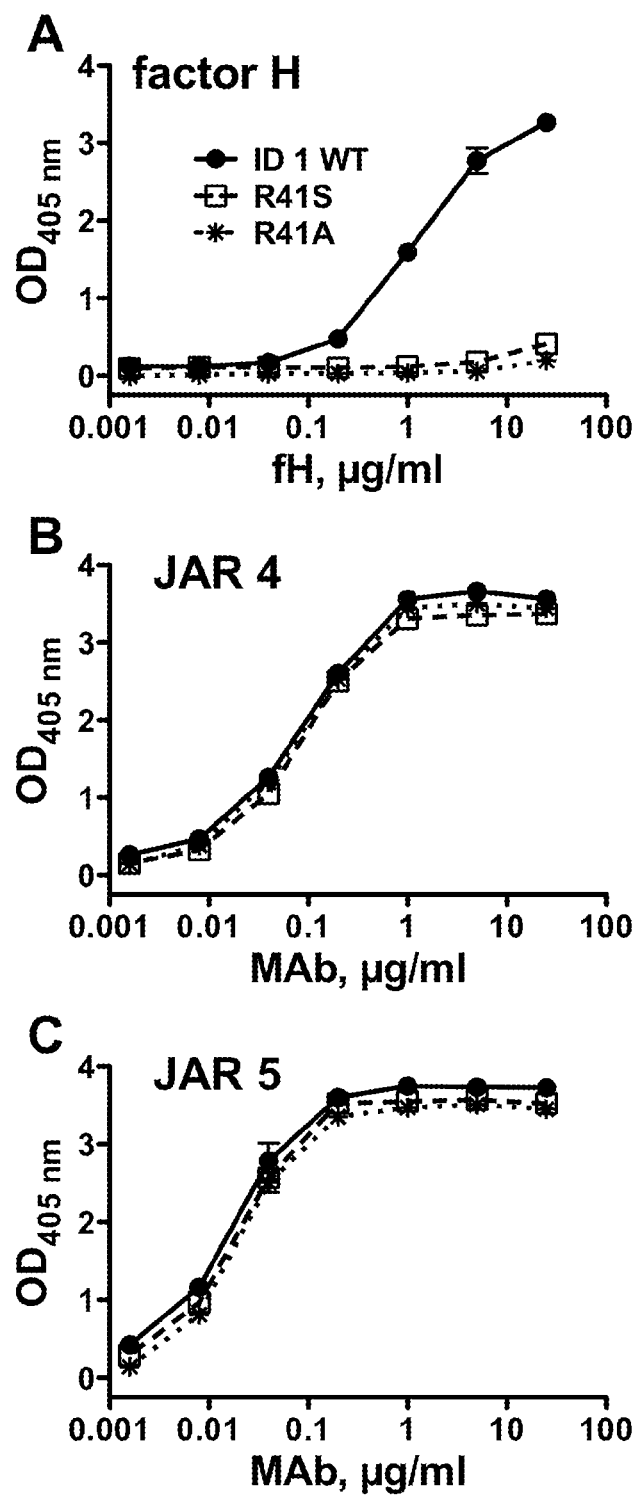

FIG. 10. Binding of fH (panel A) or anti-fHbp MAbs JAR 4 (panel B) or JAR 5 (panel C) to R41S and R41A mutants of fHbp ID 1, as measured by ELISA. Binding of human fH (panel A), and anti-fHbp MAbs (panels B and C) was measured as described in Example 2.

FIG. 11. Binding of human factor H (left column) or anti-fHbp MAb JAR 4 (right column) to different fHbps in variant group 1 and their corresponding R41S mutants. Binding was measured as described in Example 2. Panels A and B show the binding results for fHbp ID 4. Panels C and D show the binding results for fHbp ID 9. Panels E and F show the binding results for fHbp ID 74. "ID" refers to fHbp amino acid sequence variant identification (ID) number, as described in the *Neisseria* Multi Locus Sequence Typing website (hypertext transfer protocol)://pubmlst(dot)org/neisseria/fHbp/.

FIG. 12. Binding of human fH and control anti-fHbp MAbs to fHbp and corresponding R41S mutants of fHbps in variant group 2. Panels A and B show binding of human factor H to wildtype (WT) fHbp ID 19 and R41S mutant of fHbp ID 19. Panels C and D show binding of human factor H to WT fHbp ID 22 and R41S mutant of fHbp ID 22. Panels E and F show binding of human factor H to WT fHbp ID 77 and R41S mutant of fHbp ID 77. The MAb controls were JAR 4 (Panels B and D) or JAR 11 (Panel F).

FIG. 13. Effect of serum anti-fHbp antibody elicited in human fH transgenic mice on fH binding to fHbp. Binding of fH to fHbp was measured by ELISA in 1:100 dilutions of pre-immunization (panel A, pre-immune) and post-immunization (panel B, post-immune) sera from individual transgenic mice immunized with wild-type fHbp ID 1 or R41S mutant ID 1 fHbp vaccines. For the aluminum control groups, the open squares represent data from serum pools from transgenic mice whose sera contain human fH and the closed triangles represent data from sera from wild-type mice whose sera do not contain human fH. The OD values represent the quantity of bound human fH as detected with sheep anti-human fH and donkey anti-sheep IgG conjugated to alkaline phosphatase. Panel C, IgG anti-fHbp titers in post-immunization sera showing similar antibody responses to both vaccines. Panel D, Inhibition of binding of human fH to fHbp in the presence of added human fH. Panel E, Relationship of percent inhibition of fH binding and SBA titers of human fH transgenic mice immunized with fHbp vaccines.

FIG. 14. Binding of fH with a K241E mutant of fHbp ID 1 and its binding to MAb JAR 5 are shown in panels A and B, respectively. Binding of fH with an E241K mutant of fHbp ID 15 and its binding to MAb JAR 5 are shown in panels C and D, respectively. fH or anti-fHbp MAb binding to fHbp was measured as described in Example 2.

FIG. 15. Binding of fH or anti-fHbp MAbs to H119A and R130A single mutants of fHbp ID 1, as measured by ELISA. Binding of human fH (panel A), and anti-fHbp MAbs JAR 5 (panel B), or JAR 4 (panel C), was measured as described in Example 2.

FIG. 16. Schematic representation of the six most common fHbp modular groups, designated I to VI. The variable segments are each derived from one of two genetic lineages, designated α (shown in gray) or β (white). The α and β lineages can also be designated as lineages 1 and 2, respectively, according to the nomenclature adopted by the pubmlst.org/neisseria/fHbp/ website. Segment $V_A$ began at amino acid residue 8 and extended to position 73 while segment $V_B$ began at position 79 and extended to position 93 (numbering of the amino acid residue based on the sequence of fHbp ID 1). Segment $V_C$ began at amino acid residue 98 and extended to position 159 while segment $V_D$ began at position 161 and extended to position 180. Segment $V_E$ began at amino acid residue 186 and extended to position 253. Of the 70 fHbp amino acid sequence variants analyzed, 33 contained only α type segments, and 7 contained only β type segments, which were designated as modular groups I and II, respectively. The remaining 30 fHbp variants were natural chimeras with different combinations of α and β segments and could be assigned to one of four modular groups (III-VI). The relationship between the modular group and Masignani variant group designation, and the number of unique sequences observed within each fHbp modular group, are shown. The modular architecture of the engineered (non-naturally occurring) fHbp chimera I is shown as the last modular schematic in FIG. 16. For a chimeric protein engineered from fHbp ID 1 and ID 77 "chimera I" (Beernink et al. (2008) *Infec. Immun.* 76:2568-2575), four amino acid residues, GEHT (SEQ ID NO:27) at position 136 to 139 represents the junction point in the $V_C$ segment (See FIG. 19). ID refers to fHbp sequence peptide identification number as described on the public website, (hypertext transfer protocol)://pubmlst.org/neisseria/fHbp/.

FIG. 17. Binding of fH with recombinant fHbp mutant S41P (mutant of fHbp ID 15). Binding of fH with an S41P mutant of fHbp ID 15 is shown in Panel A. Binding of the S41P mutant of fHbp ID15 to MAb JAR 5 and to MAb JAR31 are shown in panels B and C, respectively. "Pep28" is fHbp ID 28; "Pepl" is fHbp ID 1; "Pep 15 WT" is fHbp ID 15; and "Pep 15 S41P" is the S41P mutant of fHbp ID 15.

FIG. 18. Binding of human fH to R41S mutant of the fHbp chimera I (Beernink et al. (2008) *Infec. Immun.* 76:2568-2575) (panel A) and corresponding binding of JAR 5 (Panel B).

FIG. 19A. Alignment of fHbp sequences of natural variants and a man-made chimera (chimera I; Beernink et al. (2008) *Infec. Immun.* 76:2568-2575). fHbp ID 1 is in modular group I (all five variable segments, A-E, are derived from α lineages as defined by Beernink and Granoff (2009) *Microbiology* 155:2873-83). fHbp ID 28 is in modular group II (all five segments are derived from β lineages). fHbp ID 15 is a natural chimera (modular group IV with a β A segment and α B, C, D and E segments). The β-type A segment ($V_A$; residues 8-73) of fHbp ID 28 is shown for comparison with the corresponding A segment ($V_A$) of fHbp ID 15, which also has a β-type A segment ($V_A$β). The residues changed in the E218A/E239A double mutant fHbp are shown in rectangles. FIG. 19B, Alignment of the A segment (amino acid residues 8 to 73) of fHbp ID 1 and fHbp ID 77. FIG. 19C, Alignment of the C segment (amino acid residues 98-159) of fHbp ID 1 and fHbp ID 77. The junction point is at residue 136. Chimeric fHbp includes the amino acid sequences from ID1 up to residue G136, and the sequence of fHbp ID 77 from residue 136 to the C terminus. FIG. 19D, Alignment showing natural polymorphisms at amino acid position 41 (number according to that of fHbp ID 1); some variants have arginine (R41, ID 1, 19, 4, 9 and 74) while other variants have serine (S41, ID 55, 15) or proline (P41, ID 28). ID refers to fHbp sequence ID; MG refers to fHbp modular group; and VG refers to variant group. FIG. 19E, Alignment of fHbp ID 1, fHbp ID 77 and chimera I. Shaded residues in fHbp ID 77 highlight the residues in segment $V_C$ that are different from the corresponding positions in chimera I. Bolded and shaded residues correspond to K113, K119, and D121, in order of N-terminus to C-terminus.

Figure 20:
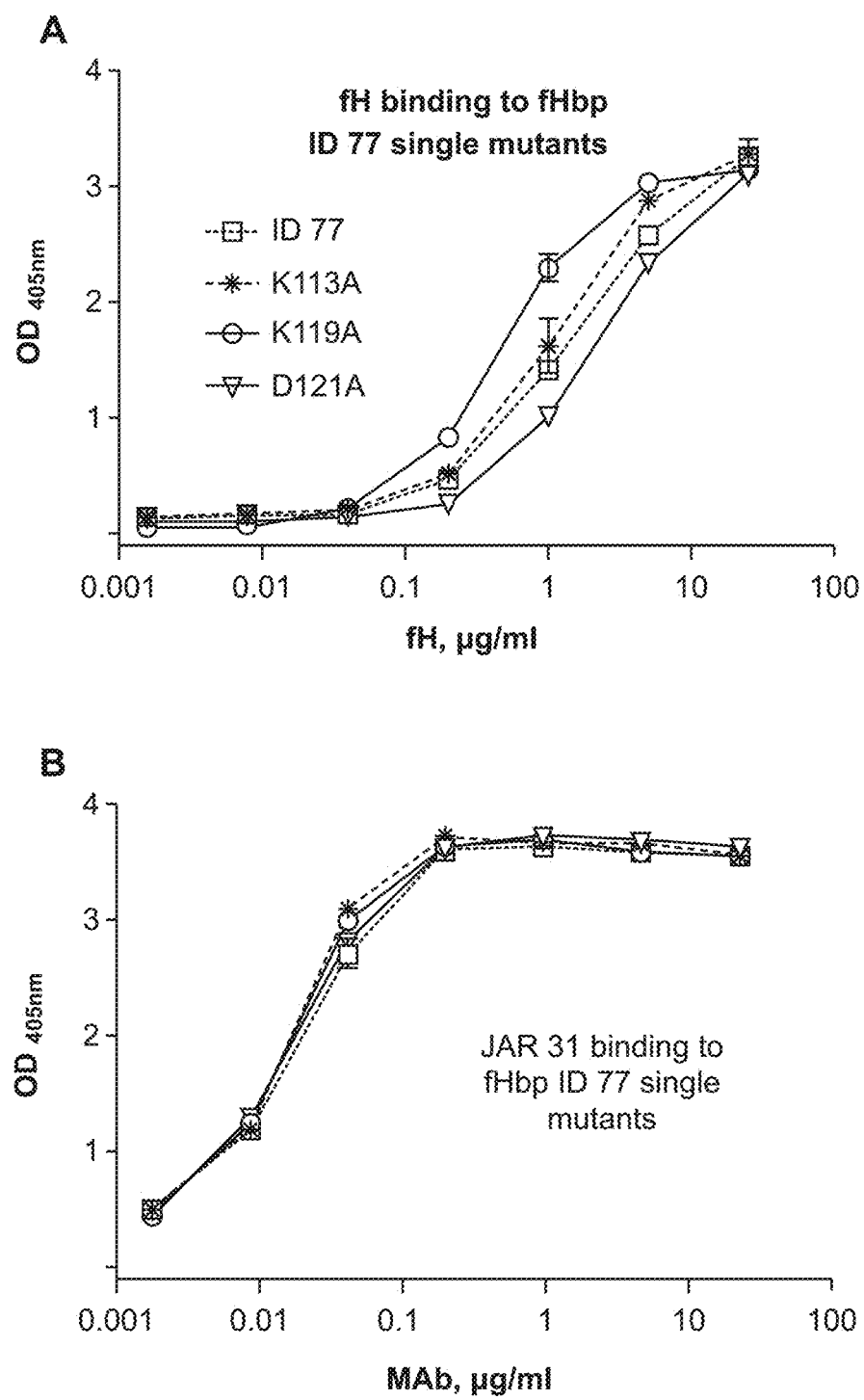

FIG. 20. Binding of fH or an anti-fHbp MAb to K113A, K119A, and D121A single mutants of fHbp ID 77, as measured by ELISA. Binding of human fH (panel A), and anti-fHbp MAb JAR 31 (panel B) was measured as described in Example 2.

Figure 21:
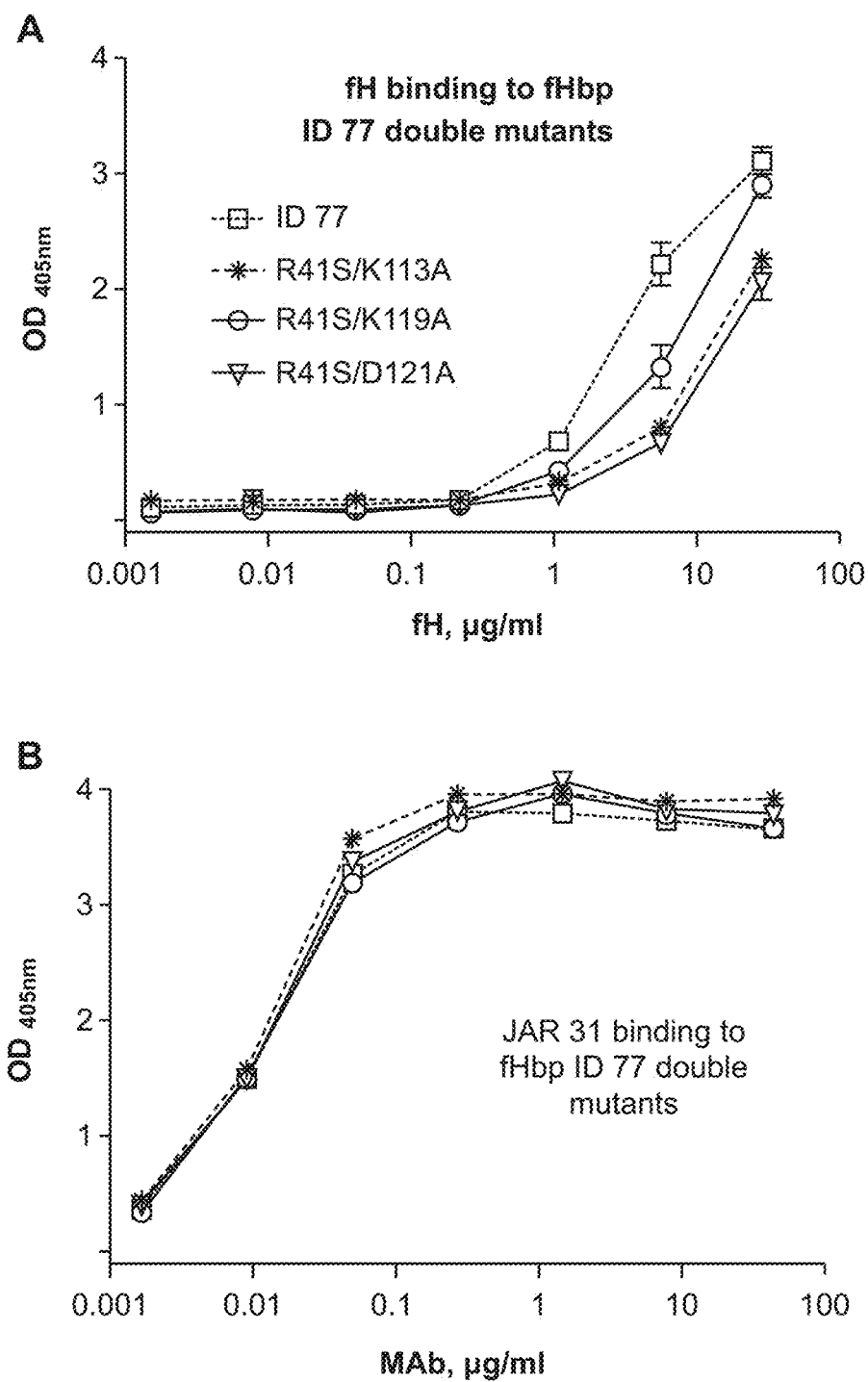

FIG. 21. Binding of fH or an anti-fHbp MAb to R41S/K113A, R41S/K119A, and R41S/D121A double mutants of fHbp ID 77, as measured by ELISA. Binding of human fH (panel A), and anti-fHbp MAb JAR 31 (panel B) was measured as described in Example 2.

Figure 22:
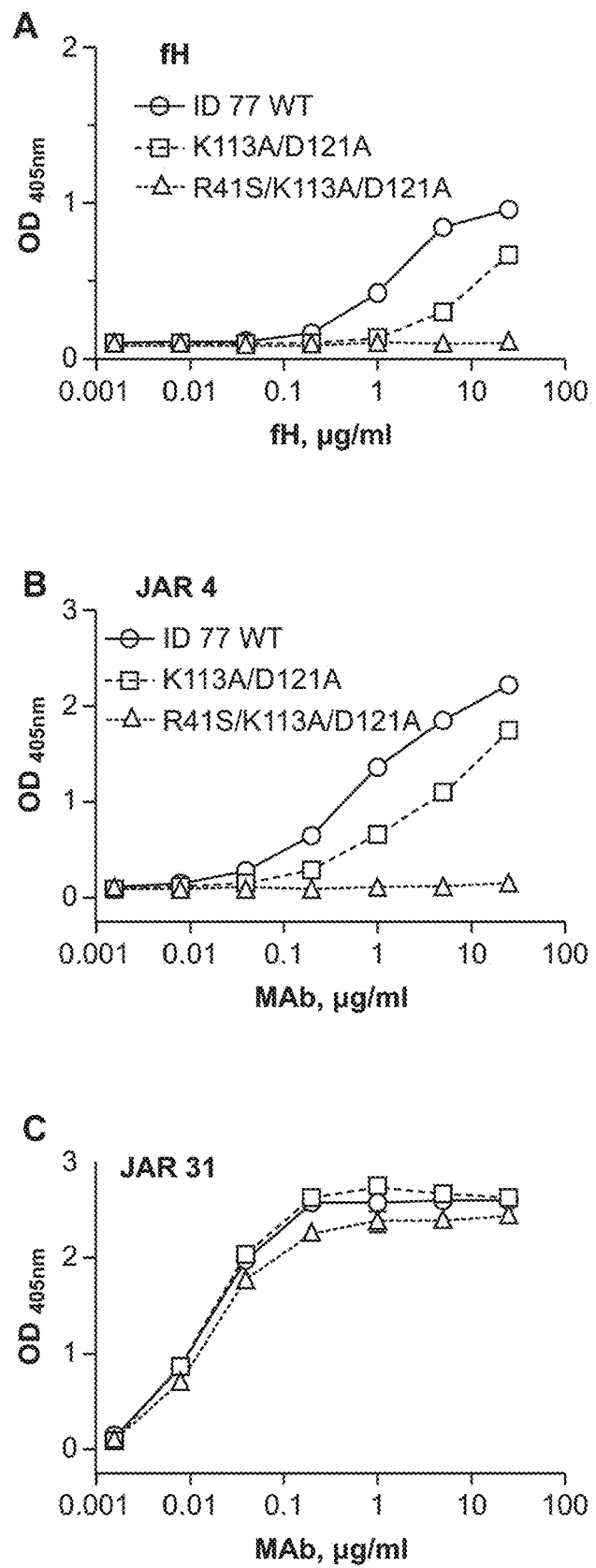

FIG. 22. Binding of fH or an anti-fHbp MAb to K113A/D121A double mutant and R41S/K113A/D121A triple mutant of fHbp ID 77, as measured by ELISA. Binding of human fH (panel A), anti-fHbp MAb JAR 4 (panel B), and anti-fHbp MAb JAR 31 (panel C) was measured as described in Example 2.

Figure 23:
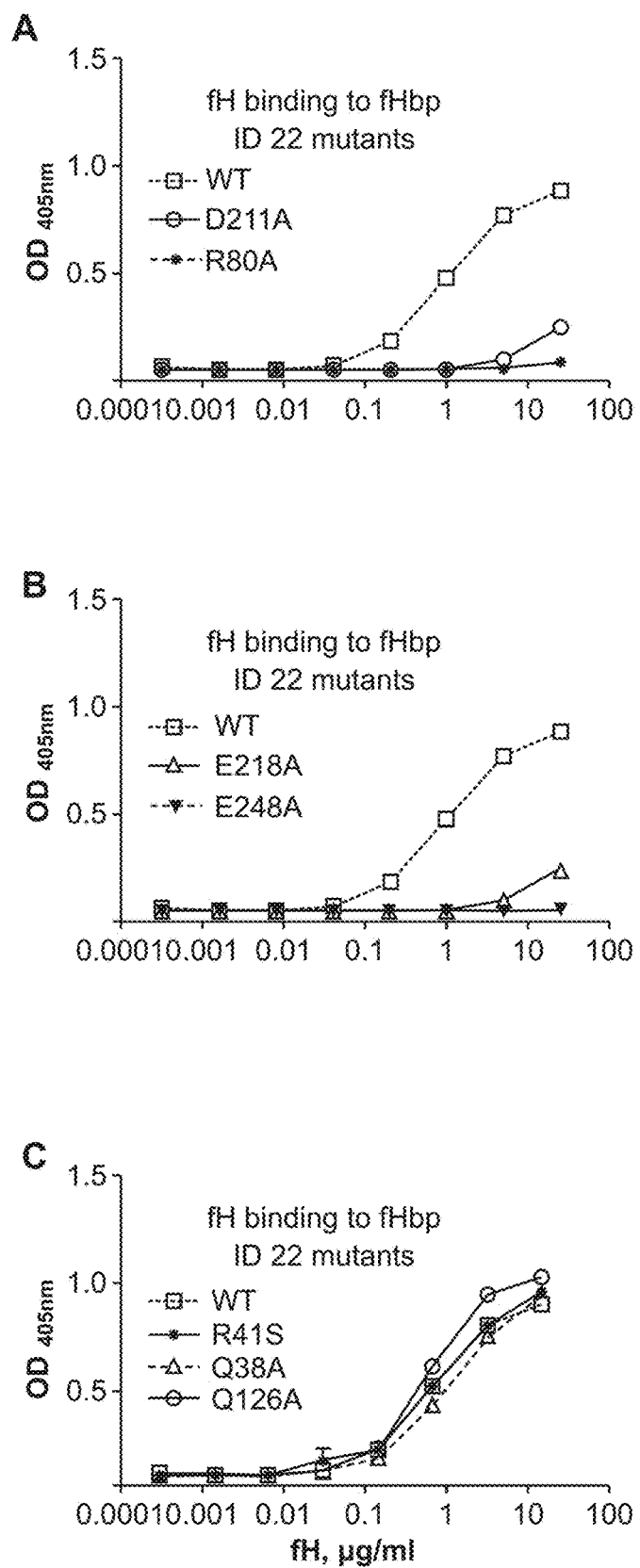

FIG. 23. Binding of fH to mutants of fHbp ID 22, as measured by ELISA. Binding of human fH to D211A, R80A, or wild-type fHbp (panel A), to E218A, E248A, or wild-type fHbp (panel B), and to R41S, Q38A, Q126A, or wild-type fHbp (panel C) was measured as described in Example 2.

FIG. 24. Binding of anti-fHbp MAb JAR31 to mutants of fHbp ID 22, as measured by ELISA. Binding of R80A and D211A mutants (panel A), and binding of E218A and E248A mutants (panel B) to JAR31 was measured as described in Example 2.

FIG. 25. Binding of anti-fHbp MAb JAR4 to mutants of fHbp ID 22, as measured by ELISA. Binding of R80A and D211A mutants (panel A), and binding of E218A and E248A mutants (panel B) to JAR 4 was measured as described in Example 2.

FIG. 26. Binding of anti-fHbp MAb JAR35 to mutants of fHbp ID 22, as measured by ELISA. Binding of R80A and D211A mutants (panel A), and binding of E218A and E248A mutants (panel B) to JAR35 was measured as described in Example 2.

Figure 27:
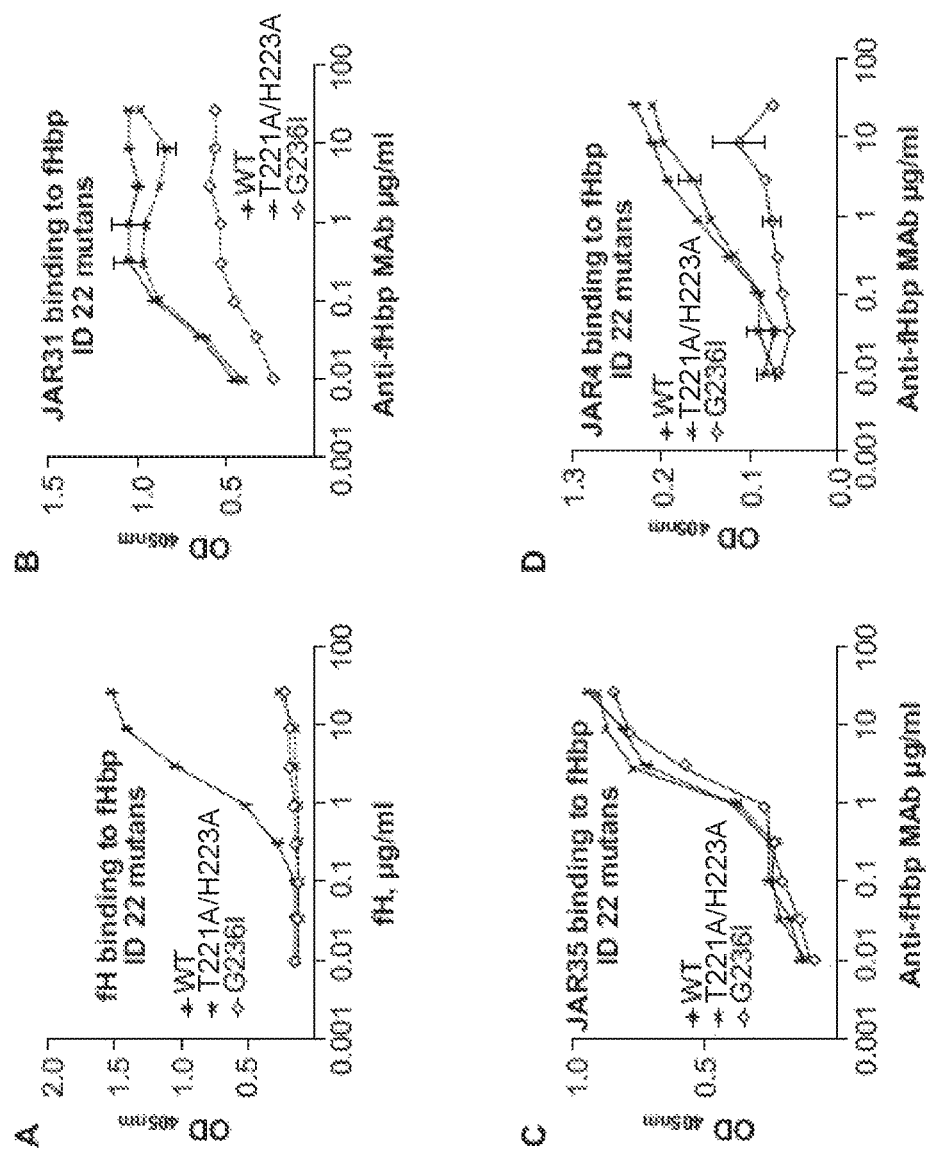

FIG. 27. Binding of fH or anti-fHbp MAbs to a T221A/H223A double mutant, or a G236I mutant, of fHbp ID 22, as measured by ELISA. Binding of human fH (panel A), and anti-fHbp MAbs JAR 31 (panel B), JAR 35 (panel C), or JAR 4 (panel D), was measured as described in Example 2.

Figure 28:
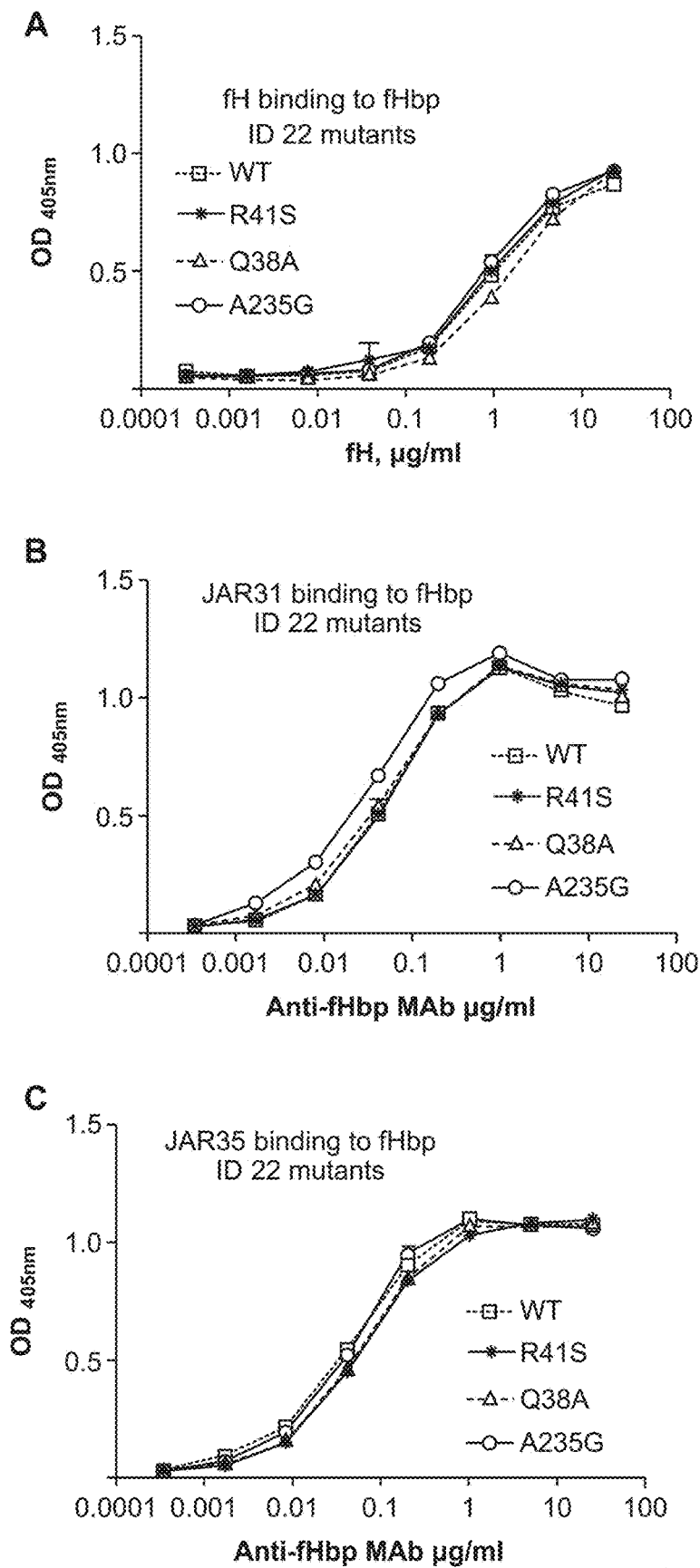

FIG. 28. Binding of fH or anti-fHbp MAbs to R41S, Q38A, and A235G mutants of fHbp ID 22, as measured by ELISA. Binding of human fH (panel A), and anti-fHbp MAbs JAR 31 (panel B), or JAR 35 (panel C), was measured as described in Example 2.

Figure 29:
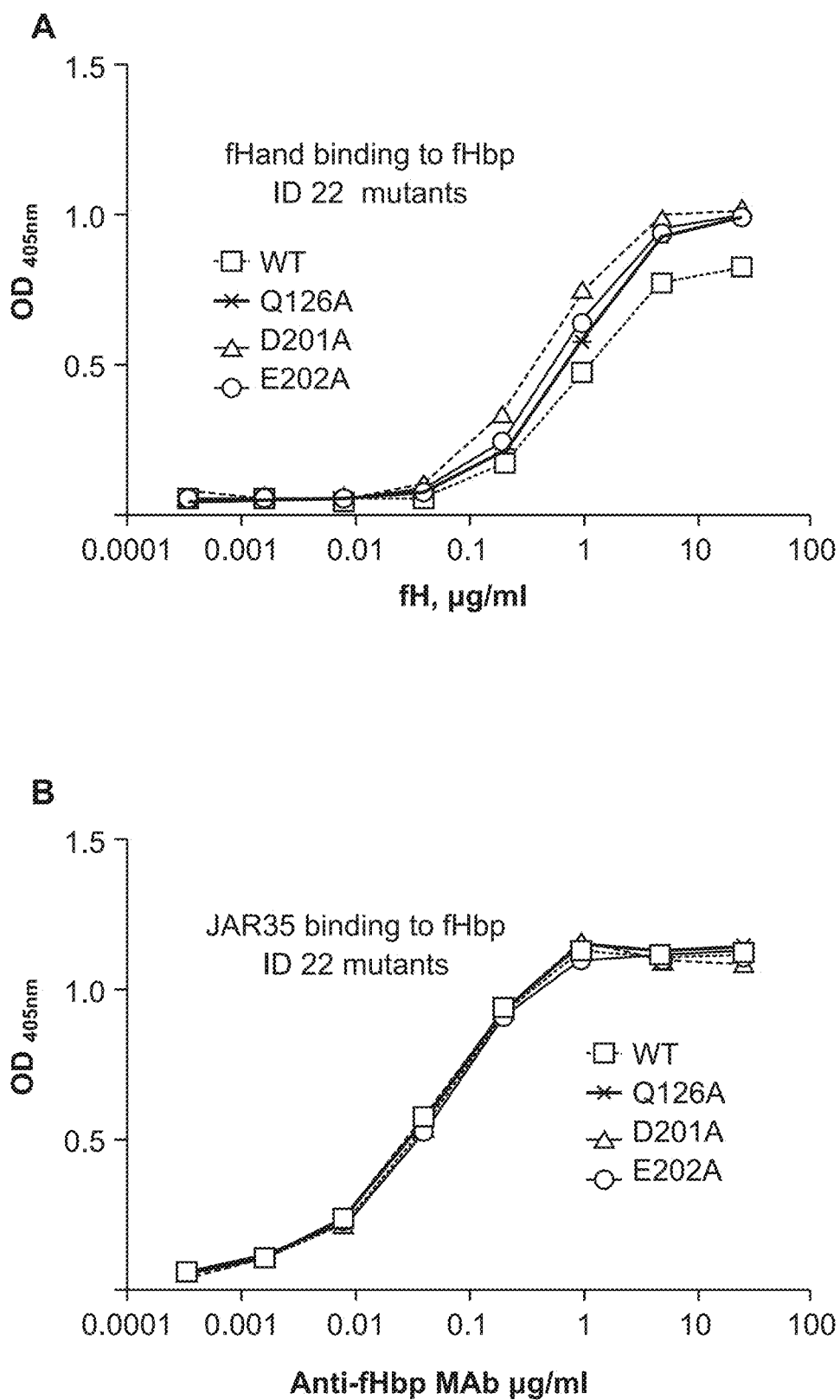

FIG. 29. Binding of fH or an anti-fHbp MAb to Q126A, D201A, and E202A mutants of fHbp ID 22, as measured by ELISA. Binding of human fH (panel A), and anti-fHbp MAb JAR 35 (panel B) was measured as described in Example 2.

FIG. 30. Binding to mutants of fHbp ID 28 (variant group 3). Panels A and C. Binding of fH to K199A, E217A, and E218A mutants as measured by ELISA. Panels B and D. Binding of anti-fHbp MAb JAR 31 (panel B), and anti-fHbp MAb JAR 33 (panel D, fHbp wildtype ID 28 WT and E218A mutant only) are shown.

Figure 31:
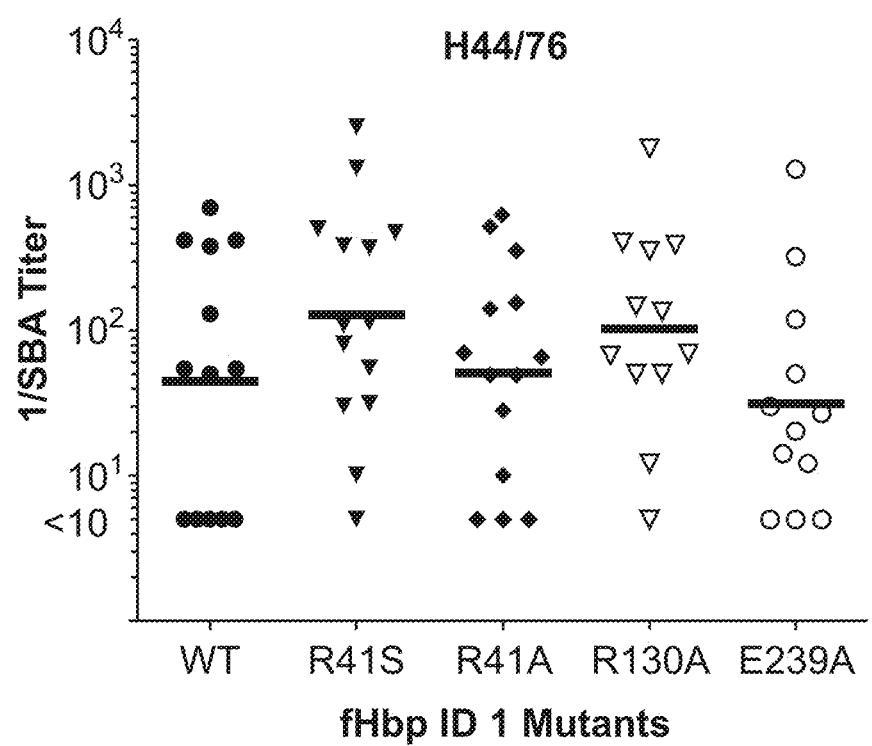

FIG. 31 depicts serum bactericidal titers of wildtype BALB/c mice immunized with the indicated mutants of fHbp ID 1 vaccine and measured against group B strain H44/76 (fHbp ID 1).

FIG. 32 depicts serum bactericidal titers of mice immunized with the indicated mutants of fHbp ID 22 as measured against group W-135 strain Ghana 7/04 (fHbp ID 23). Upper panel, mutant vaccines with titers that were not significantly different from that of the wildtype (WT) fHbp ID 22 vaccine (P>0.10). Lower panel, mutant vaccines that elicited significantly lower titers than the control WT ID 22 vaccine (P<0.05).

Figure 33:
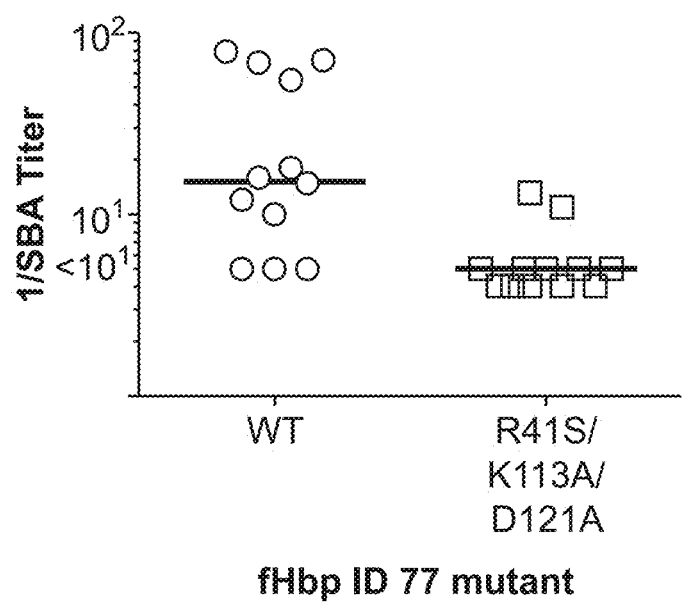

FIG. 33 depicts bactericidal titers of mice immunized with a triple R41S/K113A/D121A mutant of fHbp ID 77 as measured against group W-135 strain Ghana 7/04 (fHbp ID 23).

FIG. 34. Alignment of fHbp ID 1 (SEQ ID NO:1), fHbp ID 22 (SEQ ID NO:2), fHbp ID 77 (SEQ ID NO:4), fHbp ID 28 (SEQ ID NO:3), and ID1/ID77 chimera (SEQ ID NO:8) amino acid sequences. ID 28 is shown as a reference sequence for fHbp variant group 3. Predicted factor H binding interface residues with hydrogen bond or ionic interactions (highlighted in gray) from a crystal structure of fHbp ID1 in a complex with a fragment of fH, as described in Schneider et al. ((2009) *Nature* 458:890-3). GEHT (SEQ ID NO:27) (in bold) at position 136 to 139 represents the junction point between ID 1 and ID 77 for the chimeric fHbp.

FIG. 35. Alignment of fHbp ID 1 (SEQ ID NO:1), fHbp ID 22 (SEQ ID NO:2), fHbp ID 77 (SEQ ID NO:4), fHbp ID 28 (SEQ ID NO:3), and ID1/ID77 chimera (SEQ ID NO:8) amino acid sequences. Residues highlighted in gray indicate residues mutated and summarized in Table 7.

Figure 36:
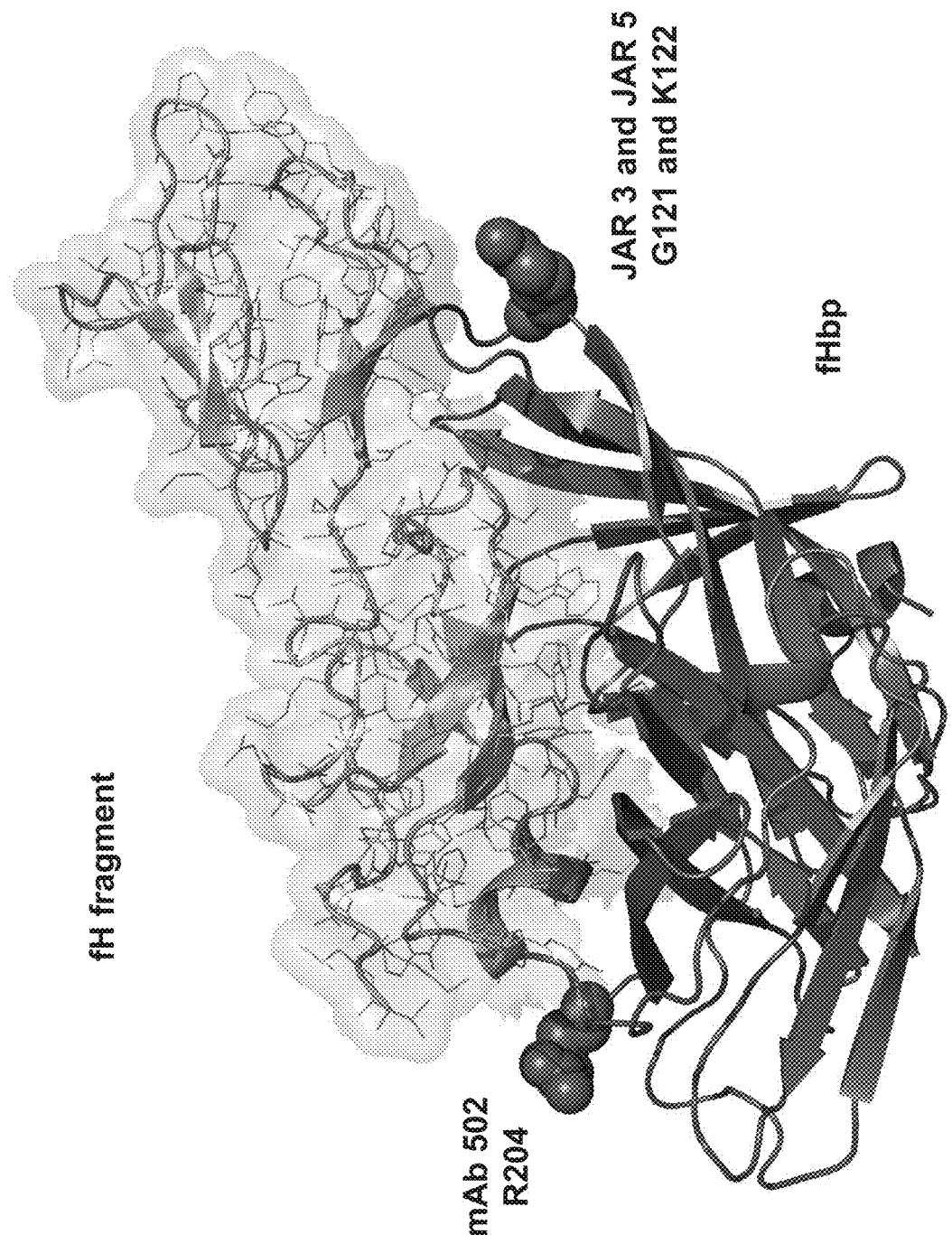

FIG. 36 depicts a model of fHbp in a complex with a fragment of fH. The positions of the amino acid residues known to affect the epitopes of anti-fHbp mAb JAR 3 and JAR 5 (G121 and K122) and mAb 502 (R204) are depicted.

Figure 37A:
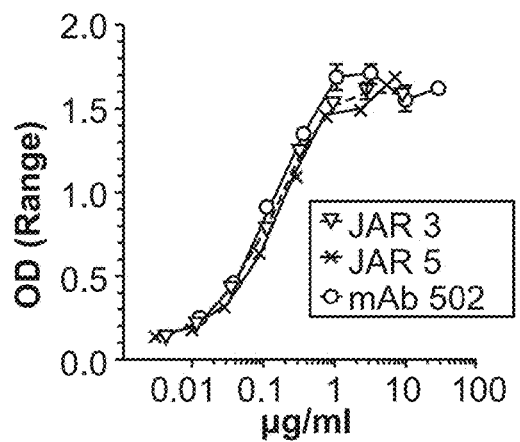
Figure 37B:
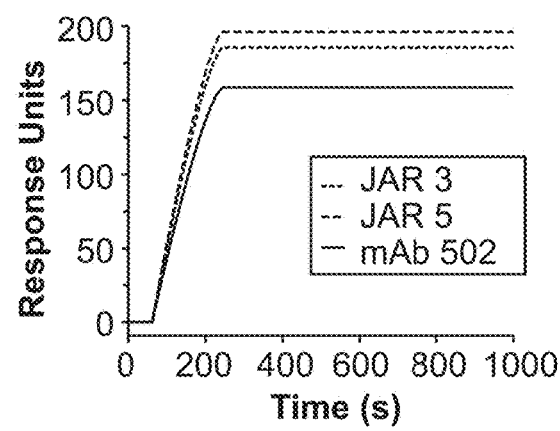
Figure 37C:
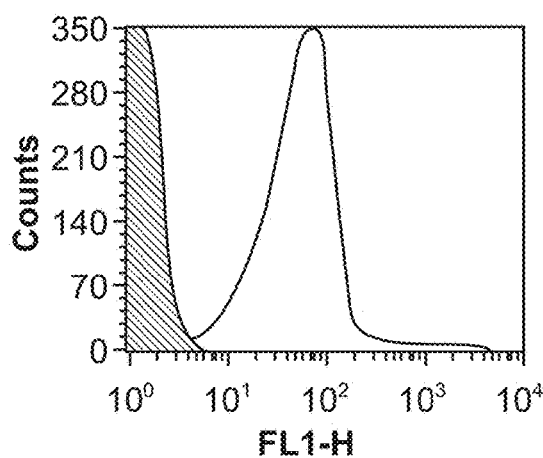
Figure 37D:
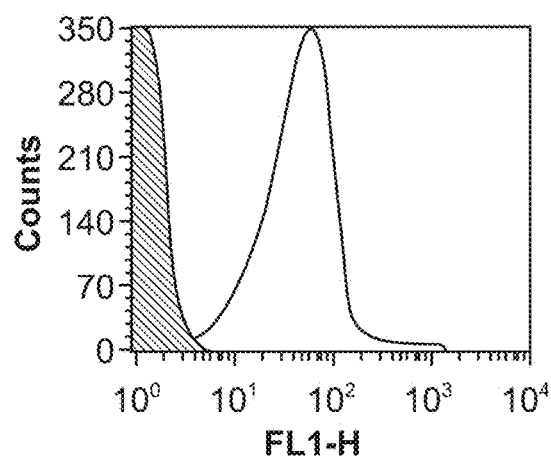

FIGS. 37A-37D depict binding of human IgGa mouse chimeric fHbp-specific mAbs to fHbp as measured by ELISA (FIG. 37A), plasmon resonance (FIG. 37B) or to live bacteria by flow cytometry (FIG. 37C, mAbs alone; and FIG. 37D, mAbs in the presence of 20% human serum depleted of IgG).

Figure 38A:
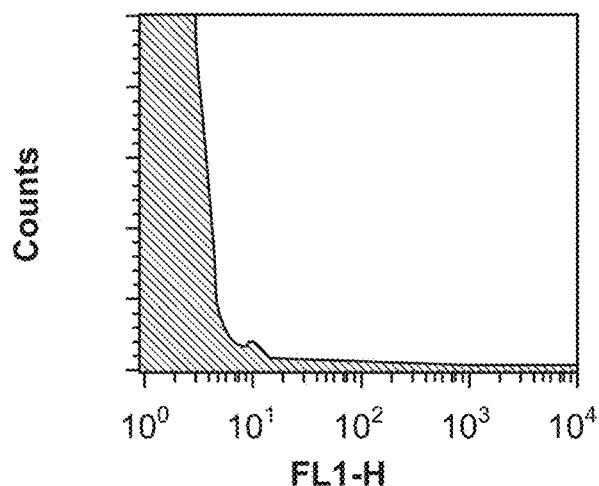
Figure 38B:
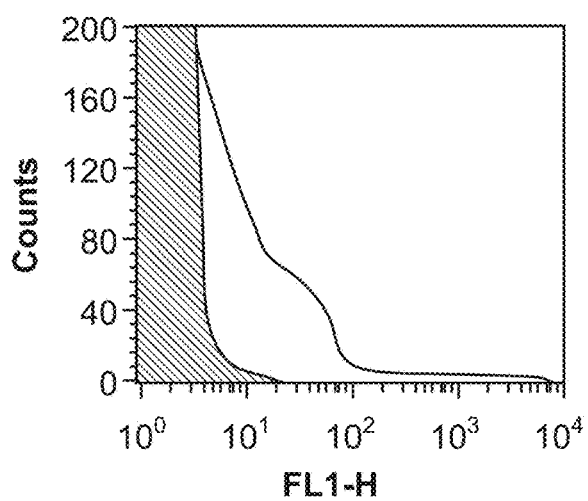
Figure 38C:
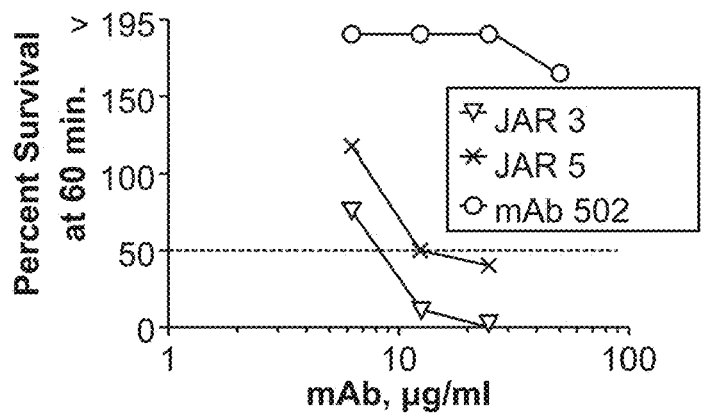

FIGS. 38A-38C. FIGS. 38A-38B depict C1q-dependent C4b deposition from complement activation on encapsulated group B bacteria of strain H44/76 by human IgG1 mouse chimeric anti-fHbp mAbs JAR 3, JAR 5 and mAb 502. FIG. 38A, C1q-depleted human serum as complement source; FIG. 38B, C1q-depleted serum that had been repleted with purified C1q protein prior to the reactions. FIG. 38C depicts human complement-mediated bactericidal activity of the respective mAbs as measured against group B strain H44/76.

Figure 39A:
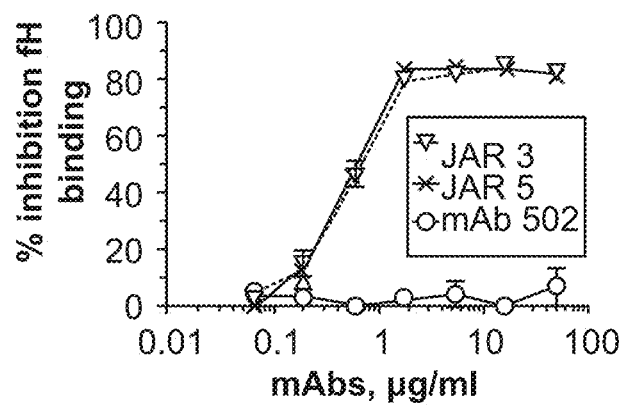
Figure 39B:
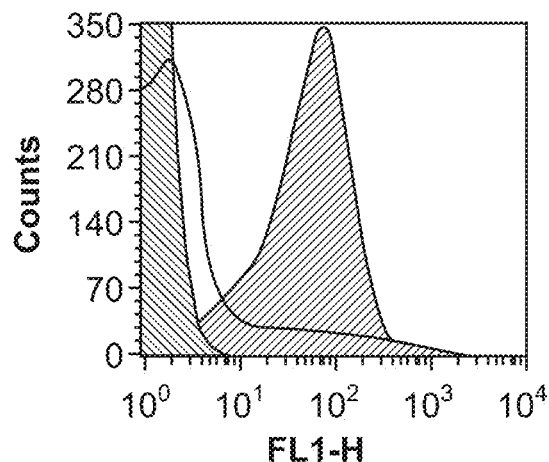
Figure 39C:
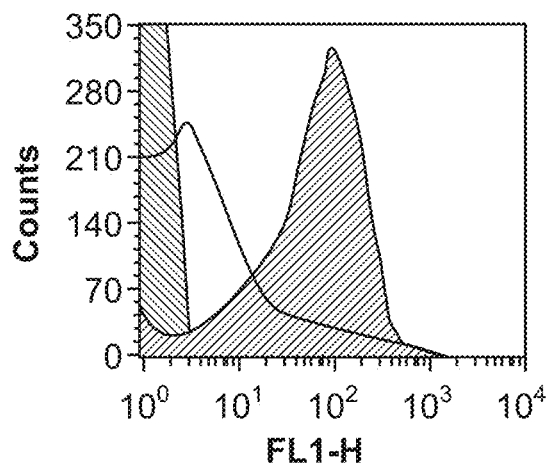

FIGS. 39A-39C depict inhibition of binding of fH by anti-fHbp mAbs as measured by ELISA with fHbp adhered to the wells of the microtiter plate (FIG. 39A), and with live bacteria of group B strain H44/76 as measured by flow cytometry (FIGS. 39B and 39C).

Figure 40A:
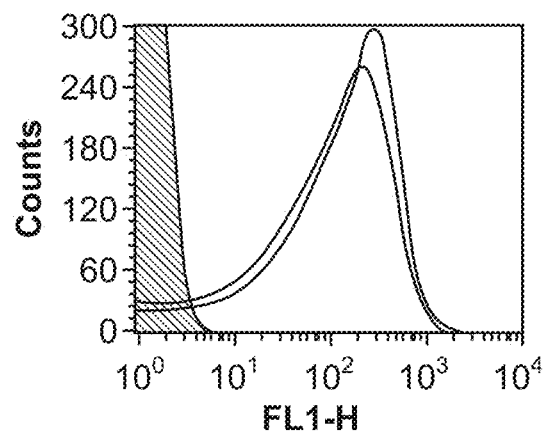
Figure 40B:
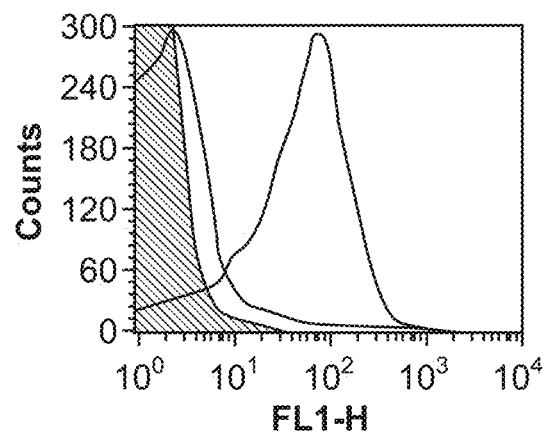
Figure 40C:
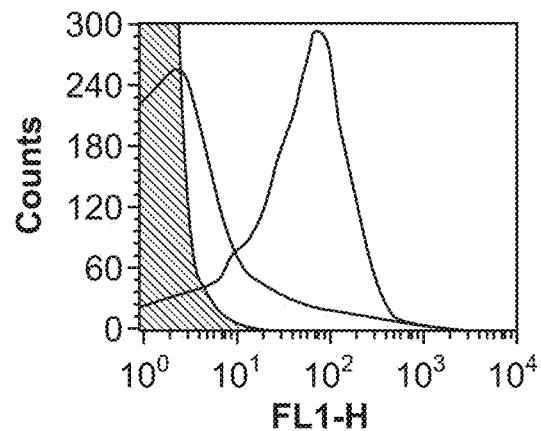

FIGS. 40A-40C depict binding of fH to mutants of group B H44/76 with genetic inactivation of fHbp expression, or both fHbp and NspA. FIG. 40A, binding of a control anti-PorA mAb; FIGS. 40B and 40C, binding of fH in human serum depleted of IgG.

FIGS. 41A-41E depict bactericidal activity of human IgG mouse chimeric anti-fHbp mAbs measured against a mutant of group B H44/76 with genetic inactivation of NspA. FIGS. 41A, 41B, and 41C: anti-fHbp mAbs JAR 3, JAR 5 and mAb 502, respectively; FIGS. 41D and 41E: control anti-PorA and anti-capsular mAbs, respectively.

Figure 42:
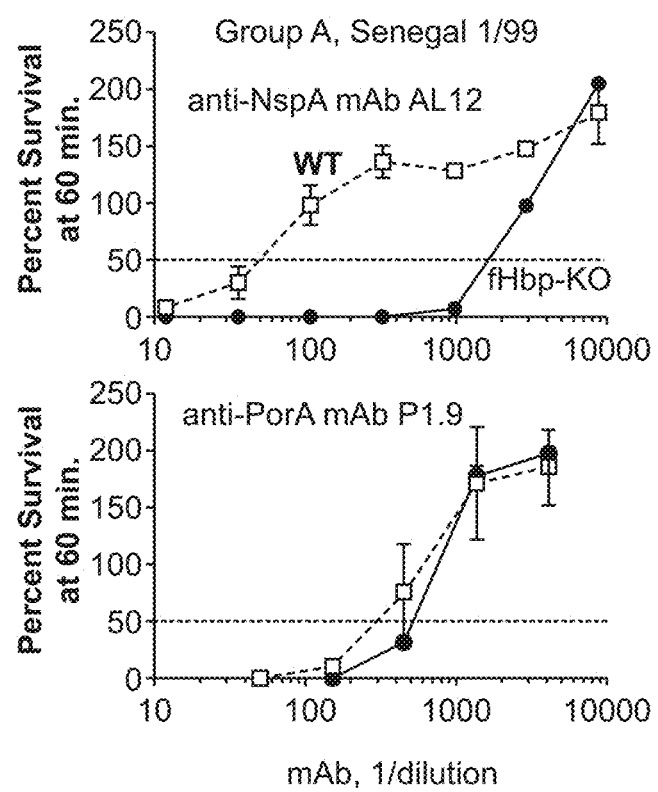

FIG. 42 depicts bactericidal activity against a capsular group A strain (Senegal 1/99) of an anti-NspA antibody against a fHbp knockout of a group A strain (top panel) or control anti-PorA mAb P1.9 (lower panel).

Figure 43:
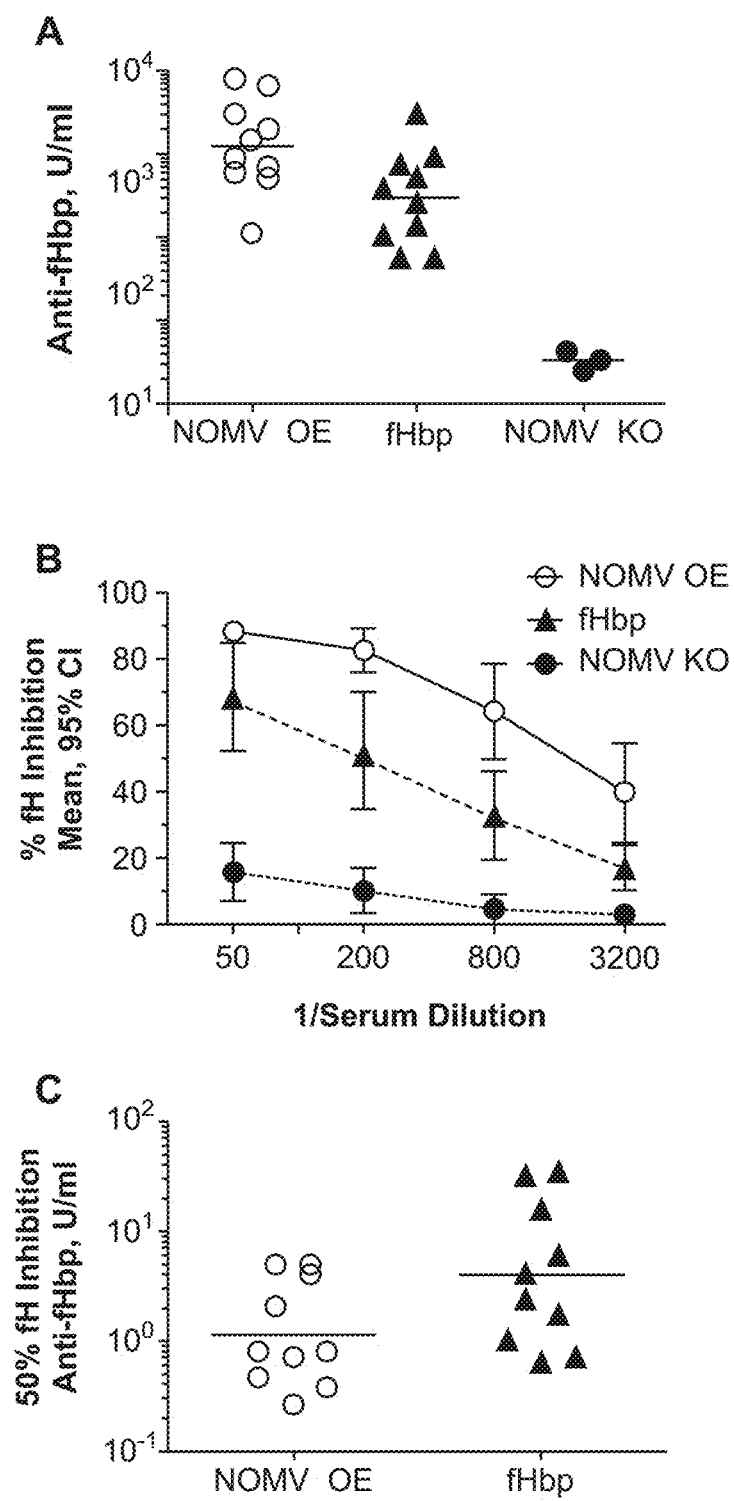

FIG. 43, Panels A-C, depicts serum anti-fHbp antibody responses of wildtype mice immunized with recombinant fHbp vaccine or native outer membrane vesicle vaccines from mutants of group B strain H44/76 with over-expressed fHbp or fHbp knockout. Anti-fHbp antibody responses to vaccination as measured by ELISA (Panel A), or the ability of serum anti-fHbp antibodies to inhibit binding of fH to fHbp (Panels B and C, also by ELISA). Mice were immunized with recombinant fHbp ID 1 vaccine (filled triangles), or NOMV vaccines prepared from mutants of group B strain H44/76 with over-expressed of fHbp ID 1 (open circles) or a fHbp knock-out (filled circles).

FIG. 44 presents an amino acid sequence of a Neisserial surface protein A (NspA) polypeptide (SEQ ID NO:15).

FIG. 45. Amino acid sequences of various naturally-occurring factor H binding proteins (fHbps): fHbp ID 1, fHbp ID 15, fHbp ID 22, fHbp ID 28, fHbp ID 77, and chimera I (Beernink et al. (2008) *Infec. Immun.* 76:2568-2575). FHbp ID sequences are shown without a leader sequence. In the sequence shown for chimera I, the lower case letters correspond to the amino acid sequence that is derived from fHbp ID 1 while the upper case letters correspond to the amino acid that is derived from ID 77.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to amino acid modifications, including amino acid substitutions, relative to a reference amino acid sequence are specifically embraced by the present invention and are disclosed herein just as if each and every combination were individually and explicitly disclosed, to the extent that such combinations embrace polypeptides having desired features, e.g., non-naturally occurring fHbp polypeptides having a lower affinity for a human fH than that of fHbp ID 1. In addition, all sub-combinations of such amino acid modifications (including amino acid substitutions) listed in the embodiments describing such amino acid modifications are also specifically embraced by the present invention and are disclosed herein just as if each and every such sub-combination of such amino acid modifications was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an antigen" includes a plurality of such antigens and reference to "the protein" includes reference to one or more proteins, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Factor H binding proteins that can elicit antibodies that are bactericidal for at least one strain of *N. meningitidis*, and methods of use such proteins, are provided.

Definitions

"Factor H Binding Protein" (fHbp), which is also known in the literature as GNA1870, GNA 1870, ORF2086, LP2086 (lipoprotein 2086), and "741" refers to a class of *N. meningitidis* polypeptides. It is found in nature as a lipoprotein on the surface of the bacterium. *N. meningitidis* strains. fHbps have been sub-divided into three fHbp variant groups (referred to as variant 1 (v.1), variant 2 (v.2), and variant 3 (v.3) in some reports (Masignani et al. (2003) *J Exp Med* 197:789-99) and Family A and B in other reports (see, e.g., Fletcher et al. (2004) *Infect Immun* 72:2088-2100)) based on amino acid sequence variability and immunologic cross-reactivity (Masignani et al. (2003) *J Exp Med* 197: 789-99). Each unique fHbp found in *N. meningitidis* is also assigned a fHbp peptide ID according to neisseria.org or pubmlst.org/neisseria/fHbp/ website. Because the length of variant 2 (v.2) fHbp protein (from strain 8047, fHbp ID 77)

and variant 3 (v.3) fHBP (from strain M1239, fHbp ID 28) differ by −1 and +7 amino acid residues, respectively, from that of MC58 (fHbp ID 1), the numbering used to refer to residues for v.2 and v.3 fHbp proteins differs from numbering based on the actual amino acid sequences of these proteins. Thus, for example, reference to a leucine residue (L) at position 166 of the v.2 or v.3 fHBP sequence refers to the residue at position 165 of the v.2 protein and at position 173 in the v.3 protein.

Human factor H ("human fH") as used herein, refers to a protein comprising an amino acid sequence as shown in FIG. 9B (SEQ ID NO:9), and naturally-occurring human allelic variants thereof.

The term "heterologous" or "chimeric" refers to two components that are defined by structures derived from different sources or progenitor sequences. For example, where "heterologous" is used in the context of a chimeric polypeptide, the chimeric polypeptide can include operably linked amino acid sequences that can be derived from different polypeptides of different phylogenic groupings (e.g., a first component from an α and a second component from a β progenitor amino acid sequences). A chimeric polypeptide containing two or more defined segments, each of which is from a different progenitor, can be naturally-occurring or man-made (non-naturally-occurring). See Beernink P T, Granoff D M (2009) *Microbiology* 155:2873-83 for more detail on naturally-occurring chimeras. Non-naturally occurring chimeras refers to "man-made chimeras" and encompass fHbp with heterologous components that are not found in nature.

A "heterologous" or "chimeric" polypeptide may also contain two or more different components, each derived from a different fHbp (e.g. variant 1, 2, or 3). The component may be operably linked at any position along the length of the fHbp polypeptide.

"Heterologous" in the context of a polynucleotide encoding any chimeric polypeptide as described above can include operably linked nucleic acid sequence that can be derived from different genes (e.g., a first component from a nucleic acid encoding a fHBP v.1 polypeptide and a second component from a nucleic acid encoding a fHBP v.2 polypeptide) or different progenitor amino acid sequences (α or β).

Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding an fHbp polypeptide or domain thereof is said to be a heterologous nucleic acid.

"Heterologous" in the context of recombinant cells can refer to the presence of a nucleic acid (or gene product, such as a polypeptide) that is of a different genetic origin than the host cell in which it is present. For example, a Neisserial amino acid or nucleic acid sequence of one strain is heterologous to a Neisserial host of another strain.

"Derived from" in the context of an amino acid sequence or polynucleotide sequence (e.g., an amino acid sequence "derived from" fHbp ID 1) is meant to indicate that the polypeptide or nucleic acid has a sequence that is based on that of a reference polypeptide or nucleic acid (e.g., a naturally occurring fHbp protein or encoding nucleic acid), and is not meant to be limiting as to the source or method in which the protein or nucleic acid is made. Non-limiting examples of reference polypeptides and reference polynucleotides from which an amino acid sequence or polynucleotide sequence may be "derived from" include a naturally-occurring fHbp, fHbp ID1, and a non-naturally-occurring fHbp. "Derived from" in the context of bacterial strains is meant to indicate that a strain was obtained through passage in vivo, or in in vitro culture, of a parental strain and/or is a recombinant cell obtained by modification of a parental strain.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Guidance for such substitutions can be drawn from alignments of amino acid sequences of polypeptides presenting the epitope of interest.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease. Protective immunity can be accompanied by production of bactericidal antibodies. It should be noted that production of bactericidal antibodies against *Neisseria meningitidis* is accepted in the field as predictive of a vaccine's protective effect in humans. (Goldschneider et al. (1969) *J. Exp. Med.* 129:1307; Borrow et al. (2001) *Infect Immun.* 69:1568).

The phrase "a disease caused by a strain of *Neisseria meningitidis*" encompasses any clinical symptom or combination of clinical symptoms that are present in an infection of a human with a *Neisseria meningitidis*. These symptoms include but are not limited to: colonization of the upper respiratory tract (e.g. mucosa of the nasopharynx and tonsils) by a pathogenic strain of *Neisseria meningitidis*, penetration of the bacteria into the mucosa and the submucosal vascular bed, septicemia, septic shock, inflammation, haemorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "specifically binds to an antibody" or "specifically immunoreactive with", in the context of an antigen (e.g., a polypeptide antigen) refers to a binding reaction which is based on and/or is probative of the presence of the antigen in a sample which may also include a heterogeneous population of other molecules. Thus, under designated conditions, the specified antibody or antibodies bind(s) to a particular antigen or antigens in a sample and do not bind in a significant amount to other molecules present in the sample. "Specifically binds to an antibody" or "specifically immunoreactive with" in the context of an epitope of an antigen (e.g., an epitope of a polypeptide) refers to a binding reaction which is based on and/or is probative of the presence of the epitope in an antigen (e.g., polypeptide) which may also include a heterogeneous population of other epitopes, as well as a heterogeneous population of antigens. Thus, under designated conditions, the specified antibody or antibodies bind(s) to a particular epitope of an antigen and do not bind in a significant amount to other epitopes present in the antigen and/or in the sample.

The phrase "in a sufficient amount to elicit an immune response" means that there is a detectable difference between an immune response indicator measured before and after administration of a particular antigen preparation Immune response indicators include but are not limited to: antibody titer or specificity, as detected by an assay such as enzyme-linked immunoassay (ELISA), bactericidal assay, flow cytometry, immunoprecipitation, Ouchterlony immunodiffusion; binding detection assays of, for example, spot, Western blot or antigen arrays; cytotoxicity assays, etc.

A "surface antigen" is an antigen that is present in a surface structure of Neisseria meningitidis (e.g. the outer membrane, capsule, pili, etc.).

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified.

"Enriched" means that a sample is non-naturally manipulated (e.g., by an experimentalist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, polypeptide, and the like)

A "knock-out" or "knockout" in the context of a target gene refers to an alteration in the sequence of the gene that results in a decrease of function of the target gene, e.g., such that target gene expression is undetectable or insignificant, and/or the gene product is not functional or not significantly functional. For example, a "knockout" of a gene involved in LPS synthesis indicates means that function of the gene has been substantially decreased so that the expression of the gene is not detectable or only present at insignificant levels and/or a biological activity of the gene product (e.g., an enzymatic activity) is significantly reduced relative to prior to the modification or is not detectable. "Knock-outs" encompass conditional knock-outs, where alteration of the target gene can occur upon, for example, exposure to a predefined set of conditions (e.g., temperature, osmolarity, exposure to substance that promotes target gene alteration, and the like. A "knock-in" or "knockin" of a target gene refers to a genetic alteration in a gene that that results in an increase in a function provided by the target gene.

fHbp Polypeptides with Altered FH Binding Properties

Before describing further fHbps contemplated by the present disclosure, it is helpful to describe some naturally-occurring fHbps. Unique naturally-occurring fHbps found in N. meningitidis are each assigned a fHbp peptide ID according to neisseria.org and pubmlst.org/neisseria/fHbp websites. This convention of naming fHbps will be adopted throughout the present disclosure.

For convenience and clarity, the native amino acid sequence of fHbp ID 1 (v.1 fHbp of the N. meningitidis strain MC58) is selected as a reference sequence for all naturally occurring and non-naturally occurring fHbp amino acid sequences, encompassing chimeric and/or variants of fHbps described herein. The amino acid sequence of fHbp ID 1 is shown in FIG. 45 and presented below:

fHbp ID1
(SEQ ID NO: 1)
CSSGGGGVAADIGAGLADALTAPLDHKDKGLQSLTLDQSVRKNEKLKLAA

QGAEKTYGNGDSLNTGKLKNDKVSRFDFIRQIEVDGQLITLESGEFQVYK

QSHSALTAFQTEQIQDSEHSGKMVAKRQFRIGDIAGEHTSFDKLPEGGRA

TYRGTAFGSDDAGGKLTYTIDFAAKQGNGKIEHLKSPELNVDLAAADIKP

DGKRHAVISGSVLYNQAEKGSYSLGIFGGKAQEVAGSAEVKTVNGIRHIG

LAAKQ.

In referring to an amino acid residue position in a fHbp, the position number used herein corresponds to the amino acid residue number of fHbp ID 1. See FIG. 19 for an alignment of various fHbps and the amino acid residues in each fHbp corresponding to those of fHbp ID 1. As seen in FIG. 19 and SEQ ID NO: 1, position number 1 refers to the first amino acid residue shown in fHbp ID 1, which is a cysteine. The fHbp referred to herein may sometimes contain an additional leader sequence at the N-terminus. For example, fHbp ID 1 may have a leader sequence of MNR-TAFCCLSLTTALILTA (SEQ ID NO:16) at the N-terminus. However, amino acid position number 1 in any fHbp is still defined herein as the position that corresponds to the cysteine at amino acid position 1 shown above for fHbp ID 1 in an alignment, which amino acid is the first residue after the leader sequence, if present. See FIG. 19 for details.

The present disclosure provides fHbps, compositions comprising same, and methods of use of the fHbps and compositions. A subject fHbp has a lower affinity for human fH than a corresponding reference fHbp (e.g. a fHbp that is naturally-occurring; or other reference fHbp). Because a high-affinity fHbp has a high probability to be complexed with fH, the bound fH can mask one or more epitopes on the fHbp from a host's immune system. Accordingly, fHbp that is complexed and/or bound with fH may not be as effective an immunogen as an fHbp that is not so complexed. Conversely, fHbps that have a relatively low affinity for fH, when administered as an immunogen (e.g. in a vaccine composition), can present epitopes to the immune system of an immunized host that an fHbp that has high affinity for fH does not, as such epitopes may be masked by bound fH. The subject fHbps have a low affinity for human fH and are useful in eliciting bactericidal antibodies and/or providing protective immunity against N. meningitidis. A subject fHbp is a non-naturally occurring fHbp. A non-naturally occurring fHbp is not found in nature and is made by a human and/or intentionally modified by a human A non-naturally occurring subject fHbp can be made via chemical synthesis or recombinant methods.

As used herein, "low affinity", "lower affinity", or "low fH binder" refers to fHbps that have a binding affinity for a human fH that is as low as or lower than that of fHbp ID 1. Accordingly, subject fHbps can encompass fHbp ID 14 and fHbp 15 since fHbp ID 14 and fHbp ID 15 have a lower affinity for human fH relative to fHbp ID 1.

The binding affinity of low-affinity fHbps and human fH can be no more than about 100%, no more than about 95%, no more than about 90%, no more than about 85%, more than about 80%, no more than about 75%, no more than about 70%, no more than about 65% fold, no more than about 60%, no more than about 50%, no more than about 45% or less of the affinity of high-affinity fHbp (e.g. fHbp ID 1) and human fH. For example, a subject fHbp can have an affinity for human fH that is less than about 50% of the affinity of fHbp ID 1 for human fH.

In some embodiments, the binding affinity of a subject non-naturally occurring fHbp for human fH is 85% or less of the binding affinity of a wildtype fHbp for human fH. For example, in some embodiments, the binding affinity of a subject non-naturally occurring fHbp for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of a wildtype fHbp for human fH. As an example, in some embodiments, the binding affinity of a subject non-naturally occurring fHbp for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, from about 1% to about 0.1%, or less than 0.1%, of the binding affinity of fHbp ID 1 for human fH.

For example, in some embodiments, the binding affinity of a subject mutant of fHbp ID1 (e.g., an R41S, R41A, R130A, H119A, E218A, or a E239A mutant of fHbp ID1) for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of fHbp ID1 for human fH.

As another example, in some embodiments, the binding affinity of a subject mutant of fHbp ID 4, ID 9, or ID 74 (e.g., an R41S mutant of fHbp ID4, ID9, or ID74) for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of fHbp ID4, ID9, or ID74 for human fH, or of the binding affinity of fHbp ID1 for human fH.

As another example, in some embodiments, the binding affinity of a subject mutant of fHbp ID 22 (e.g., an R80A, D211A, E218A, E248A, G236I, or T221A/H223A mutant of fHbp ID22) for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of fHbp ID 22 for human fH, or of the binding affinity of fHbp ID1 for human fH.

As another example, in some embodiments, the binding affinity of a subject mutant of fHbp ID 77 (e.g., an R41S/K113A, R41S/K119A, R41S/D121A, or a R41S/K113A/D121A mutant of fHbp ID 77) for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of fHbp ID 77 for human fH, or of the binding affinity of fHbp ID1 for human fH.

As another example, in some embodiments, the binding affinity of a subject mutant of fHbp ID 28 (e.g., an E218A mutant or fHbp ID 28; a K199A mutant of fHbp ID 28) for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of fHbp ID 28 for human fH, or of the binding affinity of fHbp ID1 for human fH.

Binding affinity can be described in terms of the dissociation constant ($K_D$). Low-affinity fHbps and human fH can have a dissociation constant ($K_D$; M) that is at least more than about 80%, at least more than about 100%, at least more than about 120%, at least more than about 140%, at least more than about 160%, at least more than about 200%, or more than $K_D$ of high affinity fHbps (e.g. fHbp ID 1) and human fH. The $K_D$ of a low-affinity fHbp can also be described as about 2× (2 times), about 3×, about 5×, about 10×, about 15×, about 20×, up to about 50 or more times the $K_D$ of fHbp ID 1. For example, a subject fHbp and human fH can have a $K_D$ that is 110% of or about 15× that of fHbp ID 1 and human fH.

As used herein, "lower affinity for human fH than a corresponding fHbp" is used to describe fHbps that have a binding affinity lower than a corresponding reference fHbp.

In many cases, the corresponding fHbp (the "reference fHbp") used to compare the binding affinities of subject fHbps is fHbp ID 1. Other corresponding fHbp that can be representative as a reference include variant 2 fHbp (e.g. fHbp ID 22 or 77), variant 3 (e.g. fHbp ID 28) (Masignani et al (2003) *J Exp Med* 197:789-99 and Pajon R et al (2010) *Vaccine* 28:2122-9), other variant 1 fHbps (e.g. fHbp ID 4, 9, or 94), a naturally-occurring chimeric, or a man-made chimeric fHbp.

The amino acid sequences of some examples of naturally-occurring fHbps and a man-made chimeric are provided below and shown in FIG. 45.

```
FHbp ID 22
                                             (SEQ ID NO: 2)
CSSGGGGVAADIGAGLADALTAPLDHKDKSLQSLTLDQSVRKNEKLKLAA

QGAEKTYGNGDSLNTGKLKNDKVSRFDFIRQIEVDGQLITLESGEFQIYK

QDHSAVVALQIEKINNPDKIDSLINQRSFLVSGLGGEHTAFNQLPSGKAE

YHGKAFSSDDPNGRLHYSIDFTKKQGYGRIEHLKTPEQNVELASAELKAD

EKSHAVILGDTRYGGEEKGTYHLALFGDRAQEIAGSATVKIREKVHEIGI

AGKQ

FHbp ID 28
                                             (SEQ ID NO: 3)
CSSGGGGSGGGGVAADIGTGLADALTAPLDHKDKGLKSLTLEDSIPQNGT

LTLSAQGAEKTFKAGDKDNSLNTGKLKNDKISRFDFVQKIEVDGQTITLA

SGEFQIYKQNHSAVVALQIEKINNPDKTDSLINQRSFLVSGLGGEHTAFN
```

-continued
```
QLPGGKAEYHGKAFSSDDPNGRLHYSIDFTKKQGYGRIEHLKTLEQNVEL

AAAELKADEKSHAVILGDTRYGSEEKGTYHLALFGDRAQEIAGSATVKIG

EKVHEIGIAGKQ

FHbp ID 77
                                          (SEQ ID NO: 4)
CSSGGGGVAADIGARLADALTAPLDHKDKSLQSLTLDQSVRKNEKLKLAA

QGAEKTYGNGDSLNTGKLKNDKVSRFDFIRQIEVDGQLITLESGEFQIYK

QDHSAVVALQIEKINNPDKIDSLINQRSFLVSGLGGEHTAFNQLPDGKAE

YHGKAFSSDDAGGKLTYTIDFAAKQGHGKIEHLKTPEQNVELAAAELKAD

EKSHAVILGDTRYGSEEKGTYHLALFGDRAQEIAGSATVKIGEKVHEIGI

AGKQ

FHbp ID 15
                                          (SEQ ID NO: 5)
CSSGGGGSGGGGVAADIGAGLADALTAPLDHKDKGLKSLTLEDSISQNGT

LTLSAQGAERTFKAGDKDNSLNTGKLKNDKISRFDFIRQIEVDGQLITLE

SGEFQVYKQSHSALTALQTEQVQDSEHSGKMVAKRQFRIGDIVGEHTSFG

KLPKDVMATYRGTAFGSDDAGGKLTYTIDFAAKQGHGKIEHLKSPELNVD

LAAADIKPDEKHHAVISGSVLYNQAEKGSYSLGIFGGQAQEVAGSAEVET

ANGIRHIGLAAKQ

FHbp ID 6
                                          (SEQ ID NO: 6)
CSSGGGGVAADIGAGLADALTAPLDHKDKGLQSLTLDQSVRKNEKLKLAA

QGAEKTYGNGDSLNTGKLKNDKVSRFDFIRQIEVNGQLITLESGEFQVYK

QSHSALTALQTEQVQDSEHSRKMVAKRQFRIGDIAGEHTSFDKLPKGDSA

TYRGTAFGSDDAGGKLTYTIDFAAKQGYGKIEHLKSPELNVDLAAAYIKP

DEKHHAVISGSVLYNQDEKGSYSLGIFGGQAQEVAGSAEVKTANGIRHIG

LAAKQ

FHbp ID 14
                                          (SEQ ID NO: 7)
CSSGGGGVAADIGAGLADALTAPLDHKDKSLQSLTLDQSVRKNEKLKLAA

QGAEKTYGNGDSLNTGKLKNDKVSRFDFIRQIEVDGQLITLESGEFQVYK

QSHSALTALQTEQEQDPEHSGKMVAKRRFKIGDIAGEHTSFDKLPKDVMA

TYRGTAFGSDDAGGKLTYTIDFAAKQGHGKIEHLKSPELNVELATAYIKP

DEKHHAVISGSVLYNQDEKGSYSLGIFGGQAQEVAGSAEVETANGIHHIG

LAAKQ

Chimera I
                                          (SEQ ID NO: 8)
cssggggvaadigagladaltapldhkdkglqsltldqsvrkneklklaa qgaektygngdslntgklkndkvsrfdfirqievdgqlitlesgefqvyk qshsaltafqteqiqdsehsgkmvakrqfrigdiaGEHTAFNQLPDGKAE

YHGKAFSSDDAGGKLTYTIDFAAKQGHGKIEHLKTPEQNVELAAAELKAD

EKSHAVILGDTRYGSEEKGTYHLALFGDRAQEIAGSATVKIGEKVHEIGI

AGKQ
```

(Beernink et al. (2008) *Infec. Immun.* 76:2568-2575). As noted in FIG. 45, the lower case letters correspond to the amino acid sequence that is derived from fHbp ID 1 while the upper case letters correspond to the amino acid that is derived from fHbp ID 77. Position corresponding to R41 in fHbp ID 1 is the bolded lower case "r".

The corresponding fHbp can be a naturally-occurring and/or non-naturally occurring (e.g. man-made chimeric) fHbp from which the subject fHbp is derived. Naturally-occurring chimeric encompass fHbp that have variable segments derived from different progenitors (α or β). Due to the variable segments, the molecular architecture has been shown to be modular and fHbp variants can be subclassified in modular groups according to different combinations of five variable segments, each derived from one of two genetic lineages, designated α- or β-types (Pajon R et al. (2010) *Vaccine* 28:2122-9; Beernink P T, Granoff D M (2009) *Microbiology* 155:2873-83). Six modular groups, designated I to VI account for >95% of all known fHbp variants (Pajon R et al. (2010) *Vaccine* 28:2122-9). See FIG. 16 for modular group architectures of naturally-occurring fHbps.

The corresponding fHbp can be a fHbp that has a high amino acid sequence identity as the subject fHbp (e.g. at least about 99%, at least about 95%, at least about 90%, at least about 85%, at least about 80%, or at least about 75% amino acid sequence identity) either in a segment (e.g. variable segment as defined in a modular architecture) or in the full-length mature protein.

Corresponding fHbps used as references to compare the binding affinities of subject fHbp can also encompass fHbps that have one or more segments of the same progenitor (α or β) in corresponding segments of the subject fHbp.

The subject fHbp can comprise an amino acid sequence having at least about 75%, at least about 80%, at least about 85%, at least about 90%, at least about 95%, at least about 98%, at least about 99%, amino acid sequence identity with a reference fHbp; and differs from the amino acid sequence of the reference fHbp by from 1 amino acid (aa) to 10 amino acids, e.g., differs from the amino acid sequence of the reference fHbp by 1 aa, 2 aa, 3 aa, 4 aa, 5 aa, 6 aa, 7 aa, 8 aa, 9 aa, or 10 aa. Thus, e.g., a subject fHbp can have at most one, at most two, at most three, at most four, up to at most 10 or more modifications (e.g. substitutions, deletions, or insertions) relative to a naturally occurring and/or non-naturally-occurring (e.g. chimeric) fHbp from which the subject fHbp is derived. The one or more amino acid alterations can decrease the affinity of the fHbp for human fH relative to a fHbp that is not altered. As noted above, fHbps from which the subject fHbp are derived encompass naturally occurring fHbps and non-naturally occurring fHbp. Non-naturally occurring fHbps can encompass man-made chimeras, such as those known in the art and described in PCT application number WO 2009/114485, disclosure of which is incorporated herein by reference.

Thus, in some embodiments, a subject fHbp comprises a single amino acid substitution relative to a reference fHbp (e.g., where the reference fHbp is a naturally-occurring fHbp (e.g. fHbp ID 1, or a man-made chimeric). In some embodiments, a subject fHbp comprises a single amino acid substitution (i.e., only one amino acid substitution) relative to a naturally-occurring fHbp (e.g., fHbp ID 6, fHbp ID 14, fHbp ID 15, fHbp ID 22, fHbp ID 28, fHbp ID 77, or another naturally-occurring fHbp). The amino acid sequences of fHbp ID 1, fHbp ID 15, fHbp ID 22, fHbp ID 28, and fHbp ID 77 are shown in FIGS. 19 and 45; amino acid sequences of fHbp ID 6 and fHbp ID 14 are provided above. In some embodiments, a subject fHbp comprises a single amino acid substitution (i.e., only one amino acid substitution) relative to fHbp ID 1. In some embodiments, a subject fHbp comprises 2, 3, 4, 5, 6, 7, 8, 9, or 10 amino acid substitutions relative to a reference fHbp. In some embodiments, a subject fHbp comprises 2, 3, 4, 5, 6, 7, 8, 9, or 10 amino acid substitutions relative to fHbp ID 1. In some embodiments, a subject fHbp comprises 2, 3, 4, 5, 6, 7, 8, 9, or 10 amino acid substitutions relative to a naturally-occurring fHbp (e.g., fHbp ID 6, fHbp ID 14, fHbp ID 15, fHbp ID 28, as shown in FIG. 19, or another naturally-occurring fHbp). In some embodiments, a subject fHbp comprises 2, 3, 4, 5, 6, 7, 8, 9, or 10 amino acid substitutions relative to the amino acid sequence of one of fHbp ID 1, fHbp ID 15, fHbp ID 22, fHbp ID 28, and fHbp ID 77.

The amino acid residue position at which an alteration is introduced can be determined by comparing the amino acid sequences of low fH binders (e.g. fHbp ID 14 and/or fHbp ID 15) with fHbps of a comparable affinity for human fH as fHbp ID 1, for example. FHbps of a comparable affinity for human fH as fHbp ID 1 or higher are referred herein as "high fH binders". Some examples of high fH binders include fHbp ID 1, fHbp ID 6, and fHbp ID 28. The low fH binders and high fH binders that share one or more progenitor segments can be compared in a sequence alignment. See FIG. 19 as an example of a sequence alignment for determining amino acid alterations that can be made to a naturally-occurring fHbp in order to arrive at the subject fHbp.

A subject fHbp variant can be derived from (e.g., can include one or more amino acid substitutions relative to) a variant 1 fHbp, a variant 2 fHbp, or a variant 3 fHbp. A subject fHbp variant can be derived from (e.g., can include one or more amino acid substitutions relative to) a modular group I fHbp, a modular group II fHbp, a modular group III fHbp, a modular group IV fHbp, a modular group V fHbp, a modular group VI fHbp, a modular group VII fHbp, a modular group VIII fHbp, a modular group IX fHbp, or a modular group X fHbp.

Amino acid substitutions compared to a reference fHbp that are likely to result in a fHbp with reduced affinity for fH include amino acid substitutions of fHbp amino acids that are contact residues for binding to fH; amino acid substitutions of fHbp amino acids that are surface exposed; amino acid substitutions of fHbp amino acids at the interface between the amino-terminal and carboxyl-terminal domains; and amino acid substitutions of fHbp amino acids that are proximal to a fH binding residue, where an amino acid that is "proximal to" an fH-binding amino acid is an amino acid that is from one to ten residues amino-terminal to or carboxyl-terminal to the fH-binding amino acid. In certain embodiments, the amino acid substitution that results in a low affinity for fH is not a fH contact residue. Certain contact residues are shown as bolded in FIG. 19.

Where a fHbp contains an amino acid substitution relative to a naturally-occurring or relative to fHbp ID1, the amino acid substitution can be conservative relative to that amino acid substitution. For example, if R41 is modified to S, making an R41S substitution, and particularly where the R41S substitution results in a reduced affinity for human fH, the present disclosure contemplates conservative amino acid substitutions relative to S, such that the amino acid substitution R41T is also contemplated.

The present disclosure provides a non-naturally occurring fHbp having an amino acid substitution at position 41 relative to fHbp ID 1, where the amino acid substitution is of a structure that disrupts interaction of fHbp with human factor H, but provides that the mutant fHbp retains immunogenicity Amino acids suitable for substitution at position 41 relative to fHbp ID1 include hydrophobic residues (e.g. Gly, Ala, Val, Leu, Ile, Pro); small polar residues (e.g. Ser, Cys, Thr, Met, Asn, Gln); small charged residues (e.g. Asp, Glu); and large hydrophobic residues (e.g. Phe, Trp).

Examples of substitutions that are predicted not to significantly disrupt interaction of fHbp with human factor H, and thus are to be avoided, include: large, charged residues (e.g. Lys).

In some embodiments, amino acid substitutions at one or more of the following residues are specifically excluded: R41, Q38, Q87, Q113, K113, K119, D121, G121, Q126, Q128, R130, D201, E202, E218, A235, E239, and K241. In some embodiments, e.g., where a subject fHbp comprises a single amino acid substitution relative to a reference fHbp (e.g., where the reference fHbp is a naturally-occurring fHbp or is fHbp ID 1), the single amino acid substitution can be at position E218 or E239.

Amino acid alterations found in the subject fHbps encompass those shown as shaded residues and/or boxed in FIG. 19 and listed below. In an example of sequence analysis, segment A ($V_A$; residues 8-73) of low binder fHbp ID 15 is compared to the $V_A$ of the same progenitor sequence in a high fH binder, fHbp ID 28. As such, $V_A$ segments from both fHbp ID 15 and fHbp ID 28 are identical in amino acid sequence except at residue positions 41 and 60. As seen in FIG. 19, fHbp 15 has S41 and R60 in $V_A$; fHbp ID 28 has P41 and K60. Based on this analysis, amino acid residue positions corresponding to 41 and 60 of fHbp ID 15 are candidate positions at which alteration can be introduced to arrive at the subject fHbp. In other words, a reference fHbp that does not have S and R at residue positions corresponding to 41 and 60 of fHbp ID 15, respectively, can be mutated to have S and/or R at positions corresponding to 41 and 60 of fHbp ID 15. The subject fHbp comprising one or more amino acid substitutions may then have lower affinity for human fH than without the substitutions (e.g. S41P, S41A, R41P, or R41A). Such fHbps are encompassed by the subject fHbps and are useful as immunogen in eliciting bactericidal antibodies in subjects in need thereof.

Additional candidate residue positions at which an amino acid alteration can be introduced are discussed in the examples below. For example, a fHbp of the present disclosure can have an amino acid substitution at one or more positions corresponding to one or more amino acid residues selected from 41, 60, 114, 113, 117, 119, 121, 128, 130, 147, 148, 149, 178, 195, 218, 239, 241, or 247 of fHbp ID 1 (e.g., based on the numbering of mature fHbp ID1. A fHbp of the present disclosure can have an amino acid substitution at one or more positions corresponding to one or more amino acid residues selected from 41, 60, 80, 113, 114, 117, 119, 121, 128, 130, 147, 148, 149, 178, 195, 199, 211, 220, 222, 236, 241, 247, or 248, based on the numbering of the mature fHbp ID 1. A fHbp of the present disclosure can have an amino acid substitution at one or more positions corresponding to one or more amino acid residues selected from 87, 109, 115, 118, 126, 138, 197, 201, 202, 203, 209, 217, 225, 235, or 245, based on the numbering of the mature fHbp ID 1. Where the corresponding fHbp is a variant 2 or variant 3 fHbp (or a respective corresponding modular group), the modification can be introduced at position 113, 119, and/or 121, or any combinations thereof. For example, a variant 2 fHbp (e.g. fHbp ID 77) may contain a substitution at one or more positions at 113, 119, and/or 121, as well as a serine substitution at position 41, or another suitable substitution at position 41 as described above. Where the corresponding fHbp is an ID 22 variant, the modification can be introduced at position 80, 211, 218, 221, 223, 236, or 248, or any combination thereof.

A variant factor H binding protein (fHbp) of the present disclosure can also have an amino acid substitution at one or more positions corresponding to one or more amino acid residues selected from 60, 114, 117, 147, 148, 149, 178, 195, or 247 of fHbp ID 1. Other positions can be identified using sequence alignment studies between low fH binders and high fH binders, similar to the one discussed above for $V_A$ of fHbp ID 15.

A variant fHbp of the present disclosure can be a variant of fHbp ID 1 and can include one, two, three, or four of the following substitutions: R41S, R41A, R130A, H119A, E218A, and E239A. As discussed above, a variant fHbp of the present disclosure can include a single amino acid substitution. A variant fHbp of the present disclosure can also include a double amino acid substitution. For example, variant fHbp of the present disclosure can include substitutions at two of R41S, R41A, R130A, H119A, E218A, and E239A.

A variant fHbp of the present disclosure can have an amino acid substitution at one or more positions corresponding to one or more amino acid residues selected from 80, 211, 218, 220, 222, 236, and 248 of fHbp ID 1. Corresponding positions in fHbp variants are readily ascertainable, e.g., from the alignments presented in FIGS. 19, 34, and 35. As non-limiting examples, a variant fHbp of the present disclosure can be a variant of fHbp ID 22 and can include one, two, three, or four of the following substitutions: R80A, D211A, E218A, T221A, H223A, G236I, and E248A. As discussed above, a variant fHbp of the present disclosure can include a single amino acid substitution. A variant fHbp of the present disclosure can also include a double amino acid substitution. For example, variant fHbp of the present disclosure can include substitutions at two of R80, D211, E218, T221, H223, G236, and E248. As one non-limiting example, a variant fHbp can include a T221A/H223A double substitution.

A variant fHbp of the present disclosure can have an amino acid substitution at one or more positions corresponding to one or more amino acid residues selected from residues 41, 113, 119, 121 of fHbp ID 77. As non-limiting examples, a variant fHbp of the present disclosure can be a variant of fHbp ID 77 and can include one, two, three, or four of the following substitutions: R41S, K113A, K119A, and D121A. As discussed above, a variant fHbp of the present disclosure can include a single amino acid substitution. A variant fHbp of the present disclosure can also include a double amino acid substitution. For example, variant fHbp of the present disclosure can include substitutions at two of R41S, K113A, K119A, and D121A. As one non-limiting example, a variant fHbp can include a R41S/K113A double substitution, a R41S/K119A double substitution, or a R41S/D121A double substitution.

A variant fHbp of the present disclosure can have an amino acid substitution at one or more positions corresponding to one or more amino acid residues selected from residues 113, 121, 199, and 218 of fHbp ID ID 28.

Where position R41 is substituted with serine in the fHbp of the present disclosure, its corresponding fHbp can belong to one of the modular groups shown in FIG. 16. For example, the corresponding fHbp may be from a modular group I where all variable segments are of the α lineage. Examples of such subject fHbps include R41S mutants of fHbp IDs 1, 4, 9, and 94. In some embodiments, the subject fHbps do not include mutants that do not have a decreased affinity for human fH relative to their corresponding fHbps. For example, the subject fHbps do not include R41S mutants of fHbp IDs 19 and 22.

Chimeric fHbps

As noted above, one or more modifications may be introduced into a naturally-occurring fHbp or a man-made fHbp (e.g. man-made chimeric fHbp). The modification can encompass a modification in one segment or one domain while the other segments and/or domains may be derived from any fHbp (e.g. a naturally-occurring fHbp of a different variant group).

In a fHbp described as having a modular architecture of $V_A$, $V_B$, $V_C$ $V_D$, and $V_E$ segments, the modification can be introduced into $V_A$ of an α lineage (e.g. R41S in $V_A$ of fHbp ID 1) while the other segments of the fHbp (e.g. $V_B$, $V_C$ $V_D$, and $V_E$) may each be independently derived from any lineage, any variant groups, or any fHbp ID. In another example, $V_A$, $V_C$, and $V_E$ segments of a subject fHbp can be derived from the α lineage (lineage 1) while $V_B$, and $V_D$ may be of a β lineage. Where the modification is a substitution of arginine at position 41 with serine, the modification is introduced into $V_A$ of an α progenitor ($V_A$α). The $V_A$ segment refers to a contiguous amino acid sequence that starts at residue position 7 and ends at residue position 73, in which the position number corresponds to those of the reference sequence, fHbp ID 1.

A fHbp of the present disclosure may contain an R41S mutation in a VAa segment containing an amino acid sequence that is at least about 90%, at least about 92%, at least about 94%, at least about 95%, at least about 96%, at least about 98%, at least about 99%, up to 100% identical to the following sequence:

V<u>A</u>ADIG<u>A</u>GLA DAL<u>T</u>APLDHK DK<u>SLQSL</u>TLD QSVR KN<u>E</u>KLK L<u>A</u>AQGAEK<u>TY</u> GNGD<u>SLN</u> TGKLKNDK<u>V</u> (SEQ ID NO:17). $V_A$α sequence is shown here with the R41S mutation bolded. A fHbp containing the modification of R41S thus has the R41S mutation in a $V_A$α segment and may have $V_B$, $V_C$ $V_D$, and $V_E$ segments, each independently derived from any other fHbp (e.g. a different lineage, a different variant group, or mutants of fHbp).

A chimeric fHbp of the present disclosure may also be described as having a modification in the N-terminal domain (fHbpN) of the fHbp while the C-terminal domain (fHbpC) may be derived from a different fHbp (e.g. a different variant group or a different lineage). "fHbpN" refers to a contiguous amino acid sequence that starts at about residue position 8 and ends at about residue position 136. "fHbpC" refers to a contiguous amino acid sequence that starts at about residue position 141 and ends at about residue position 255. Intervening sequence between fHbpN and fHbpC is a linker between the two domains. As an example, the fHbpN of a subject fHbp can contain an R41S mutation in a sequence derived from fHbp ID 1 while the fHbpC is derived from variant 2 or variant 3 fHbp (e.g. fHbp ID 77).

The corresponding chimeric fHbp may be of any known man-made chimeric, such as those described in Beernink et al. (2008) *Infec. Immun.* 76:2568-2575 and WO 2009/114485, disclosure of which is incorporated herein by reference. The chimeric containing the modification has a decreased affinity for human fH relative to the corresponding chimeric fHbp, while still maintaining epitopes important for eliciting bactericidal response, such as those found in the corresponding chimeric fHbp. fHbp epitopes that may be maintained in the modified chimeric includes those that are found in the corresponding chimeric fHbp such as those described in WO 2009/114485, disclosure of which is incorporated herein by reference. For example, a modified chimeric fHbp can contain epitopes important for eliciting bactericidal antibody response against strains containing variant 1 fHbp (e.g. epitopes in the N-terminal domain such as those defined by mAb JAR 4 and/or JAR 5) and/or against strains containing variant 2 or 3 fHbp (e.g. epitopes defined by mAb JAR 10, JAR 11, JAR 13, and/or JAR 36). For example, the R41S mutation is a modification that can be introduced into the chimeric fHbp shown in FIGS. 19 and 45 in order to decrease binding to human fH while still maintaining JAR 4 and JAR 5 epitopes.

One feature of a subject fHbp is that when administered to a host (e.g. mammals such as mice or human), the subject fHbp can elicit a bactericidal response at a level comparable or higher than the bactericidal response elicited by fHbp ID 1, or other corresponding reference (e.g. fHbp ID 4, 9, 22, 28, 74, or 77). Methods for determining levels of bactericidal response are known in the art and described in the Example section below. For example, the geometric mean bactericidal titers of mice immunized with the subject fHbp is at least about 70%, at least about 80%, at least about 85%, at least about 90%, at least about 95%, at least about 100%, at least about 110%, at least about 120%, at least about 150%, at least about 175%, at least about 200%, or more than 200%, of the geometric mean bactericidal titers of mice immunized with fHbp ID 1. In some instances, the geometric mean bactericidal titer of a mouse immunized with a subject fHbp is at least 2-fold, at least 2.5-fold, at least 5-fold, at least 10-fold, or more than 10-fold, higher than the geometric mean bactericidal titer of a control mouse immunized with fHbp ID 1.

The subject fHbps can exclude those that elicit a bactericidal response significantly lower than that elicited by fHbp ID 1. The subject fHbps can exclude fHbp that have mutations at both residue positions 218 and 239 (e.g. double mutant E218A/E239A). In some embodiments, the subject fHbps encompass only non-naturally occurring fHbps; as such, in some embodiments, a subject fHbp excludes naturally occurring fHbps.

In many cases, a subject fHbp variant maintains and presents a conformational epitope bound by bacteridal antibodies that have bactericidal activity toward one or more *Neisseria meningitidis* strains. Thus, such fHbp mutants may maintain an epitope found in a naturally-occurring fHbp, while exhibiting reduced binding to fH compared to the binding affinity for fH of a naturally-occurring fHbp. Variants that have minimal or no effect on the conformation of fHbp such that the mutant vaccine elicits bactericidal antibodies are considered good vaccine candidates. Whether a variant has an effect on the conformation of fHbp can be determined in various ways, including binding of antibodies listed in Table 9.

The fHbps of the present disclosure may have additional features, described in more detail below.

Conjugates

The subject fHbps of the present disclosure may contain one or more additional elements at the N- and/or C-terminus of the polypeptide, such as a polypeptide (e.g. having an amino acid sequence heterologous to the subject fHbp) and/or a carrier molecule. The additional heterologous amino acid sequences may be fused, e.g., to provide an N-terminal methionine or derivative thereof (e.g., pyroglutamate) as a result of expression in a bacterial host cell (e.g., *E. coli*) and/or to provide a chimeric polypeptide having a fusion partner at its N-terminus or C-terminus. Fusion partners of interest include, for example, glutathione-S-transferase (GST), maltose binding protein (MBP), His$_6$-tag, and the like, as well as leader peptides from other proteins, particularly lipoproteins. Fusion partners can provide for additional features, such as in facilitating isolation, purification, detection, immunogenicity of the subject fHbp.

Other elements that may be linked to the subject fHbp include a carrier molecule (e.g., a carrier protein, e.g. keyhole limpet hemocyanin (KLH)). Additional elements may be linked to the peptide via a linker, e.g. a flexible linker. Carriers encompass immunomodulators, a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid. Other carrier molecules that facilitate administration and/or to increase the immunogenicity in a subject to be vaccinated or treated against *N. meningitidis* are also contemplated. Carrier molecules can also facilitate delivery to a cell or tissue of interest. The additional moiety may also aid in immunogenicity or forming a complex with a component in a vaccine. The carrier molecules may act as a scaffold protein to facilitate display of the epitopes on a membrane surface (e.g. a vesicle vaccine).

In one example, the subject fHbps are modified at the N- and/or C-terminus to include a fatty acid (e.g. aliphatic carboxylic acid group). The fatty acid may be covalently linked to the fHbp via a flexible linker. An example of a fatty acid that may be used to modify an end (e.g. N-terminal end, e.g., at the N-terminus) of the subject fHbp is lauric acid. Lauric acid when covalently attached to another molecule is referred to as a lauroyl group (e.g. lauroyl sulfate). Lauric acid contains twelve carbon atoms with ten methylene groups and the formula $CH_3—(CH_2)_{10}—COOH$. Other fatty acids that may be linked to the subject peptides include caprylic acid (10 C), myristic acid (14 C), and palmitic acid (16 C). For details, see Westerink M A et al. (1995) *Proc. Nall. Acad. Sci. USA* 92:4021-4025. It is also contemplated that any hydrophobic moiety that can serve to anchor the subject fHbp into the bacterial outer membrane is contemplated herein for conjugation to a N- and/or C-terminal end (e.g., at the N-terminus) of the fHbps of the present disclosure, where the hydrophobic moiety can be optionally conjugated to the peptide through a linker, e.g., a flexible linker, as described herein. For example, a hydrophobic pentapeptide FLLAV (SEQ ID NO:18), as described in Lowell G H et al. (1988) *J. Exp. Med.* 167:658-63.

As noted above, one way in which the fatty acid, as well as other additional elements described above, is connected to the fHbp is via a linker (e.g. lauroyl-Gly-Gly). Linkers suitable for use in modifying the fHbp of the present disclosure include "flexible linkers". Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Examples of flexible linkers include glycine polymers $(G)_n$, glycine-serine polymers (including, for example, $(GS)_n$, GSGGS$_n$ (SEQ ID NO:19) and GGGS$_n$ (SEQ ID NO:20), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more Ramachandran (or phi-psi) space than even alanine, and are much less restricted than residues with longer side chains (see Scheraga, Rev. Computational Chem. 11173-142 (1992)). Exemplary flexible linkers include, but are not limited GGSG (SEQ ID NO:21), GGSGG (SEQ ID NO:22), GSGSG (SEQ ID NO:23), GSGGG (SEQ ID NO:24), GGGSG (SEQ ID NO:25), GSSSG (SEQ ID NO:26), and the like. The ordinarily skilled artisan will recognize that design of a fHbp conjugated to any elements described above can include linkers that are all or partially flexible, such that the linker can include a flexible linker as well as one or more portions that confer less flexible structure.

Native fHbp usually contains an N-terminal cysteine to which a lipid moiety can be covalently attached. This cysteine residue is usually lipidated in the naturally-occurring protein, and can be lipidated in the subject fHbps disclosed herein. Thus, in the amino acid sequences described herein, reference to "cysteine" or "C" at this position specifically includes reference to both an unmodified cysteine as well as to a cysteine that is lipidated (e.g., due to post-translational modification). Thus, the subject fHbp can be lipidated or non-lipidated. Methods for production of lipidated proteins in vitro, (see, e.g., Andersson et al. (2001) *J. Immunological Methods* 255:135-48) or in vivo are known in the art. For example, lipidated fHbp previously has been purified from the membrane fraction of *E. coli* protein by detergent extraction (Fletcher et al. (2004) *Infection and Immunity* 72:2088-100), which method may be adapted for the production of lipidated fHbp. Lipidated proteins may be of interest as such can be more immunogenic than soluble protein (see, e.g., Fletcher et al. (2004) *Infection and Immunity* 72:2088-100).

It will be appreciated that the nucleotide sequences encoding heterologous fHbps can be modified so as to optimize the codon usage to facilitate expression in a host cell of interest (e.g., *E. coli*, *N. meningitidis*, human (as in the case of a DNA-based vaccine), and the like). Methods for production of codon optimized sequences are known in the art.

Nucleic Acids Encoding fHbp

The present disclosure provides a nucleic acid encoding a subject fHbp. A subject nucleic acid will in some embodiments be present in a recombinant expression construct. Also provided are genetically modified host cells comprising a subject nucleic acid.

fHbp polypeptides, and encoding nucleic acids of the present disclosure can be derived from any suitable *N. meningitidis* strain. As is known in the art, *N. meningitidis* strains are divided into serologic groups (capsular groups), serotypes (PorB phenotypes) and subtypes (PorA phenotypes) on the basis of reactions with polyclonal (Frasch, C. E. and Chapman, 1973, *J. Infect. Dis.* 127: 149-154) or monoclonal antibodies that interact with different surface antigens. Capsular grouping traditionally has been based on immunologically detectable variations in the capsular polysaccharide but is being replaced by PCR of genes encoding specific enzymes responsible for the biosynthesis of the structurally different capsular polysaccharides. About 12 capsular groups (including A, B, C, X, Y, Z, 29-E, and W-135) are known. Strains of the capsular groups A, B, C, Y and W-135 account for nearly all meningococcal disease. Serotyping traditionally has been based on monoclonal antibody defined antigenic differences in an outer membrane protein called Porin B (PorB). Antibodies defining about 21 serotypes are currently known (Sacchi et al., 1998, *Clin. Diag. Lab. Immunol.* 5:348). Serosubtyping has been based on antibody defined antigenic variations on an outer membrane protein called Porin A (PorA). Both serotyping and serosubtyping are being replaced by PCR and/or DNA sequencing for identification of genes encoding the variable regions of PorB and PorA, respectively that are associated with mAb reactivity (e.g. Sacchi, Lemos et al., supra; Urwin et al., 1998, *Epidem. and Infect.* 120:257).

While *N. meningitidis* strains of any capsular group may be used, *N. meningitidis* strains of capsular group B can be sources from which nucleic acid encoding fHbp and domains thereof are derived.

Nucleic acids encoding fHbp polypeptides for use in construction of the subject fHbps contemplated herein are known in the art. Various fHbp and their sequences are available at neisseria.org and pubmlst.org/neisseria/fHbp websites. Examples of fHbp polypeptides are also described in, for example, U.S. patent application No. 61/174,424, PCT application number PCT/US09/36577, WO 2004/048404; Masignani et al. (2003) *J Exp Med* 197:789-799; Fletcher et al. (2004) *Infect Immun* 72:2088-2100; Welsch et al. J Immunol 2004 172:5606-5615; and WO 99/57280. Nucleic acid (and amino acid sequences) for fHbp variants and subvariants are also provided in GenBank as accession nos.: NC_003112, GeneID: 904318 (NCBI Ref. NP_274866), fHbp ID 1 from *N. meningitidis* strain MC58; AY548371 (AAT01290.1) (from *N. meningitidis* strain CU385); AY548370 (AAT01289.1) (from *N. meningitidis* strain H44/76); AY548377 (AAS56920.1) fHbp ID 4 from *N. meningitidis* strain M4105; AY548376 (AAS56919.1) (from *N. meningitidis* strain M1390); AY548375 (AAS56918.1) (from *N. meningitidis* strain NZ98/254); AY548374 (AAS56917.1) (from *N. meningitidis* strain M6190); AY548373 (AAS56916.1) (from *N. meningitidis* strain 4243); and AY548372 (AAS56915.1) (from *N. meningitidis* strain BZ83).

For purposes of identifying relevant amino acid sequences contemplated for use in the subject fHbps disclosed herein, it should be noted that the immature fHbp includes a leader sequence of about 19 residues. Furthermore, when provided an amino acid sequence the ordinarily skilled person can readily envision the sequences of nucleic that can encode for, and provide for expression of, a polypeptide having such an amino acid sequence.

In addition to the specific amino acid sequences and nucleic acid sequences provided herein, the disclosure also contemplates polypeptides and nucleic acids having sequences that are at least 80%, at least 85%, at least 90%, or at least 95% identical in sequence to such examples of amino acid and nucleic acids. The terms "identical" or percent "identity," in the context of two or more polynucleotide sequences, or two or more amino acid sequences, refers to two or more sequences or subsequences that are the same or have a specified percentage of amino acid residues or nucleotides that are the same (e.g., at least 80%, at least 85%, at least 90%, or at least 95% identical over a specified region), when compared and aligned for maximum correspondence over a designated region, e.g., a $Y_E$ or a region of at least about 40, 45, 50, 55, 60, 65 or more amino acids or nucleotides in length, and can be up to the full-length of the reference amino acid or nucleotide sequence (e.g., a full-length fHbp). The disclosure specifically contemplates both naturally-occurring polymorphisms and synthetically produced amino acid sequences and their encoding nucleic acids.

For sequence comparison, typically one sequence acts as a reference sequence (e.g., a naturally-occurring fHbp polypeptide sequence or a segment thereof), to which test sequences are compared. When using a sequence comparison algorithm, test and reference sequences are input into a computer program, sequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (www.ncbi.nlm.nih.gov). Further exemplary algorithms include ClustalW (Higgins D., et al. (1994) Nucleic Acids Res 22: 4673-4680), available at www.ebi.ac.uk/Tools/clustalw/index.html.

Some residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is aspartate and glutamate; a group of amino acids having basic side chains is lysine, arginine, and histidine; and a group of amino acids having sulfur-containing side chains is cysteine and methionine.

Sequence identity between two nucleic acids can also be described in terms of hybridization of two molecules to each other under stringent conditions. The hybridization conditions are selected following standard methods in the art (see, for example, Sambrook, et al., Molecular Cloning: A Laboratory Manual, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

Methods of Production

The fHbps of the present disclosure can be produced by any suitable method, including recombinant and non-recombinant methods (e.g., chemical synthesis). Where the subject fHbp is produced using recombinant techniques, the methods can involve any suitable construct and any suitable host cell, which can be a prokaryotic or eukaryotic cell, usually a bacterial or yeast host cell, more usually a bacterial cell. Methods for introduction of genetic material into host cells include, for example, transformation, electroporation, conjugation, calcium phosphate methods and the like. The method for transfer can be selected so as to provide for stable expression of the introduced fHbp-encoding nucleic acid. The fHbp-encoding nucleic acid can be provided as an inheritable episomal element (e.g., plasmid) or can be genomically integrated.

Suitable vectors for transferring fHbp-encoding nucleic acid can vary in composition. Integrative vectors can be conditionally replicative or suicide plasmids, bacteriophages, and the like. The constructs can include various elements, including for example, promoters, selectable genetic markers (e.g., genes conferring resistance to antibiotics (for instance kanamycin, erythromycin, chloramphenicol, or gentamycin)), origin of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

In one example, the vector is an expression vector based on episomal plasmids containing selectable drug resistance markers and elements that provide for autonomous replication in different host cells (e.g., in both *E. coli* and *N. meningitidis*). One example of such a "shuttle vector" is the plasmid pFP10 (Pagotto et al. (2000) *Gene* 244:13-19).

Constructs can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding the subject fHbp, may provide for propagating the subject nucleic acids, or both.

Examples of vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. pET21 is also an expression vector that may be used. Bacteriophage vectors may include λgt10, λgt11, λgt18-23, λZAP/R and the EMBL series of bacteriophage vectors. Further vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

For expression of a subject fHbp, an expression cassette may be employed. Thus, the present disclosure provides a recombinant expression vector comprising a subject nucleic acid. The expression vector provides transcriptional and translational regulatory sequences, and may provide for inducible or constitutive expression, where the coding region is operably linked under the transcriptional control of the transcriptional initiation region, and a transcriptional and translational termination region. These control regions may be native to an fHbp from which the subject fHbp is derived, or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

It should be noted that fHbps of the present disclosure may comprise additional elements, such as a detectable label, e.g., a radioactive label, a fluorescent label, a biotin label, an immunologically detectable label (e.g., an HA tag, a poly-Histidine tag) and the like. Additional elements of fHbp can be provided to facilitate isolation (e.g., biotin tag, immunologically detectable tag) through various methods (e.g., affinity capture, etc.). The subject fHbp can optionally be immobilized on a support through covalent or non-covalent attachment.

Isolation and purification of fHbp can be accomplished according to methods known in the art. For example, fHbp can be isolated from a lysate of cells genetically modified to express a fHbp, or from a synthetic reaction mix, by immunoaffinity purification, which generally involves contacting the sample with an anti-fHbp antibody (e.g., an anti-fHbp mAb, such as a JAR 5 MAb or other appropriate JAR MAb known in the art), washing to remove non-specifically bound material, and eluting specifically bound fHbp. Isolated fHbp can be further purified by dialysis and other methods normally employed in protein purification methods. In one example, the fHbp can be isolated using metal chelate chromatography methods.

Host Cells

Any of a number of suitable host cells can be used in the production of fHbp. In general, the fHbp described herein may be expressed in prokaryotes or eukaryotes, usually bacteria, more usually *E. coli* or *Neisseria* (e.g., *N. meningitidis*) in accordance with conventional techniques. Thus, the present disclosure further provides a genetically modified host cell, which contains a nucleic acid encoding a subject fHbp. Host cells for production (including large scale production) of a subject fHbp can be selected from any of a variety of available host cells. Examples of host cells for expression include those of a prokaryotic or eukaryotic unicellular organism, such as bacteria (e.g., *Escherichia coli* strains), yeast (e.g., *S. cerevisiae, Pichia* spp., and the like), and may include host cells originally derived from a higher organism such as insects, vertebrates, particularly mammals, (e.g. CHO, HEK, and the like). Generally bacterial host cells and yeast are of particular interest for subject fHbp production.

Subject fHbps can be prepared in substantially pure or substantially isolated form (i.e., substantially free from other Neisserial or host cell polypeptides) or substantially isolated form. The subject fHbp can be present in a composition that is enriched for the polypeptide relative to other components that may be present (e.g., other polypeptides or other host cell components). Purified subject fHbp can be provided such that the polypeptide is present in a composition that is substantially free of other expressed polypeptides, e.g., less than 90%, usually less than 60% and more usually less than 50% of the composition is made up of other expressed polypeptides.

Host Cells for Vesicle Production

Where a subject fHbp is to be provided in a membrane vesicle (as discussed in more detail below), a Neisserial host cell is genetically modified to express a subject fHbp. Any of a variety of *Neisseria* spp. strains can be modified to produce a subject fHbp, and, optionally, which produce or can be modified to produce other antigens of interest, such as PorA, can be used in the methods disclosed herein.

Methods and vectors to provide for genetic modification of Neisserial strains and expression of a desired polypeptide are known in the art. Examples of vectors and methods can be found in WO 02/09746 and O'Dwyer et al. (2004) *Infect Immun* 72:6511-80. Strong promoters, particularly constitutive strong promoters are of particular interest. Examples of promoters include the promoters of porA, porB, lbpB, tbpB, p110, hpuAB, lgtF, opa, p110, lst, hpuAB, and rmp.

Pathogenic *Neisseria* spp. or strains derived from pathogenic *Neisseria* spp., particularly strains pathogenic for humans or derived from strains pathogenic or commensal for humans, are of particular interest for use in membrane vesicle production. Examples of Neisserial spp. include *N. meningitidis, N. flavescens, N. gonorrhoeae, N. lactamica, N. polysaccharea, N. cinerea, N. mucosa, N. subflava, N. sicca, N. elongata*, and the like.

*N. meningitidis* strains are of particular interest for genetic modification to express the subject fHbps and for use in vesicle production. The strain used for vesicle production can be selected according to a number of different characteristics that may be desired. For example, the strain may be selected according to: a desired PorA type (a "serosubtype", as described above), capsular group, serotype, and the like; decreased capsular polysaccharide production; and the like. For example, the production strain can produce any desired PorA polypeptide, and may express one or more PorA polypeptides (either naturally or due to genetic engineering). Examples of strains include those that produce a PorA polypeptide which confers a serosubtype of P1.7,16; P1.19, 15; P1.7,1; P1.5,2; P1.22a,14; P1.14; P1.5,10; P1.7,4; P1.12, 13; as well as variants of such PorA polypeptides which may or may not retain reactivity with conventional serologic reagents used in serosubtyping. Also of interest are PorA polypeptides characterized according to PorA variable region (VR) typing (see, e.g., Russell et al. (2004) *Emerging Infect Dis* 10:674-678; Sacchi C T et al. (1998) *Clin Diagn Lab Immunol* 5:845-55; Sacchi et al (2000) *J. Infect Dis* 182:1169-1176). A substantial number of distinct VR types have been identified, which can be classified into VR1 and VR2 family "prototypes". A web-accessible database describing this nomenclature and its relationship to previous typing schemes is found at neisseria.org/nm/typing/pora. Alignments of certain PorA VR1 and VR2 types are provided in Russell et al. (2004) *Emerging Infect Dis* 10:674-678.

Alternatively or in addition, the production strain can be a capsule deficient strain. Capsule deficient strains can provide vesicle-based vaccines that provide for a reduced risk of eliciting a significant autoantibody response in a subject to whom the vaccine is administered (e.g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell enzyme-linked immunosorbent assay (ELISA) using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. (2003) *J. Infect. Dis.* 187:1616-28), as well as methods of identifying and/or generating capsule-deficient strains (see, e.g., Fisseha et al. (2005) *Infect. Immun.* 73:4070-4080; Stephens et al. (1991) *Infect Immun* 59:4097-102; Frosch et al. (1990) *Mol Microbiol.* 4:1215-1218) are known in the art.

Modification of a Neisserial host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes.

Of particular interest are strains that are deficient in sialic acid biosynthesis. Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetylglucosamine -6-phosphate 2-epimerase gene (known as synX AAF40537.1 or siaA AAA20475), with strains having this gene inactivated being of especial interest. For example, in one embodiment, a capsule deficient strain is generated by disrupting production of a functional synX gene product (see, e.g., Swartley et al. (1994) *J Bacteriol.* 176:1530-4).

Capsule-deficient strains can also be generated from naturally-occurring strains using non-recombinant techniques, e.g., by use of bactericidal anti-capsular antibodies to select for strains with reduced levels of capsular polysaccharide.

Where the disclosure involves use of two or more strains (e.g., to produce antigenic compositions containing a subject fHbp-presenting vesicles from different strains), the strains can be selected so as to differ in one or more strain characteristics, e.g., to provide for vesicles that differ in the subject fHbp used, PorA, and the like.

Preparation of Vesicles

The antigenic compositions contemplated by the present disclosure generally include vesicles prepared from Neisserial cells that express a subject fHbp. As referred to herein "vesicles" is meant to encompass outer membrane vesicles as well as microvesicles (which are also referred to as blebs).

The antigenic composition can contain outer membrane vesicles (OMV) prepared from the outer membrane of a cultured strain of *Neisseria meningitidis* spp. genetically modified to express a subject fHbp. OMVs may be obtained from *Neisseria meningitidis* grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

The antigenic composition can contain microvesicles (MV) (or "blebs") containing subject fHbps, where the MV or blebs are released during culture of a *Neisseria meningitidis* strain genetically modified to express a subject fHbp. For example, MVs may be obtained by culturing a strain of *Neisseria meningitidis* in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An exemplary strain that produces high levels of blebs is described in PCT Publication No. WO 01/34642. In addition to bleb production, strains for use in MV production may also be selected on the basis of NspA production, where strains that produce higher levels of NspA may be of particular interest (for examples of *N. meningitidis* strains having different NspA production levels, see, e.g., Moe et al. (1999 Infect. Immun 67: 5664). Other strains of interest for use in production of blebs include strains having an inactivated GNA33 gene, which encodes a lipoprotein required for cell separation, membrane architecture and virulence (see, e.g., Adu-Bobie et al. (2004) *Infect Immun.* 72:1914-1919).

The antigenic compositions of the present disclosure can contain vesicles from one strain, or from 2, 3, 4, 5 or more strains, which strains may be homologous or heterologous, usually heterologous, to one another. For example, the strains may be homologous or heterologous with respect to PorA and/or the fHbp from which the subject fHbp is derived. The vesicles can be prepared from strains that express more than one subject fHbp (e.g., 1, 2, 3, or more subject fHbp) which may be composed of fHbp amino acid sequences from different variants (v.1, v.2, or v.3) or subvariants (e.g., a subvariant of v.1, v.2, or v.3).

The antigenic compositions can comprise a mixture of OMVs and MVs presenting the same or different subject fHbps, where the subject fHbps may optionally present epitopes from different combinations of fHbp variants and/or subvariants and where the OMVs and/or MVs may be from the same or different strains. Vesicles from different strains can be administered as a mixture, or can be administered serially.

Where desired (e.g., where the strains used to produce vesicles are associated with endotoxin or particular high levels of endotoxin), the vesicles are optionally treated to reduce endotoxin, e.g., to reduce toxicity following administration. Although less desirable as discussed below, reduction of endotoxin can be accomplished by extraction with a suitable detergent (for example, BRIJ-96, sodium deoxycholate, sodium lauroylsarcosinate, Empigen BB, TRITON X-100, TWEEN 20 (sorbitan monolaurate polyoxyethylene), TWEEN 80, at a concentration of 0.1-10%, preferably 0.5-2%, and SDS). Where detergent extraction is used, it is preferable to use a detergent other than deoxycholate.

The vesicles of the antigenic compositions can be prepared without detergent, e.g., without use of deoxycholate. Although detergent treatment is useful to remove endotoxin activity, it may deplete the native fHbp lipoprotein and/or subject fHbp (including lipidated fHbp) by extraction during vesicle production. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from Neisseria mutants in which lipooligosaccharide or other antigens that may be undesirable in a vaccine (e.g. Rmp) is reduced or eliminated.

Vesicles can be prepared from N. meningitidis strains that contain genetic modifications that result in decreased or no detectable toxic activity of lipid A. For example, such strain can be genetically modified in lipid A biosynthesis (Steeghs et al. (1999) Infect Immun 67:4988-93; van der Ley et al. (2001) Infect Immun 69:5981-90; Steeghs et al. (2004) J Endotoxin Res 10:113-9; Fissha et al, (2005) Infect Immun 73:4070). The immunogenic compositions may be detoxified by modification of LPS, such as downregulation and/or inactivation of the enzymes encoded by lpxL1 or lpxL2, respectively. Production of a penta-acylated lipid A made in lpxL1 mutants indicates that the enzyme encoded by lpxL1 adds the C12 to the N-linked 3-OH C14 at the 2' position of GlcN II. The major lipid A species found in lpxL2 mutants is tetra-acylated, indicating the enzyme encoded by lpxL2 adds the other C12, i.e., to the N-linked 3-OH C14 at the 2 position of GlcN I. Mutations resulting in a decreased (or no) expression of these genes (or decreased or no activity of the products of these genes) result in altered toxic activity of lipid A (van der Ley et al. (2001) Infect Immun 69:5981-90). Tetra-acylated (lpxL2 mutant) and penta acylated (lpxL1 mutant) lipid A are less toxic than the wild-type lipid A. Mutations in the lipid A 4'-kinase encoding gene (lpxK) also decrease the toxic activity of lipid A. Of particular interest for use in production of vesicles (e.g., MV or OMV) are N. meningitidis strains genetically modified so as to provide for decreased or no detectable functional LpxL1-encoded protein, e.g., where the Neisseria bacterium (e.g., N. meningitidis strain) is genetically modified to provide for decreased or no activity of a gene product of the lpxL1 gene. For example, the Neisseria bacterium can be genetically modified to have an lpxL1 gene knockout, e.g., where the lpxL1 gene is disrupted. See, e.g., US Patent Publication No. 2009/0035328. The Neisseria bacterium can be genetically modified to provide for decreased or no activity of a gene product of the lpxL2 gene. The Neisseria bacterium can be genetically modified to provide for decreased or no activity of a gene product of the lpxL1 gene and the lpxL2 gene. Such vesicles provide for reduced toxicity as compared to N. meningitidis strains that are wild-type for LPS production, while retaining immunogenicity of subject fHbp.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoPc), or low Mg++ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF secretion from human monocytes.

Polymyxin B resistant strains are also suitable for use, as such strains have been shown to have reduced LPS toxicity (see, e.g., van der Ley et al. (1994) In: Proceedings of the ninth international pathogenic Neisseria conference. The Guildhall, Winchester, England). Alternatively, synthetic peptides that mimic the binding activity of polymyxin B may be added to the antigenic compositions to reduce LPS toxic activity (see, e.g., Rustici et al. (1993) Science 259: 361-365; Porro et al. (1998) Prog Clin Biol Res. 397:315-25).

Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

Compositions and Formulations

"Compositions", "antigen composition", "antigenic composition" or "immunogenic composition" is used herein as a matter of convenience to refer generically to compositions comprising a subject fHbp as disclosed herein, which subject fHbp may be optionally conjugated to further enhance immunogenicity. Compositions useful for eliciting antibodies, e.g., antibodies against Neisseria meningitidis, e.g., bactericidal antibodies to Neisseria meningitidis, in a human are specifically contemplated by the present disclosure. Antigenic compositions can contain 1, 2, or more different subject fHbps. Where there is more than one type of fHbp, each subject fHbps may present epitopes from different combinations of fHbp variants and/or subvariants.

Antigenic compositions contain an immunologically effective amount of a subject fHbp, and may further include other compatible components, as needed. Compositions of the present disclosure can contain fHbp that are low fH binders. Low fH binders in the subject compositions encompass any fHbp described above, such as non-naturally-occurring or naturally-occurring fHbp (e.g. fHbp ID 14 and/or fHbp ID 15). The composition contain one or more fHbp, in which at least one fHbp is a low fH binder. Where there is more than one fHbp in a composition, each fHbp may be different (e.g. in amino acid sequences and/or conjugation).

Immunogenic compositions contemplated by the present disclosure include, but are not limited to, compositions comprising:

1) a non-naturally occurring fHbp (e.g., a non-naturally occurring fHbp that has lower affinity for human fH than fHbp ID 1); and 2) a fHbp (e.g., a non-naturally occurring fHbp, e.g., a non-naturally occurring fHbp that has a lower affinity for fH than fHbp ID 1) and NspA;

where the fHbp and/or NspA can be provided as recombinant proteins and/or in a vesicle-based composition (e.g., OMV). It should be noted that where the composition includes both NspA and a fHbp, the bactericidal activity of antibodies elicited by administration of the composition can result from cooperation of antibodies to one or both antigens. Examples of immunogenic compositions provided by the present disclosure include:

a) an immunogenic composition that comprises a non-naturally occurring fHbp variant as described above (e.g., a, where the non-naturally occurring fHbp elicits a bactericidal antibody response to at least one Neisseria meningitidis strain);

b) an immunogenic composition that comprises a non-naturally occurring fHbp variant as described above (e.g., a non-naturally occurring fHbp that has lower affinity for human fH than fHbp ID 1); and a recombinant NspA protein;

c) an immunogenic composition that comprises an isolated fHbp comprising at least 85% amino acid sequence identity to fHbp ID 14 or fHbp ID 15, where the fHbp has lower affinity for human factor H (fH) than fHbp ID 1;

d) an immunogenic composition that comprises an isolated fHbp comprising at least 85% amino acid sequence identity to fHbp ID 14 or fHbp ID 15, where the fHbp has lower affinity for human factor H (fH) than fHbp ID 1; and a recombinant NspA protein;

e) an immunogenic composition that comprises a native OMV obtained from a genetically modified Neisseria host cell that is genetically modified with a nucleic acid encoding a non-naturally occurring fHbp variant as described above (e.g., a non-naturally occurring fHbp that has lower affinity for human fH than fHbp ID 1), such that the encoded non-naturally occurring fHbp is produced by the genetically modified host cell, where the OMV comprises the encoded non-naturally occurring fHbp; and f) an immunogenic composition that comprises a native OMV obtained from a genetically modified Neisseria host cell that is genetically modified with a nucleic acid encoding a non-naturally occurring fHbp variant as described above (e.g., a non-naturally occurring fHbp that has lower affinity for human fH than fHbp ID 1, such that the encoded non-naturally occurring fHbp is produced by the genetically modified host cell, where the OMV comprises the encoded non-naturally occurring fHbp; and where the Neisseria host cell also produces higher levels of NspA, such that the OMV also comprises NspA. For example, the Neisseria host cell can be one that is genetically modified for increased expression of NspA.

By "immunologically effective amount" is meant that the administration of that amount to an individual, either in a single dose, as part of a series of the same or different antigenic compositions, is effective to elicit an antibody response effective for treatment or prevention of a symptom of, or disease caused by, for example, infection by Neisseria, particularly N. meningitidis, more particularly Group B N. meningitidis. This amount varies depending upon the health and physical condition of the individual to be treated, age, the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials.

Amino acid sequences of NspA polypeptides are known in the art. See, e.g., WO 96/29412; and Martin et al. (1997) J. Exp. Med. 185:1173; GenBank Accession No. U52066; and GenBank Accession No. AAD53286. An "NspA polypeptide" can comprise an amino acid sequence having at least about 80%, at least about 85%, at least about 90%, at least about 95%, at least about 98%, at least about 99%, or 100%, amino acid sequence identity to a contiguous stretch of from about 75 amino acids to about 100 amino acids, from about 100 amino acids to about 150 amino acids or from about 150 amino acids to about 174 amino acids, of the amino acid sequence depicted in FIG. 44. An "NspA polypeptide" can comprise an amino acid sequence having at least about 80%, at least about 85%, at least about 90%, at least about 95%, at least about 98%, at least about 99%, or 100%, amino acid sequence identity to a contiguous stretch of from about 75 amino acids to about 100 amino acids, or from about 100 amino acids to about 155 amino acids, of amino acids 20 to 174 of the amino acid sequence depicted in FIG. 44. In some cases, the NspA polypeptide lacks a signal sequence; in other cases (e.g., for expression in a host cell), the NspA polypeptide includes a signal sequence.

Dosage regimen may be a single dose schedule or a multiple dose schedule (e.g., including booster doses) with a unit dosage form of the antigenic composition administered at different times. The term "unit dosage form," as used herein, refers to physically discrete units suitable as unitary dosages for human and animal subjects, each unit containing a predetermined quantity of the antigenic compositions of the present disclosure in an amount sufficient to produce the desired effect, which compositions are provided in association with a pharmaceutically acceptable excipient (e.g., pharmaceutically acceptable diluent, carrier or vehicle). The antigenic composition may be administered in conjunction with other immunoregulatory agents.

Antigenic compositions can be provided in a pharmaceutically acceptable excipient, which can be a solution such as a sterile aqueous solution, often a saline solution, or they can be provided in powder form. Such excipients can be substantially inert, if desired.

In some embodiments, a subject immunogenic composition comprises a subject fHbp present in a vesicle. In some embodiments, a subject immunogenic composition comprises a subject fHbp present in an MV. In some embodiments, a subject immunogenic composition comprises a subject fHbp present in an OMV. In some embodiments, a subject immunogenic composition comprises a mixture of MV and OMV comprising a subject fHbp. Vesicles, such as MV and OMV, are described above.

The antigenic compositions can further contain an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN 80™, 0.5% w/v SPAN 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN 80 emulsion. The effectiveness of an adjuvant may be determined by measuring the amount of antibodies directed against the immunogenic antigen or antigenic epitope thereof.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% SPAN 85 (optionally containing MTP-PE) formulated into submicron particles using a microfluidizer, (b) SAF, containing 10% Squalane, 0.4% Tween 80, 5% PLURONIC-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80, and one or more bacterial cell wall components such as monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg Curr Opin Mol Ther 2001 3:15-24; Roman et al., Nat. Med, 1997, 3, 849-854; Weiner et al., PNAS USA, 1997, 94, 10833-10837; Davis et al, J. Immunol, 1998, 160, 810-876; Chu et al., J. Exp. Med, 1997, 186, 1623-1631; Lipford et al, Ear. J. Immunol., 1997, 27, 2340-2344; Moldoveami et al., Vaccine, 1988, 16, 1216-1224, Krieg et al., Nature, 1995, 374, 546-549; Klinman et al., PNAS USA, 1996, 93, 2879-2883; Ballas et al, J Immunol, 1996, 157, 1840-1845; Cowdery et al, J Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J Immunol, 1996, 157, 4918-4925; Yi et al, J. Immunol, 1996, 157, 5394-5402; Yi et al, J Immunol, 1998, 160, 4755-4761; and Yi et al, J Immunol, 1998, 160, 5898-5906; International patent applications WO 96/02555, WO 98/16247, WO 98/18810, WO 98/40100, WO 98/55495, WO 98/37919 and WO 98/52581, i.e. containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally+a sterol) e.g. WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero -3-hydroxyphosphoryloxy)-ethylamine MTP-PE), etc. Adjuvants suitable for administration to a human are of particular interest.

The antigen compositions may contain other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of the subject fHbp in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The fHbp-containing formulations can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The fHbp-containing formulations can also be provided so as to enhance serum half-life of fHbp following administration. For example, where isolated fHbps are formulated for injection, the fHbp may be provided in a liposome formulation, prepared as a colloid, or other conventional techniques for extending serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms.

Immunization

The present disclosure provides a method of inducing an immune response to at least one Neisserial strain in a mammalian host. The methods generally involve administering to an individual in need thereof an effective amount of a subject immunogenic composition.

The fHbp-containing antigenic compositions are generally administered to a human subject that is at risk of acquiring a Neisserial disease so as to prevent or at least partially arrest the development of disease and its complications. An amount adequate to accomplish this is defined as a "therapeutically effective dose." Amounts effective for therapeutic use will depend on, e.g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

The fHbp-containing antigenic compositions are generally administered in an amount effective to elicit an immune response, particularly a humoral immune response, e.g., a bactericidal antibody response, in the host. As noted above, amounts for immunization will vary, and can generally range from about 1 µg to 100 µg per 70 kg patient, usually 5 µg to 50 µg/70 kg. Substantially higher dosages (e.g. 10 mg to 100 mg or more) may be suitable in oral, nasal, or topical administration routes. The initial administration can be followed by booster immunization of the same of different fHbp-containing antigenic composition. Usually vaccination involves at least one booster, more usually two boosters.

In general immunization can be accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

An anti-fHbp immune response can be assessed by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like).

The antigenic compositions can be administered to a human subject that is immunologically naive with respect to *Neisseria meningitidis*. In a particular embodiment, the subject is a human child about five years or younger, and preferably about two years old or younger, and the antigenic compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

It may be generally desirable to initiate immunization prior to the first sign of disease symptoms, or at the first sign of possible or actual exposure to infection or disease (e.g., due to exposure or infection by *Neisseria*).

Methods of Screening

In one example, a method of evaluating the efficacy of a subject fHbp in a vaccine composition involves: (a) immunizing a host animal (e.g., a non-human mammalian host animal, such as a rodent, e.g., a mouse) with a composition comprising a fHbp of the present disclosure; and (b) measuring levels of bactericidal antibodies in the host. The subject method may also include assessing the susceptibility of a host animal administered with a vaccine comprising a subject fHbp to a bacterial pathogen.

In another example, the method can involve making and identifying antibodies elicited by the subject fHbp. The method involves isolating antibodies from the host animal that have binding affinity to the fHbp, contacting a bacterial cell with the isolated antibodies; and assessing binding of the antibody to the bacterial cell. Additional steps may include assessing the competitive binding of the antibody to fHbp with human factor H; assessing the bactericidal activity against a bacterial pathogen when the antibody is administered to an animal contracted with the bacterial pathogen. In some embodiments, the antibody is in an antibody population, and the method can further comprise: isolating one or more antibodies of the antibody population that bind the bacterial cell. A featured aspect is isolated antibody that is bactericidal against the bacterial cell, which may include, for example, complement-mediated bactericidal activity and/or opsonophagocytic activity capable of decreasing the viability of the bacteria in human blood.

Bacterial pathogens of particular interest are *N. meningitidis* of any or all variant groups, of diverse capsular groups, such as *N. meningitidis* Serogroup B, *N. meningitidis* Serogroup C, *N. meningitidis* Serogroup X, *N. meningitidis* Serogroup Y, *N. meningitidis* Serogroup W-135, and the like.

Methods of Evaluating a Response to a fHbp

The present disclosure provides methods for determining the likelihood that a fHbp will elicit a bactericidal response in an individual; and methods of evaluating a variant fHbp for suitability for inclusion in an immunogenic composition.

Determining the Likelihood that a fHbp Will Elicit a Bactericidal Response

The present disclosure provides a method of determining the likelihood that a fHbp (e.g., a fHbp present in a Neisserial vaccine) will elicit a bactericidal response in an individual to at least one *Neisseria meningitidis* strain. The method generally involves determining the ability of antibody, present in serum obtained from an individual who has been immunized with a fHbp, to inhibit binding of fH to fHbp. Inhibition of binding of fH to fHbp by the antibody at a level that is at least about 10% higher, at least about 25%, at least about 50%, at least about 75%, at least about 2-fold, at least about 10-fold, at least about 50-fold, at least about 100-fold, or greater than 100-fold, than the level of inhibition of fH to fHbp by a control antibody that inhibits fH binding to fHbp but that does not generate a bactericidal response, indicates that the fHbp is likely to elicit a bactericidal response to at least one *Neisseria meningitidis* strain. In some embodiments, the fHbp is a non-naturally occurring fHbp that has lower affinity for human factor H (fH) than fHbp ID 1, as described above.

The degree of inhibition of binding of fH to fHbp by antibody elicited to a fHbp variant can be determined using an assay as described herein, or any other known assay. For example, the fH and/or the fHbp can comprise a detectable label, and inhibition of fH/fHbp binding can be assessed by detecting the amount of labelled component present in an fH/fHbp complex and/or detecting the amount of label present in free fH and/or free fHbp (e.g., fH or fHbp not in an fH/fHbp complex).

In one example, assays to assess fH binding to an fHbp involve use of fHbp immobilized on a support (e.g., fHbp immobilized on the well of a microtiter plate). A mixture of a fixed concentration of human fH with dilutions of the test antibodies (e.g., antiserum, e.g., from a human or non-human test animal (e.g., mouse) that has received an antibody-eliciting dosage of an immunogenic composition) are added to the wells and incubated for an amount of time sufficient to allow for antibody binding. After washing the wells, bound fH is detected with a specific anti-fH antiserum (e.g., goat or donkey) containing a labeled component, or a secondary labeled antibody (e.g., rabbit anti-goat or anti-donkey anti-serum). Percent inhibition of bound fH can be calculated by the amount of bound fH in the absence of added human or mouse antibody.

In another variation of such assays, binding of fH to live bacteria in the presence or absence of test antisera is assessed by flow cytometry. Bacterial cells are incubated with a fixed concentration of fH (e.g., detectably labeled fH) and different dilutions of test sera containing antibody. The bacteria are washed and bound fH is detected (e.g., as described above).

Thus, the ability of antiserum from an individual immunized with a fHbp to inhibit fH/fHbp binding serves as a surrogate for directly assessing bactericidal activity of the antiserum. A method of the present disclosure for determining the likelihood that a fHbp will elicit a bactericidal response in an individual can provide information to a clinician or other medical personnel as to whether a particular immunogenic composition has been effective in eliciting a bactericidal response in an individual.

Immunized individuals can have a similar serum IgG anti-fHbp antibody titer by ELISA. Antisera that provides for overall better inhibition of fH binding is indicative of a more effective, better quality anti-fHbp antibody response and will confer greater protection. Thus, for example, if in comparing the anti-Neisserial antibody response in two individuals (by the anti-fHbp antibodies, i.e, a serum dilution of 1:10,000 inhibits compared to a dilution of 1:3000 by the other individual) the individual with the higher inhibitory activity has better quality anti-fHbp antibody that will confer greater protection. The fH inhibition assay is thus a surrogate for complement-mediated bactericidal titer assays, which complement-mediated bactericidal titer assays are generally more time consuming and difficult to measure than fH inhibition.

Evaluating a Variant fHbp

The present disclosure provides methods of assessing or predicting the likelihood that a fHbp variant will be efficacious in eliciting a bactericidal antibody response in an individual. The methods generally involve assessing the ability of antibody specific for the fHbp variant to inhibit binding of fH to fHbp. The strength of inhibition of binding of fH to fHbp by antibody elicited by immunizing with an fHbp variant positively correlates with bactericidal activity of antibody elicited to the fHbp variant. A fHbp variant that elicits antibody that inhibits binding of fH to fHbp at a high serum dilution is considered a suitable candidate for a vaccine for eliciting protection against one or more strains of Neisseria.

For example, the present disclosure provides a method of determining the likelihood that a non-naturally occurring fHbp that has lower affinity for human fH than fHbp ID 1 will elicit bactericidal antibodies in an individual to at least one Neisseria meningitidis strain. The method generally involves determining the ability of an antibody elicited in a test non-human animal to the non-naturally occurring fHbp to inhibit binding of fH to fHbp. Inhibition of binding of fH to fHbp by the antibody elicited to the non-naturally occurring fHbp at a level that is at least about 10%, at least about 25%, at least about 50%, at least about 75%, at least about 2-fold, at least about 10-fold, at least about 50-fold, at least about 100-fold, or greater than 100-fold, higher than the level of inhibition of fH to fHbp by an antibody elicited in the test non-human animal to fHbp ID 1 indicates that the non-naturally occurring fHbp is likely to elicit a bactericidal response to at least one Neisseria meningitidis strain.

Suitable test non-human animals include, e.g., mice, rats, rabbits, and the like. The degree of inhibition of binding of fH to fHbp by antibody elicited to a fHbp variant can be determined using an assay as described herein, or any other known assay. Bactericidal activity of an antibody is readily determined using an assay as described herein, or any other known assay.

A subject method for determining the likelihood that a given non-naturally occurring fHbp that has lower affinity for human fH than fHbp ID 1 will elicit bactericidal antibodies in an individual to at least one Neisseria meningitidis strain is useful for identifying suitable immunogens (and/or eliminating unsuitable immunogens), e.g., in the course of vaccine development.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Overview of Examples

Factor H (fH) is present in high concentrations in serum (~200 to 800 µg/ml). Binding of fH to fHbp is specific for human fH (Granoff et al. (2009) Infect Immun 77:764). One implication is that when humans are immunized with fHbp, the molecule can form a complex with fH. In contrast, when non-human primates or other experimental animals are immunized, the antigen is presented to the immune system without bound fH. In humans, the presence of fH in a complex with fHbp may affect the immunogenicity of fHbp (e.g. by covering epitopes and affecting antigen presentation).

Provided herein is evidence that the presence of human fH decreases protective antibody responses to a fHbp vaccine that binds fH. Further, while certain mutant vaccines with one or two amino acid substitutions do not bind fH (e.g., E218A and/or E239A), the specific mutations used to alter the molecule caused changes that decreased the ability of the vaccines to elicit serum bactericidal antibodies. Additional single amino acid mutants (e.g. R41S or R41A mutants of fHbp ID 1; R41S mutants of fHbp ID 4, 9, 74 or chimeric fHbp I; R130A of fHbp ID 1; R80A, D211A, E218A, E248A, or G236I mutants of fHbp ID 22; a T221A/H223A mutant of fHbp ID 22; R41S/K113A, R41S/K119A, R41S/D121A, or R41S/K113A/D121A mutants of fHbp ID 77; and a K199A or E218A mutant of fHbp ID 28) were identified that had decreased fH binding. A fHbp vaccine with the R41S mutation did not have decreased ability to elicit bactericidal antibodies and in the presence of human fH gave higher protective antibody responses than the wildtype fHbp ID 1 vaccine that bound fH. Other mutations such as K241E of fHbp ID 1 or E241K in fHbp ID 15, which from the crystal structure of fHbp ID 1 are predicted to be in contact with fH, had no effect on fH binding. Further the R41S mutation, which decreased fH binding in fHbp ID 1, 4, 9, and 74, did not decrease fH binding in fHbp ID 22 or 77. Mutations (such as R41S in fHbp ID 1 and other mutations discussed below) that decrease fH binding but have minimal or no effect on the conformation of fHbp such that the mutant vaccine elicits bactericidal antibodies can result in superior vaccine candidates. Thus, fHbp variants are provided that maintain and present a conformational epitope bound by bactericidal antibodies that have bactericidal activity toward one or more *Neisseria meningitidis* strains.

Details of the studies that led to this discovery are set out below.

Materials and Methods

Human fH Transgenic Mouse Model.

The 3.9 kbp human complement fH (cfh) cDNA was cloned into plasmid pCAGGS (Niwa et al. (1991) *Gene* 108:193-9). BALB/c mouse embryos were microinjected with the ~6 kbp SalI-PstI restriction fragment, and implanted into pseudo-pregnant female BALB/c mice. Expression of human fH in sera of pups was detected by Western blotting.

Serum Human fH Concentrations.

To distinguish human and mouse fH, a fHbp capture enzyme-linked immunosorbent assay (ELISA) that specifically binds human fH was used. Recombinant fHbp (2 µg/ml) in sterile phosphate buffered saline (PBS) was added to the wells of microtiter plates. After blocking with 1% bovine serum albumin (BSA), dilutions of pre-immune mouse or human sera were added. Bound human fH was detected using sheep anti-human fH antiserum (Lifespan Biosciences, Seattle, Wash.; 1:2000 dilution). The ELISA was developed with anti-sheep IgG conjugated to alkaline phosphatase. The phosphatase substrate p-nitrophenyl phosphate (Sigma-Aldrich, St. Louis, Mo.) was added and after incubation at room temperature for 30 min, the optical density at 405 nm was measured. fH concentrations were determined in comparison to dilutions of a human reference serum containing 471 µg/ml of fH. As a control, fH was measured in 25 sera from adult subjects in the San Francisco Bay area who participated in an IRB-approved protocol to screen normal sera as complement sources for serum bactericidal assays.

Recombinant fHbp Vaccines.

Recombinant fHbp wild-type and R41S mutant proteins were purified as described (Beernink P T et al. (2008) *Infect Immun* 76:2568-2575). Vaccine immunogenicity was evaluated in six- to eight-week old BALB/c wild-type or human fH transgenic mice, using a protocol approved by the University of Massachusetts Medical School Institutional Animal Care and Use Committee. Three doses of vaccine containing 20 µg of fHbp adsorbed with 600 µg of aluminum hydroxide were administered intraperitoneally at three-week intervals. The control meningococcal group C conjugate vaccine (Meningitec; Wyeth, Montreal, Canada) contained 2 µg of polysaccharide and 3 µg of $CRM_{197}$ adsorbed with 100 µg of aluminum phosphate.

Statistical Analyses.

Two-tailed Student's t tests were used to compare reciprocal geometric mean titers (GMT) of serum antibody responses between two independent groups of mice. A one-tailed t test was also used to examine whether anti-fHbp antibody responses of transgenic mice immunized with the wild-type fHbp vaccine were not lower than immunized wild-type mice. General linear regression models were used to test whether the type of fHbp vaccine and human fH concentrations affected serum bactericidal antibody responses. To meet normality assumption, both serum bactericidal antibody measurements and fH concentrations were login transformed in regression and correlation analyses. A two-tailed P-value of less than or equal to 0.05 was considered statistically significant.

Example 1: Binding of Human Fh Decreases the Immunogenicity of a fHbp Vaccine

Figure 1:
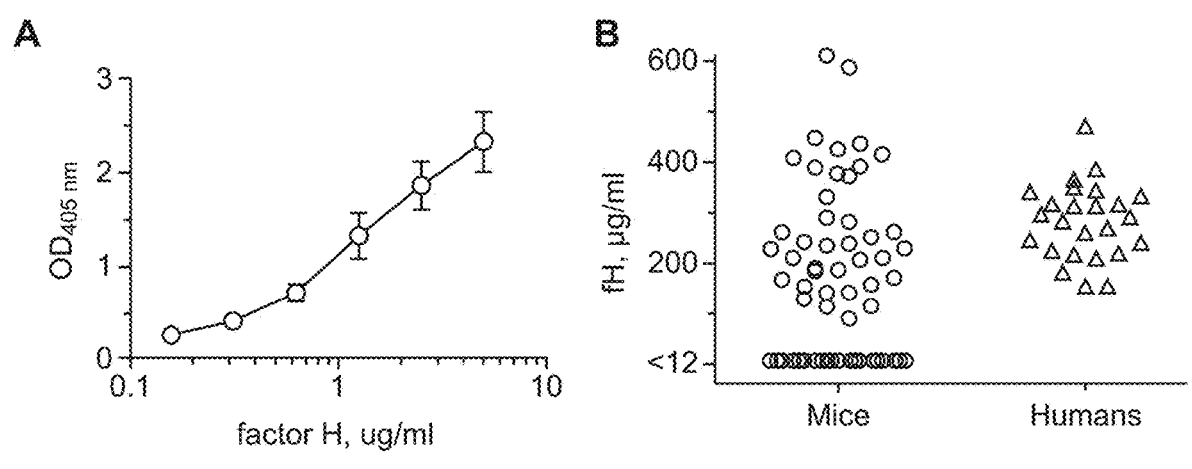
FIG. 1. Panel A, Standard curve of human fH concentration as measured by ELISA with meningococcal fHbp as the antigen in the wells. See Example 1 for details. Panel B, Human fH concentrations in sera of human fH transgenic (Tg) mice, which encompasses human fH-negative littermates of Tg mice or known wildtype BALB/c mice, and the human fH concentrations in the sera of humans. See Example 1.

Binding of fH to fHbp may cover epitopes and impair antibody responses directed at portions of the fHbp molecule exposed on the surface of the bacteria, which are most effective for bactericidal activity. Since binding of human fH to fHbp is specific for human fH, the effect of fH on vaccine immunogenicity was investigated using a human fH transgenic animal model. The human fH concentrations in sera were measured from the transgenic mice using a fHbp capture ELISA described above that is specific for human fH. Control wells contained a purified human fH at concentrations ranging from 0.15 to 5 µg/ml (FIG. 1, panel A). Experimental wells contained different dilutions of transgenic mouse sera (serial 2-fold dilutions starting at 1:100). The human fH concentrations in sera from the transgenic mice were >100 µg/ml. The serum factor H-negative littermates had concentrations <12 µg/ml, which was the lower limit of the assay). Known wild-type mice also had human fH<12 µg/ml). For comparison, fH concentrations in stored serum samples from adult complement donors >100 µg/ml) (FIG. 1, panel B). In the experiments described below, littermates of transgenic mice with <12 µg/ml or known wildtype mice will be referred to as "wildtype" mice.

Figure 2:
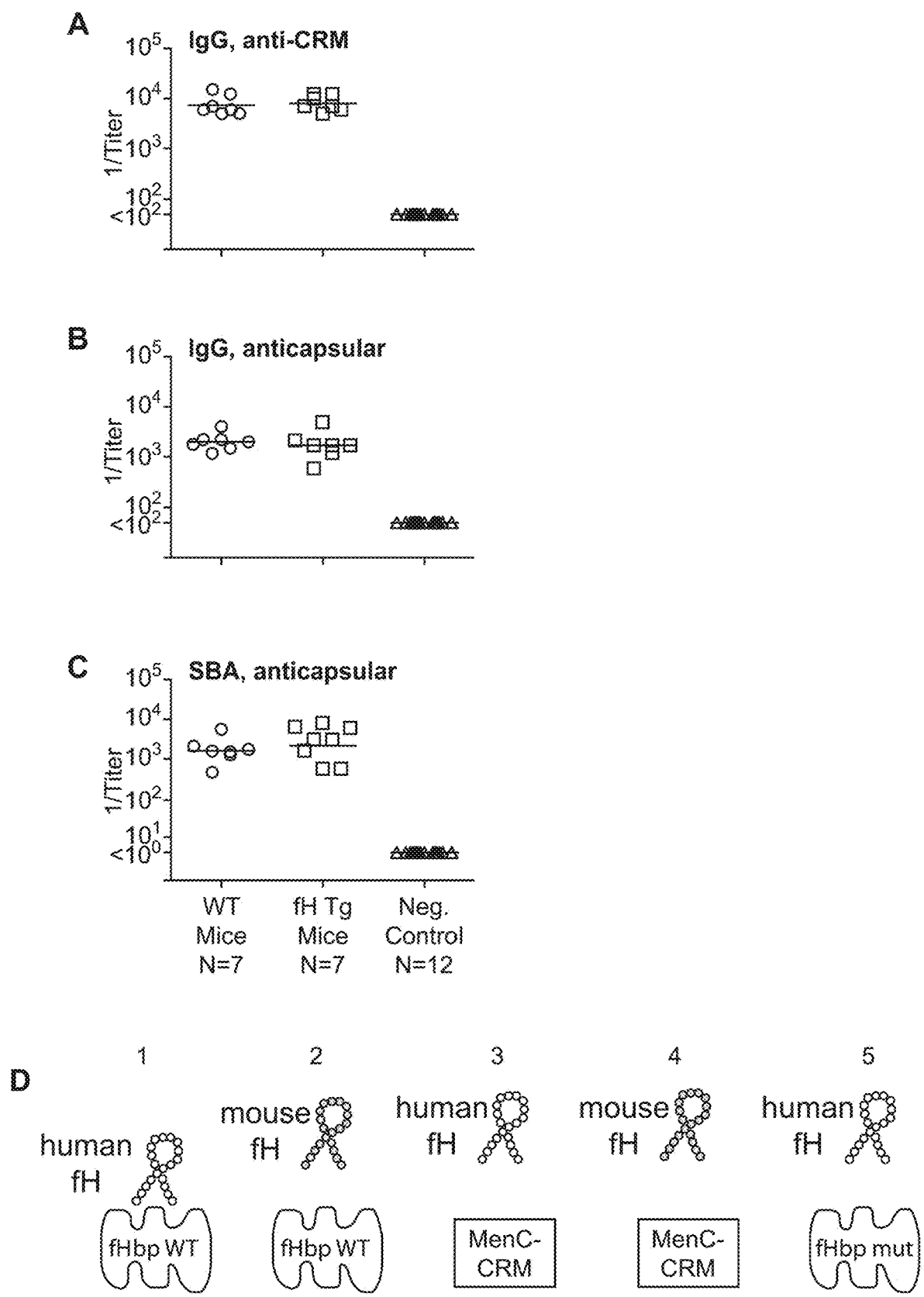
FIG. 2. Serum IgG antibody responses of human fH transgenic (fH Tg) BALB/c mice and wildtype (WT) BALB/c mice immunized with a meningococcal group C conjugate control vaccine (Panels A and B), and serum bactericidal titers against group C strain 4243 (Panel C). The conjugate vaccine does not bind human fH. See Example 1 for details. Panel D. Human fH binds to the wild-type fHbp vaccine, but does not bind to the control MenC-CRM conjugate vaccine or to certain mutant fHbp vaccines, shown schematically to accompany Table 5 in the example section. Mouse (or rabbit, or rat, etc.) fH does not bind to wildtype fHbp.
Figure 3:
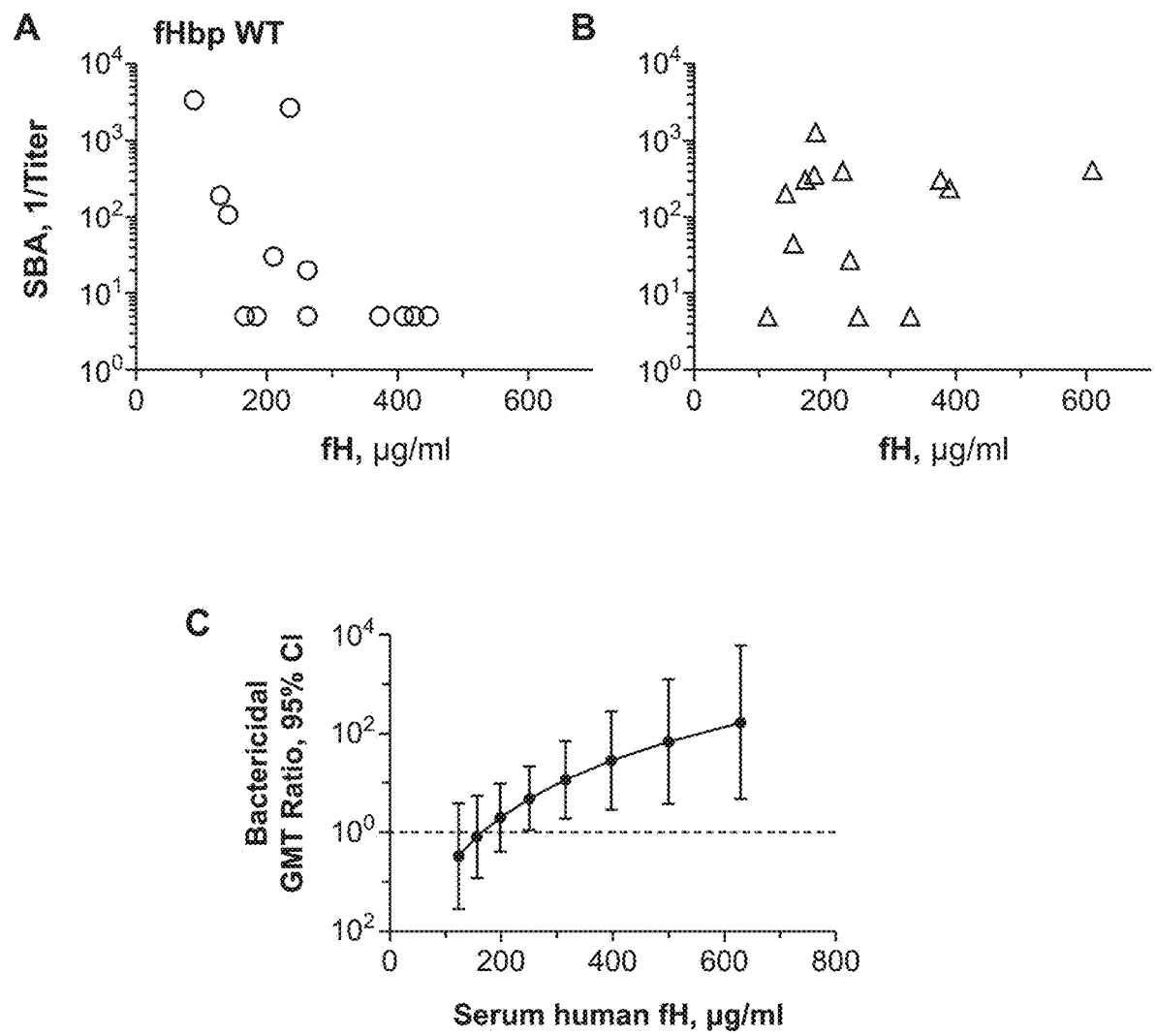
FIG. 3. Relationships between serum human fH concentrations of fH transgenic mice and serum bactericidal antibody responses to vaccination with wild-type fHbp that binds human fH (panel A) or to vaccination with R41S mutant that does not human fH (panel B). Panel C shows the GMT ratios (mutant/wild-type vaccine in relationship to serum human fH concentrations of immunized fH transgenic mice) estimated from the general linear regression model. See Example 4 for details.

In Study 1, human fH transgenic or wild-type mice were immunized with a recombinant fHbp vaccine that bound human fH (Table 1 below). Three weeks after the third injection of vaccine, the serum bactericidal antibody responses of the transgenic mice were 8-fold lower than the wild-type mice whose serum fH did not bind the vaccine (reciprocal GMT of 59 vs. 453 in wild-type mice, P=0.03). Study 1 did not include a control vaccine that did not bind fH. Therefore, it should be determined whether the lower immunogenicity of the fHbp vaccine in the transgenic mice resulted from binding of the vaccine antigen with human fH, or whether the mice might have had lower serum antibody responses to vaccine antigens in general. In Study 2, the fHbp vaccination was repeated and included groups of transgenic and wild-type mice immunized with a control meningococcal group C polysaccharide-$CRM_{197}$ conjugate vaccine that did not bind human fH. The respective serum IgG and bactericidal antibody responses of the transgenic mice immunized with the meningococcal conjugate vaccine were not significantly different from those of the wild-type mice (FIG. 2). As observed in Study 1, transgenic mice immunized in Study 2 with the fHbp vaccine that bound human fH had lower serum bactericidal antibody responses (reciprocal GMT of 31 vs. 115 in wild-type mice, P=0.05, one tailed T test). Further, there was an inverse correlation between the human fH concentrations in the sera of the transgenic mice and serum bactericidal antibody responses to the fHbp vaccine that bound human fH (FIG. 3, panel A; Pearson correlation coefficient, r=−0.65; P=0.02). Thus, the higher the serum human fH concentration, the lower the serum bactericidal response to the vaccine In both studies, the serum IgG anti-fHbp antibody responses of the transgenic mice were lower than the wild-type mice (study 1, reciprocal GMT of 30,000 vs. 97,000, P=0.03; study 2, reciprocal GMT of 107,000 vs. 190,000 (P=0.025). Collectively the data indicated that binding of human fH to the fHbp vaccine impaired both IgG anti-fHbp antibody titers and bactericidal antibody responses.

TABLE 1

Complement-mediated serum bactericidal antibody responses of wild-type or human fH transgenic mice immunized with a recombinant fHbp vaccine that bound human fH

| Study | Mice | No. Mice | fHbp Vaccine | 1/Bactericidal Titer Mean Log$_{10}$ ± SE | Geo. Mean |
|---|---|---|---|---|---|
| 1 | WT | 7 | WT | 2.66 ± 0.21$^a$ | 453 |
| 1 | fH Tg | 10 | WT | 1.77 ± 0.27$^b$ | 59 |
| 2 | WT | 14 | WT | 2.06 ± 0.20$^c$ | 115 |
| 2 | fH Tg | 14 | WT | 1.49 ± 0.27$^d$ | 31 |

The WT fHbp vaccine bound fH. $^{a,b}$P=0.03 (two tailed); $^{c,d}$P=0.05 (one tailed hypothesis based on the results from study 1.

Example 2: fHbp Mutants at Positions 218 and/or 239 Result in Decreased Binding to fH A fHbp mutant with two alanine substitutions at glutamate residues 219 and 239 (E218 and E239) was found to eliminate fH binding (Schneider M C et al. (2009) *Nature* 458:890-3). Recombinant fHbp mutants E218A, E239A and E218A/E239A were prepared by purification via Ni$^{2+}$ affinity chromatography as described (Beernink et al (2010) *Clin Vaccine Immunol* 17:1074-8). Binding of human fH to the fHbp mutants was performed by ELISA using purified recombinant mutant or WT fHbp as the antigen on the plate as described above. Using this method, it was confirmed that the double mutant had decreased binding of fH (FIG. 4). Further, the fHbp mutants with individual mutations at E218 or E239 also had decreased binding of human fH (FIG. 4).

Example 3: The E218a and/or E239A Mutant fHbps have Impaired Immunogenicity in Wild-Type Mice The respective wild-type ID1 fHbp and E218A/E239A double mutant fHbp were subjected to sodium dodecyl sulfate-polyacrylamide gel electrophoresis (SDS-PAGE). Recombinant fHbps expressed in *Escherichia coli* were purified by Ni$^{2+}$ affinity chromatography and five μg of purified protein were loaded onto the gel. A NuPAGE 4-12% polyacrylamide gradient gel (Invitrogen, Carlsbad, Calif.) was run at 200 V for 45 min in MES buffer (Invitrogen) and stained with Simply Blue Safe Stain (Invitrogen). The molecular mass standards were Kaleidoscope Broad Range (Bio-Rad, Richmond, Calif.). The proteins were visualized by COOMASSIE BLUE staining and had similar masses and purity (FIG. 5).

Figure 6:
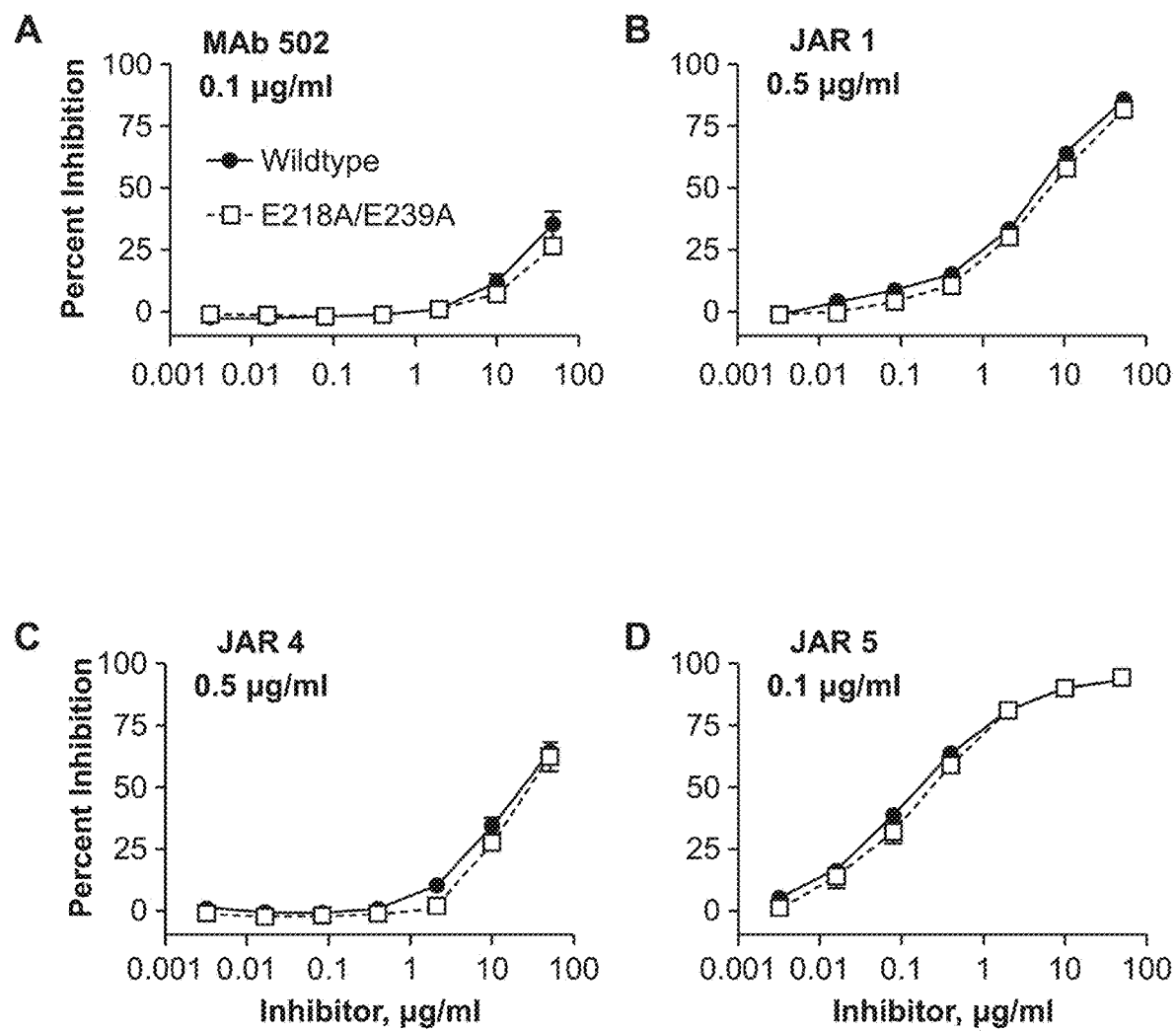
FIG. 6. Soluble fHbp inhibition of anti-fHbp MAb binding to immobilized wild-type fHbp by ELISA.

The inhibition ELISA (Beernink et al (2010) *Clin Vaccine Immunol* 17:1074-8) was performed for both wild-type fHbp ID1 and the E218A/E239A double mutant. The ELISA plate was coated with recombinant fHbp (ID 1) at 2 μg/ml overnight at 4° C. After blocking with PBS/1% BSA, murine anti-fHbp MAbs (JAR 1 or JAR 4 at 0.5 μg/ml; mAb 502 or JAR 5 at 0.1 μg/ml) and serial five-fold dilutions of soluble recombinant protein inhibitor starting at 50 μg/ml (final concentrations) were pre-mixed and added to the wells of the plate and incubated for 1 h at 37° C. Binding of the MAbs was detected with alkaline phosphatase conjugated goat anti-mouse IgG (1:10,000; Sigma-Aldrich) for 1 h at room temperature. The plate was developed as described above in Example 1. The results show that the epitopes recognized by four anti-fHbp MAb were preserved in the E218A/E239A double mutant compared with wild-type fHbp as judged by the ability of the soluble mutant or wildtype protein to inhibit binding of each of the mAbs to wildtype fHbp, which was adsorbed to the wells of the microtiter plate (FIG. 6).

Figure 7A:
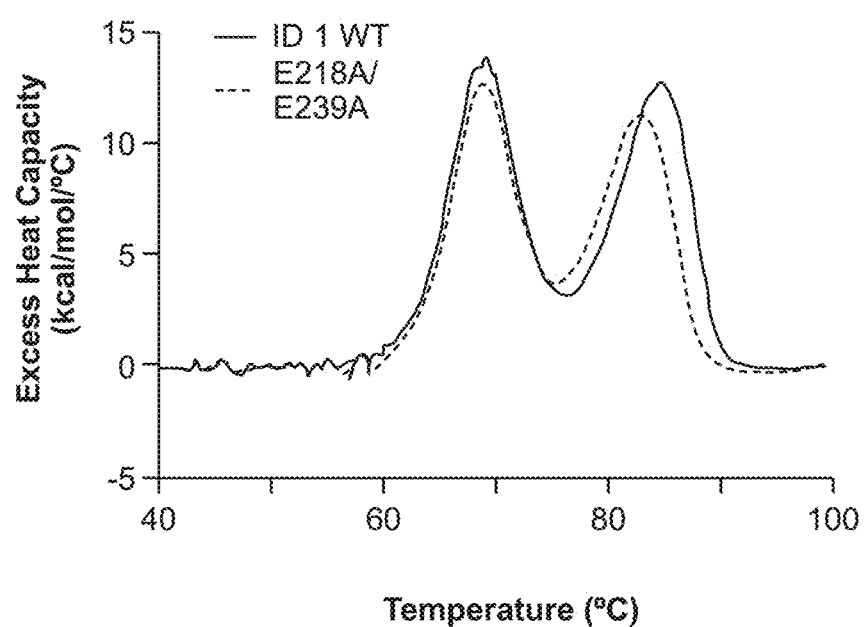
FIGS. 7A-7D.
Figure 7B:
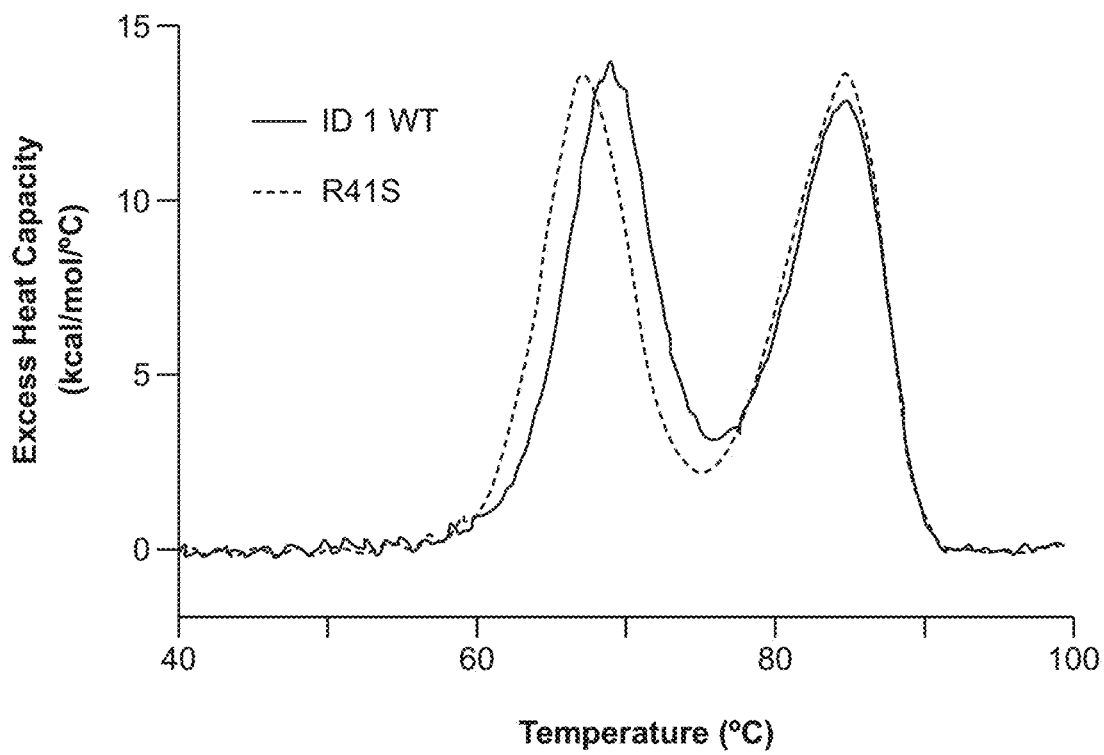

The thermal stability of the fHbps was also determined. Purified recombinant proteins were dialyzed against PBS (Roche Applied Science, Indianapolis, Ind.) overnight at 4° C. The concentration was measured by UV absorbance at 280 nm using a molar extinction coefficient of 0.8940 M$^{-1}$cm$^{-1}$ and adjusted to a concentration of 0.5 mg/ml. Degassed protein solution and PBS were loaded into the sample and reference cells, respectively, of a VP-DSC microcalorimeter (MicroCal, Northampton, Mass.). The heating rate was 60° C./h and the middle gain setting was used. The data were baseline corrected using a buffer vs. buffer scan and normalized based on the protein concentration. The E218A/E239A double mutant had similar thermal stability as that of the wild-type protein (FIG. 7A), as did an R41S mutant (FIG. 7B).

The immunogenicity of the fHbp ID 1 wildtype (WT) and mutant E218A/E239A vaccines was measured in four studies in mice (Studies 3-6). In Study 3, CD-1 mice were immunized with three doses of recombinant WT or mutant fHbp adsorbed with Freund's Adjuvant (FA) or aluminum hydroxide (Al(OH)$_3$); in Study 4, CD-1 mice were immunized with one dose of wild-type (WT) or mutant fHbp adsorbed with aluminum hydroxide (Al(OH)$_3$); in studies 5 and 6, BALB/c mice were immunized with three doses of WT or mutant fHbp adsorbed with aluminum hydroxide (Al(OH)$_3$). In Study 3, the sera were pooled (3 pools per vaccine group, each pool from sera of 3 to 4 mice). In Studies 4, 5 and 6, individual sera were assayed (N=7 to 9 mice per vaccine group).

To measure serum anti-fHbp IgG titers, the ELISA plates were sensitized with recombinant fHbp ID 1 at 2 μg/ml overnight at 4° C. After blocking with PBS/1% BSA, mouse antiserum dilutions (serial five-fold starting at 1:100) were added to the wells of the plate and the plate was incubated for 1 h at 37° C. The bound anti-fHbp antibodies were detected with goat anti-mouse IgG (1:10,000; Sigma-Aldrich, St. Louis, Mo.) for 1 h at room temperature. The plate was developed using p-nitrophenyl phosphate substrate (Sigma-Aldrich, St. Louis, Mo.) at room temperature for 30 min and the optical density at 405 nm was measured.

Figure 7C:
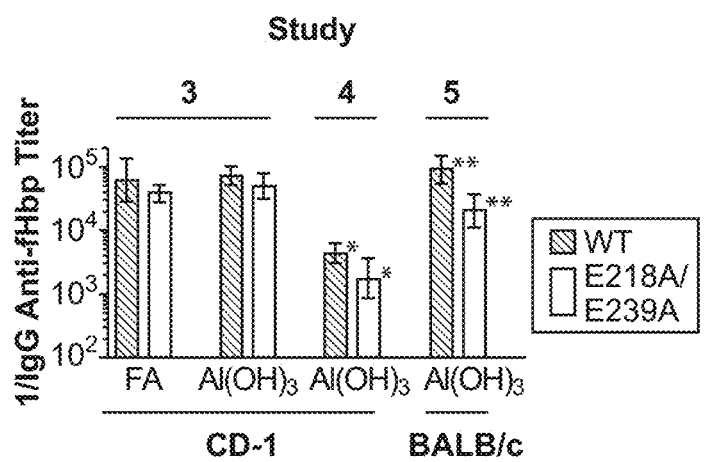
Figure 7D:
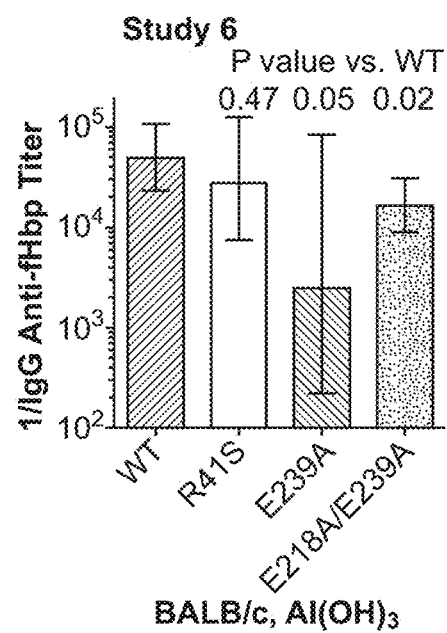

As shown in FIGS. 7C and D, in all four studies (Studies 3, 4 and 5, FIG. 7C; and study 6, FIG. 7D), the E218A/E239A double mutant had decreased serum IgG anti-fHbp antibody responses in conventional BALB/c or CD-1 mice compared with the control wildtype fHbp vaccine. The respective differences were significant (P<0.05) for studies 4, 5 and 6 when individual sera were assayed instead of the pooled sera used in study 3. Study 6 (FIG. 7D) also included a mutant fHbp vaccine with a single amino acid substitution, E239A, which showed lower IgG titers than the WT fHbp vaccine (p=0.05).

Table 2, below, summarizes the serum bactericidal antibody responses to the mutant E218A/E239A vaccine as measured against group B strain H44/76. In all of the studies, the mutant vaccine elicited lower serum bactericidal titers. The respective differences were significant in studies 4, 5 and 6 (P<0.05).

In these studies, neither the double mutant nor wildtype fHbp bound mouse fH. Nevertheless, the lower immunogenicity of the E218A/E239A mutant indicated that epitopes important for eliciting protective bactericidal antibodies were perturbed by introduction of the two mutations. As such, the E218A/E239A mutations that eliminated fH binding did not necessarily maintain optimal structural vaccine characteristics for eliciting protective antibodies.

TABLE 2

Complement-mediated serum bactericidal antibody responses of wild-type mice immunized with the E218A/E239A mutant fHbp vaccine.

| | | | fHbp Vaccine | | | |
| --- | --- | --- | --- | --- | --- | --- |
| | | | WT | | E218A/E239A Mutant | |
| Study[a] | Mouse Strain | No. Doses | 1/Mean $Log_{10}$ Titer ± 2SE | 1/GMT | 1/Mean $Log_{10}$ Titer ± 2SE | 1/GMT |
| 3 | CD-1 | 3 | 2.63 ± 0.54 | 427 | 2.31 ± 0.25 | 206 |
| 4 | CD-1 | 1 | 1.26 ± 0.36[c] | 18 | 0.80 ± 0.14[c] | 6 |
| 5 | BALB/c | 3 | 3.30 ± 0.30[d] | 1986 | 1.68 ± 0.60[d] | 48 |
| 6 | BALB/c | 3 | 1.89 ± 0.22[e] | 77 | 0.95 ± 0.26[e] | 9 |

Bactericidal activity was measured with human complement against strain H44/76. In studies 3, 5 and 6, the mice were immunized with three doses of vaccine. In study 4, one dose was given.
[c]$P < 0.05$
[d]$P < 0.05$
[e]$P = 0.01$

Figure 8:
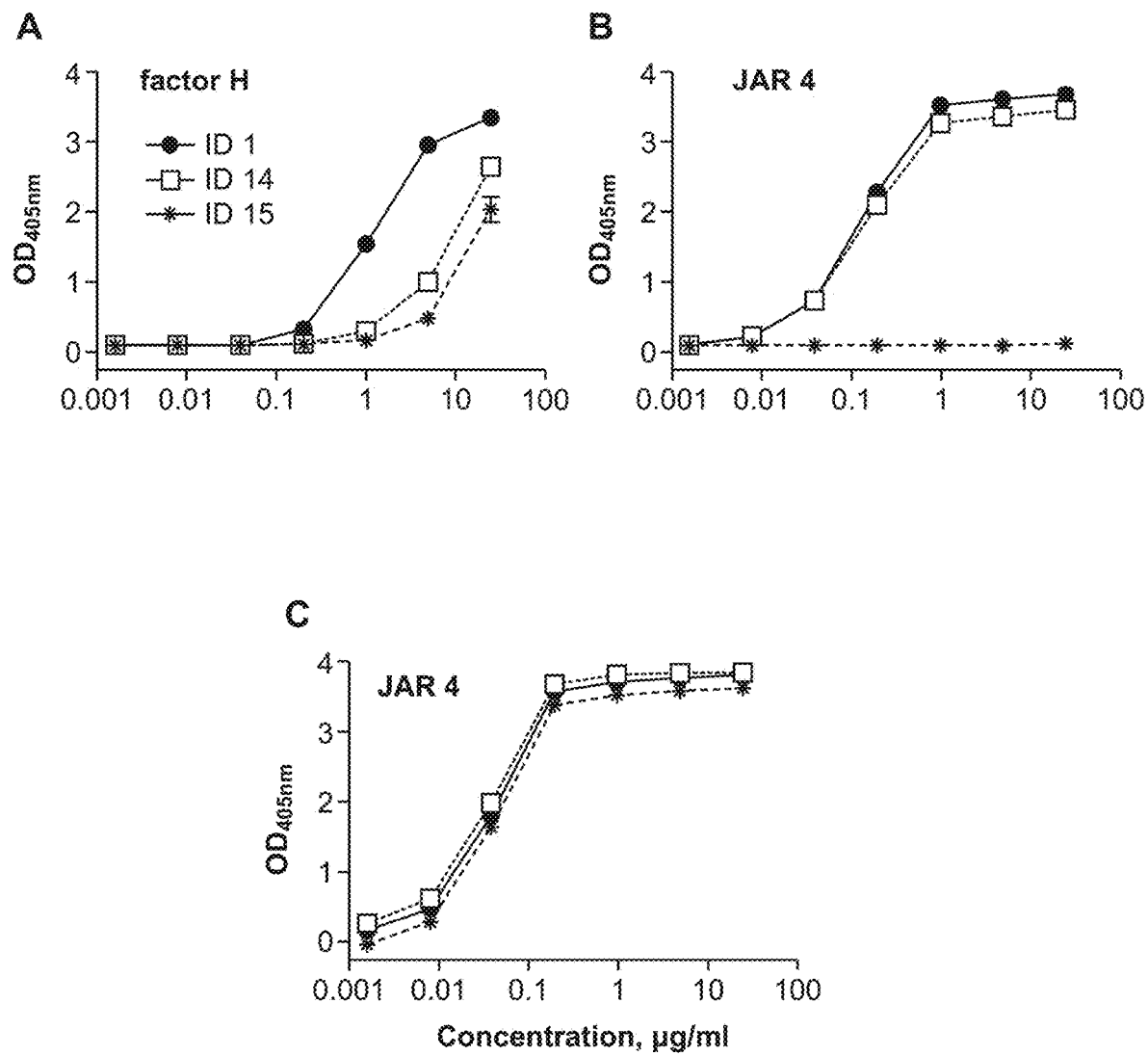
FIG. 8. Panel A depicts binding of fH to natural fHbp variants. Wells of microtiter plates were coated with recombinant fHbps representing variants fHbp IDs 1, 14, or 15.

Example 4: Identification of a Natural fHbp Variant with Decreased fH Binding In studies of fH binding by naturally-occurring fHbp variants within the previously described sub-family B (Fletcher et al (2004) *Infect Immun* 72:2088-2100), also referred to as variant 1 group (Masignani et al. (2003) supra), recombinant proteins of two fHbp variants, IDs 14 and 15, showed significantly less concentration-dependent fH binding than that of fHbp protein ID 1 (FIG. 8). In contrast, fHbp ID 14 showed the expected concentration-dependent binding with anti-fHbp MAbs JAR 4 and JAR 5, and fHbp ID 15 showed the expected binding with anti-fHbp mAb JAR 5 but not JAR 4 (Note, fHbp ID 15 was not expected to bind with JAR 4 because this protein lacks the epitope) (Beernink et al. (2009) *Mol Immunol* 46:1647-1653; Pajon et al. (2009) *Vaccine* 28:2122-2129)).

Previous data indicated that fHbp representative of variant groups 1, 2 or 3 showed similar respective binding with fH (Shaughnessy J et al. (2009) *Infect Immun* 77:2094-103). As such, the decreased binding of fH by two naturally-occurring fHbp variants (fHbp IDs 14 and 15 as shown in FIG. 8) was unexpected.

The data obtained as represented in FIG. 8 showing low fH binding by two naturally-occurring fHbp variants indicates that amino residues contributing to such lower fH binding can be identified by analysis of alignments of the fHbp amino acid sequences of high- and low-fH binders. This strategy would be different from one that targets conserved residues, such as the E218A and E239A residues.

fHbp variants can be subclassified according to different combinations of five variable segments, each derived from one of two genetic lineages, designated α- or β-types (Pajon et al. (2009) *Vaccine* 28:2122; Beernink and Granoff (2009) *Microbiology* 155:2873-83). fHbp ID 1 with high fH binding and ID 14 with low fH binding are both in modular group I (all five segments are alpha-types). In contrast, the second low fH binder, fHbp ID 15, is in modular group IV, which are natural chimeras (with a β-type A segment and α-type B, C, D and E segments). Therefore, as a control for the β A segment of peptide ID 15, the sequence of the naturally high fH binding variant peptide ID 28 was used, which contains only β segments (modular group II). The respective amino acid alignments are shown in FIGS. 19A and 19D. For purposes of comparison of the sequences of the different variants, specific residues are referred herein based on the numbering of fHbp ID 1. One of these amino acid residues, serine (S), at position 41 of the A (β) segment of peptide 15 (low fH binding) differed from the proline (P) residue of the control A β segment of peptide 28 (high fH binding). A second amino acid, E at position 241 in the E α segments of both low fH binding variants, differed from that of K at position 241 of the high fH binding variant peptide 1.

Example 5: Identification of New fHbp Mutants at Position 41 with Decreased fH Binding The arginine residue at position 41 (R41) formed a charged hydrogen-bond with fH (FIG. 9, panel A). Arginine was replaced by serine to eliminate this charged bond (S41, lower right inset panel). Wells of microtiter plates were coated with recombinant WT fHbp ID 1 or the R41S mutant ID 1. By ELISA, the R41S mutant did not bind human fH (FIG. 10, panel A). Control anti-fHbp MAbs, JAR 4 and JAR 5, bound almost identically to both the mutant fHbps and wild-type fHbp (FIG. 10, panels B and C). These controls indicated that comparable amounts of the respective proteins were adsorbed to the wells of the microtiter plate. Further, the R41S mutation, which was in the same domain and in close proximity to the fHbp conformational epitope recognized by the JAR 4 MAb (Beernink P T (2009) *Mol Immunol* 46:1647-53), did not affect binding of the MAb. An additional mutation in fHbp ID 1 in which alanine was substituted for arginine, R41A also did not bind fH (FIG. 10A). Thus substitutions other than serine at position 41 also can decrease fH binding.

In surface plasmon resonance experiments, human fH (2400 response units) was immobilized on a CM5 chip (GE Healthcare, Piscataway, N.J.) via amine coupling and binding of soluble fHbp was measured. The R41S mutant protein (0.5 µM) showed no binding with fH (−0.6 response units) compared with +22.5 response units with 0.5 µM of the respective wild-type fHbp antigen, which independently confirmed the ELISA results. The R41S mutant protein also had thermal stability compared with that of the wild-type fHbp (FIG. 7, panel B).

The R41S mutation also eliminated fH binding when the mutation was introduced in other fHbp sequence variants in the variant group 1, modular group I. These included fHbp ID 4, 9, and 74 (FIG. 11, panels A, C, and E, respectively). However, the R41S mutation in three sequence variants in the variant group 2 (modular groups III or VI) did not decrease fH binding. These included fHbp ID 19, 22 and 77 (FIG. 12, panels A, C, and E, respectively).

Example 6: Immunogenicity of R41S Mutant fHbp in Wild-Type Mice

In wild-type mice, the R41S mutant fHbp (ID 1) vaccine elicited similar serum bactericidal antibody responses as the wild-type vaccine (Table 3, below, Studies 2 and 6). In study 6, a double mutant fHbp vaccine, E218A/E239A, which previously was reported not to bind to fH (Schneider M C et al. (2009) *Nature* 458:890-3), but had impaired immunogenicity in WT mice (Beernink et al. (2010) *Clin Vaccine Immunol* 17:1074), served as a negative control. This vaccine elicited significantly lower bactericidal titers (Table 3, Study 6), and thus confirmed the data described in Table 2 above, showing diminished antibody responses to the E218A/E239A vaccine from possible loss of epitopes or minor destabilization of the mutant molecule (Beernink et al. (2010) *Clin Vaccine Immunol* 17:1074-8). In contrast, the normal antibody responses to the R41S mutant fHbp vaccine indicated that substitution of serine for arginine did not decrease immunogenicity in a mouse model where fH did not bind to the mutant or wild-type fHbp vaccines.

TABLE 3

Complement-mediated serum bactericidal antibody responses of wild-type mice immunized with fHbp recombinant fHbp vaccines.

| Study | Mice | No. Mice | fHbp Vaccine | 1/Bactericidal Titer Mean $Log_{10}$ ± SE | 1/Bactericidal Titer Geo. Mean |
|---|---|---|---|---|---|
| 2 | WT | 14 | WT | 2.06 ± 0.20 | 115[a] |
| 2 | WT | 13 | R41S | 1.92 ± 0.20 | 83[b] |
| 6 | WT | 9 | WT | 1.89 ± 0.22 | 77[c] |
| 6 | WT | 9 | E218A/E239A | 0.95 ± 0.26 | 9[d] |
| 6 | WT | 9 | R41S | 1.85 ± 0.31 | 71[i] |

The WT fHbp vaccine bound human fH; the R41S mutant and previously described E218A/E239 mutant (Schneider et al. (2009) *Nature* 458:890-3) did not bind human fH. In WT mice, native fH does not bind to either vaccine (FIG. 1, Panel D): [a,b]P=0.62; [c,d]P=0.01; [d,i]P=0.92, by T tests (two tailed).

Example 7: Serum Bactericidal Antibody Responses of Transgenic Mice Immunized with the R41S Mutant fHbp Vaccine Human fH transgenic mice immunized with the R41S mutant vaccine that did not bind human fH had ~3-fold higher serum bactericidal antibody responses than human fH transgenic mice immunized with the control wildtype fHbp vaccine that bound fH (Study 2, Table 4 below). When the data were stratified by serum human fH concentrations, mice with fH concentrations <250 μg/ml showed similar responses to the mutant and wildtype vaccines. However, among mice with human fH concentrations >250 μg/ml, those immunized with the R41S mutant vaccine had 10-fold higher bactericidal antibody responses than those immunized with the wildtype fHbp vaccine that bound human fH (P<0.05; Table 4).

TABLE 4

Serum bactericidal antibody responses of human fH transgenic mice immunized with the R41S mutant vaccine

| Study | Human fH, μg/ml | No. Mice | fHbp Vaccine | 1/Bactericidal Titer Mean $Log_{10}$ ± SE | 1/Bactericidal Titer Geo. Mean |
|---|---|---|---|---|---|
| 2 | >100 | 14 | WT | 1.49 ± 0.27[a] | 31 |
| 2 | >100 | 13 | R41S | 1.98 ± 0.23[b] | 96 |
| Stratified analysis by human fH concentration | | | | | |
| 2 | <250 | 7 | WT | 2.02 ± 1.16[c] | 105 |
| 2 | <250 | 8 | R41S | 2.11 ± 0.78[d] | 129 |
| 2 | ≥250 | 6 | WT | 0.80 ± 0.10[e] | 6 |
| 2 | ≥250 | 5 | R41S | 1.78 ± 0.44[f] | 60 |

The WT fHbp vaccine bound human fH; the R41S mutant did not bind human fH. The data for the fH transgenic mice immunized with the wild-type vaccine are shown in study 2, Table 1 above. [a,b]Using general linear regression models, the effect of fHbp R41S mutant or wild-type vaccine type differed by serum human fH concentration on bactericidal titer, P=0.018. [c,d]p>0.5. [e,f]P=0.05.

In immunized human fH transgenic mice, there was no significant correlation between the serum bactericidal antibody responses to the mutant fHbp vaccine that did not bind human fH and serum human fH concentrations (FIG. 3, panel B; r=+0.17; P=0.58), whereas as described above (FIG. 3, panel A), in the transgenic mice there was an inverse correlation with the bactericidal titers elicited by the wild-type vaccine that bound fH (r=−0.65; P=0.02). The respective correlation coefficients for the two vaccines were significantly different from each other (P=0.03).

General linear regression models were used to confirm if the type of fHbp vaccine (fHbp wild-type or R41S mutant) or the serum human fH concentration affected the serum bactericidal antibody responses of the transgenic mice. There was a significant interaction between the type of fHbp vaccine and the human fH concentration on the bactericidal response (likelihood ratio test, P=0.018). Based on the regression model, ratios of the reciprocal serum bactericidal GMTs were estimated for transgenic mice immunized with the R41S mutant vaccine over those of transgenic mice immunized with the fHbp vaccine that bound human fH at various serum human fH concentrations (FIG. 3, panel C). While there were no significant differences in bactericidal responses when serum human fH concentrations were low (<250 μg/ml), the bactericidal responses to the R41S mutant vaccine were significantly higher when the serum fH concentrations were higher (fH>250 μg/ml, P<0.05; fH>316 μg/ml, P<0.01). Since many humans have fH concentrations in this range (FIG. 1, panel B), the results in the transgenic mice suggest that mutant fHbp molecules that do not bind fH can be superior vaccines in humans.

The experimental protocols of various immunization studies presented above as well as the results are summarized in the table below.

TABLE 5

Summary of immunization studies in human fH transgenic mice.

| Study | BALB/c mouse strain | Meningococcal Vaccine(s) | fH binding to vaccine | Results |
|---|---|---|---|---|
| 1 | Human fH Tg | Factor H binding protein (fHbp) | Yes[1] | Lower serum IgG and bactericidal antibody response of Tg mice whose human fH bound to the vaccine antigen |
|  | Wild-type control | fHbp | No[2] |  |
| 2A | Human fH Tg | fHbp | Yes[1] | Confirmed lower serum IgG and bactericidal antibody responses of Tg mice |
|  | Wild-type control | fHbp | No[2] |  |
| 2B | Human fH Tg | Group C PS-CRM conjugate | No[3] | Wild-type and Tg mice showed nearly identical respective serum IgG and bactericidal responses to a control meningococcal vaccine that didn't bind fH |
|  | Wild-type control | Group C PS-CRM conjugate | No[4] |  |
| 2C | Human fH Tg | fHbp | Yes[1] | Higher serum bactericidal antibody responses to the mutant fHbp that did not bind fH, especially for the mice with high serum human fH levels. For the vaccine that bound human fH, inverse correlation between serum bactericidal titer and serum human fH concentration. For the mutant vaccine that didn't bind human fH, no significant correlation between serum bactericidal titers and serum human fH concentrations. Hence, in mice vaccinated with mutant fHbp, serum bactericidal titers were independent of the serum human fH concentration. |
|  | Human fH Tg | fHbp R41S mutant | No[5] |  |

FIG. 2, panel D provides a schematic illustration of each experimental protocol corresponding to the various studies presented herein. The number above each illustration in FIG. 2D corresponds to the superscripts in the table above. Group C PS-CRM conjugates are a conjugate of meningococcal group C polysaccharide (PS) and a cross-reactive mutant diphtheria toxoid (CRM) and are referred to as MenC-CRM in FIG. 2, panel D.

Figure 13:
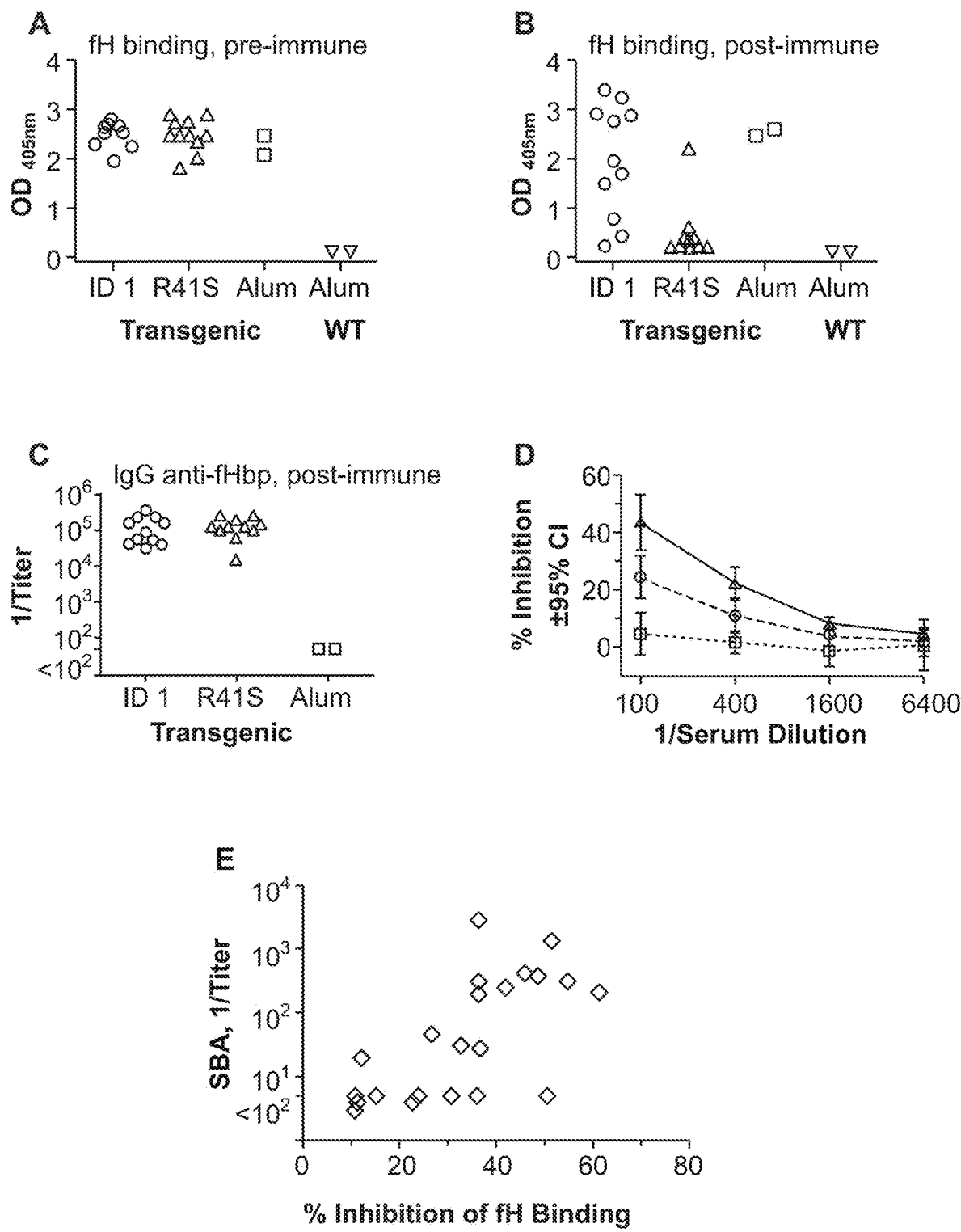

Example 8: The Antibody Repertoire of Transgenic Mice Immunized with the R41S Mutant fHbp Vaccine Preferentially Binds Epitopes Near the fH Binding Site The importance of binding of human fH that covers fHbp epitopes in eliciting antibodies with protective functional activity was tested. The ability of endogenous human fH present in 1:100 dilutions of sera from transgenic mice to bind to fHbp by ELISA was measured. As expected, in the absence of serum anti-fHbp antibodies, there was similar binding of human fH in pre-immunization sera from the two vaccine groups and the control transgenic (Tg) mice given aluminum hydroxide alone (FIG. 13, panel A). There was no binding in the control WT mice given aluminum hydroxide since the native fH did not bind to fHbp. After vaccination, there was less "free" human fH detected in the sera from mice immunized with the R41S mutant fHbp than in the sera from mice immunized with the vaccine that bound human fH (P=0.001, FIG. 13, panel B), or in sera from transgenic mice given aluminum hydroxide alone (FIG. 13, panel B). Since the respective IgG anti-fHbp antibody titers were similar in the two fHbp vaccine groups FIG. 13, panel D), the lower detectable human fH concentrations in the R41S post-immunization sera were consistent with greater ability of the anti-fHbp antibodies to inhibit binding of human fH to fHbp than the anti-fHbp antibodies elicited by the wild-type vaccine that bound human fH. Individual mouse sera (N=11 per group) were also tested at different dilutions in the presence of 5% normal human serum as a source of fH. At 1:100 and 1:400 dilutions, inhibition was significantly greater in the R41S mutant vaccine group (P<0.03), FIG. 13, panel C). Collectively, the greater fH inhibition in the R41S mutant vaccine group suggested that there were differences in antibody repertoire elicited by the two vaccines. For example, antibodies elicited by the mutant fHbp vaccine may have been directed more at epitopes near the fH binding site, which would be more effective in blocking fH binding than the antibody repertoire elicited by the vaccine that bound fH. Further, antibodies directed at surface-exposed regions of fHbp that also bind to fH would be expected to have greater functional bactericidal activity.

A significant correlation (Spearman r value, 0.69 and P value of 0.0004) was also observed between the ability of individual mouse sera to inhibit binding of human fH to fHbp and the reciprocal serum bactericidal titer (FIG. 13, panel E). In the serum bactericidal reaction, a decrease in binding of the complement inhibitor fH to the bacterial surface of the test organism may have contributed to the higher bactericidal titers elicited by the mutant fHbp vaccine. Thus, the ability of the anti-fHbp antibodies to inhibit fH binding predicted protective antibody activity, which was greater for the R41S vaccine.

Figure 14:
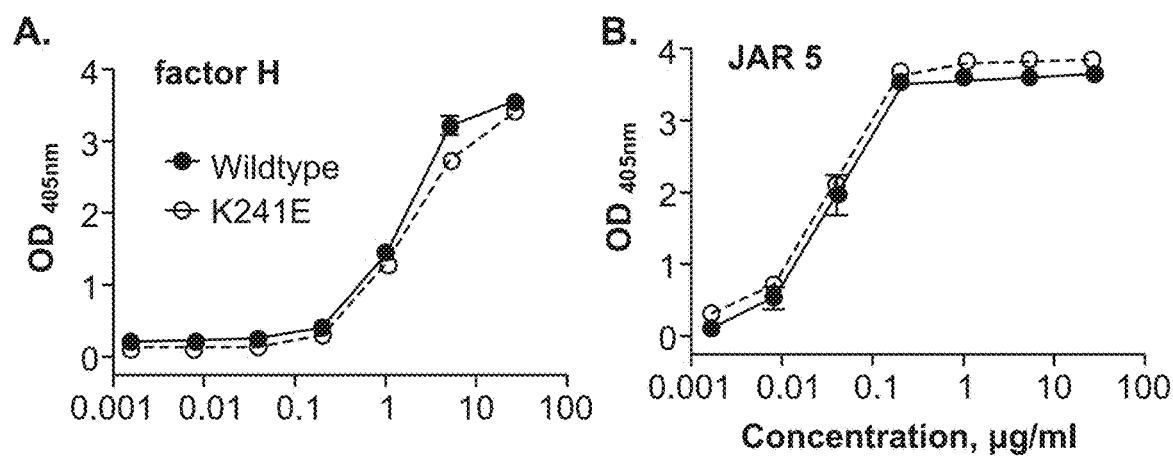

Example 9: Identification of Additional Mutants in fHbp ID 1 with Decreased fH Binding Position 241 is in the fH binding interface of fHbp ID 1. The effect of amino acid substitutions on binding of fH was investigated at residue 241 in the fHbp ID 1 sequence. As shown in FIG. 14, panel A, replacement of residue lysine (K) 241 with glutamate (E) (K241E) in fHbp ID 1 had no effect on fH binding. The converse substitution, the E241K mutant of fHbp ID 15 in modular group IV (FIG. 14, panel C) also showed no significant effect on fH binding relative to the wildtype fHbp (<2-fold; FIG. 14, panel C). (Numbering of amino acid residues is based on the sequence of fHbp ID 1.)

In fHbp ID 1, mutations at positions R41, H119, R130, and K241. The fHbps mutants were produced as described above. The R41A, H119A, R130A, and K241E single substitution mutants were then assessed for binding to human fH, and for binding to MAbs.

As shown in FIG. 10, panel A, the R41S substitution and the R41A substitution in fHbp ID 1 reduced binding to human fH. As shown in FIG. 10, panel B and C, the R41S and the R41A mutants retained binding to MAbs JAR 4 and JAR 5, respectively, which indicated that these epitopes are preserved in the R41S and the R41A mutants.

Figure 15:
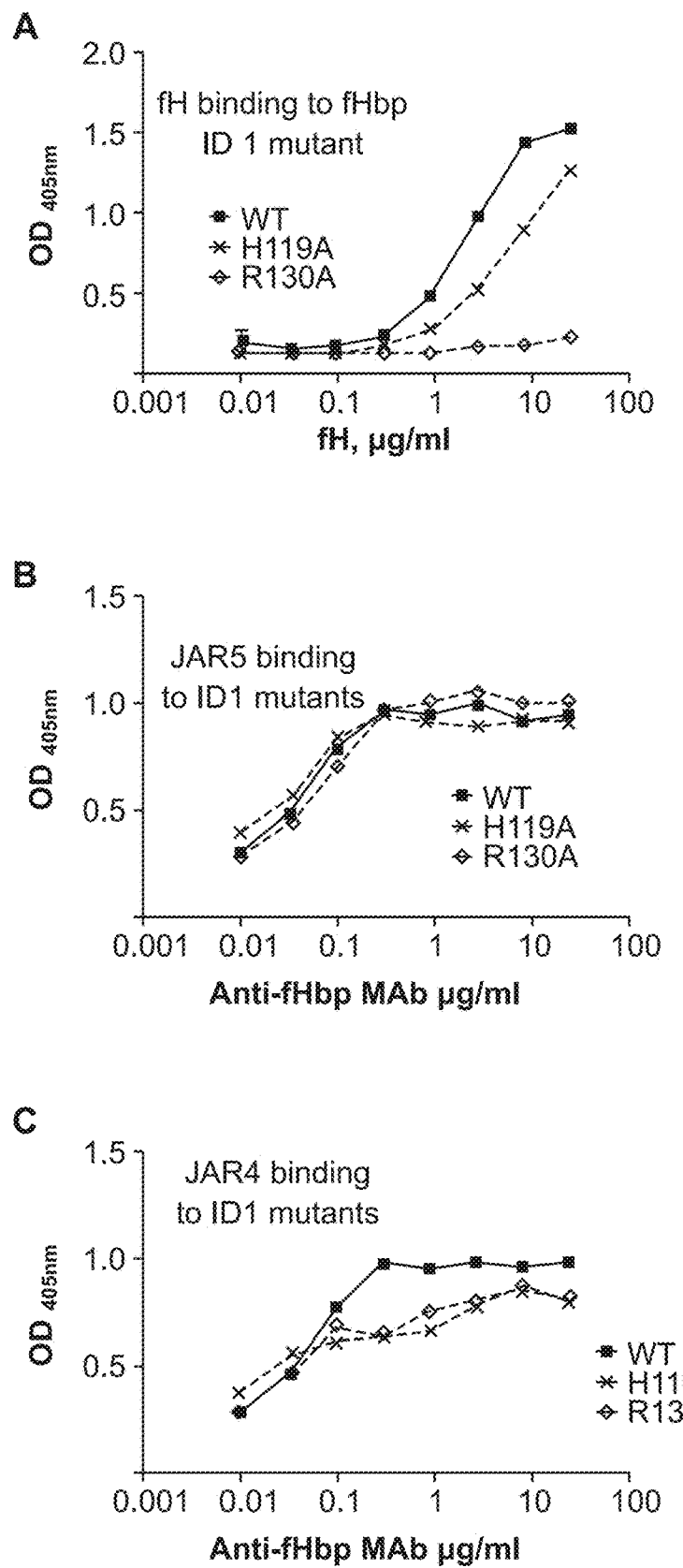

As shown in FIG. 15, panel A, the H119A and the R130A substitutions in fHbp ID 1 reduced binding to human fH. As shown in FIG. 15, the H119A and the R130A mutants retained binding to MAb JAR5 (panel B) and lowered binding to MAb JAR4, compared to the corresponding wildtype fHbp ID 1 (panel C). These data indicate that the JAR5 epitope is preserved in the H119A and the R130A mutants; and that the JAR 4 epitope is partially preserved by the amino acid substitutions.

Example 10: Mutants in fHbp Sequence Variants from fHbp Modular Group IV

The "$V_A$" segments in variant group 1, fHbp sequence variants classified as variant 1, modular group IV (FIG. 16) are derived from a different genetic lineage (β) than the corresponding "$V_A$" segments in variant 1, modular group I fHbp sequence variants, which are designated as α segments (Beernink et al (2009) *Microbiology* 155:2873). The respective α and β lineages can also be designated as lineages 1 and 2, according to the nomenclature adopted by the pub-mlst.org/neisseria/fHbp/ website.

In modular group IV fHbp amino acid sequence variants, there often is a serine at position 41 instead of arginine. Substituting proline for serine (S41P) in a mutant of fHbp ID 15 (modular group IV) eliminated binding of fH (FIG. 17). Control proteins included recombinant fHbp IDs 1 and 28 (naturally high fH binders) and fHbp ID 15 (naturally low fH binder). Human factor H or anti-fHbp MAb binding to fHbp was measured by ELISA as described above. Anti-fHbp MAb JAR 5 showed similar binding with WT fHbp IDs 1 and 15, and the S41P mutant of fHbp ID 15 (FIG. 17, panel B). JAR 31 showed the expected binding of fHbp ID 28 (FIG. 17, panel C).

Figure 12:
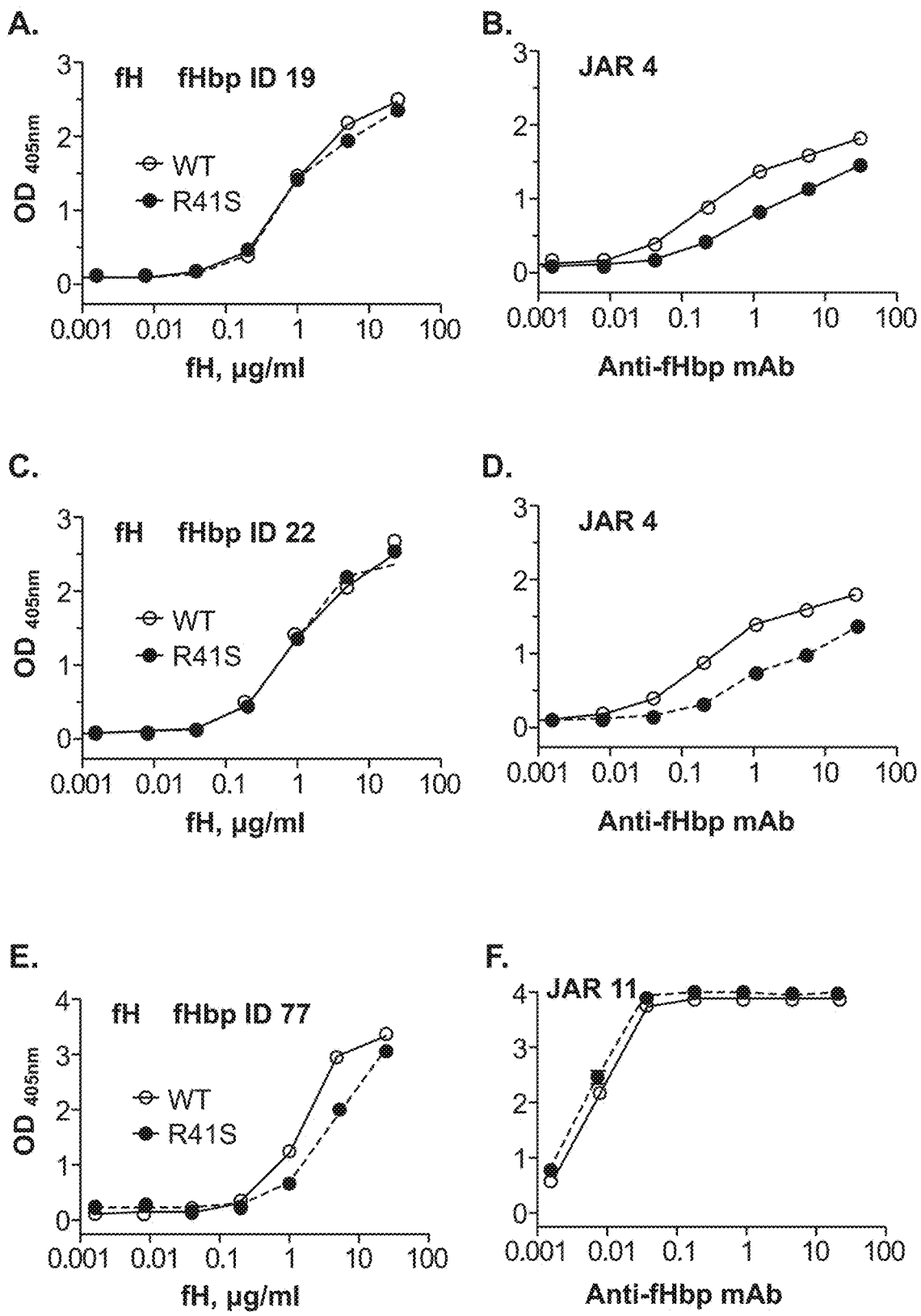

Example 11: R41S Amino Acid Substitutions in fHbp Sequence Variants from Modular Groups III and VI do not Affect fH Binding All fHbp sequence variants classified as variant 2 are natural chimeras that contain segments derived from both α and β lineages (FIG. 16). Specifically, the "$V_A$" segments in variant 2 proteins are derived from α lineages and as in modular group I frequently contain an arginine at residue 41 (numbering of the residues according to fHbp ID 1). Although the R41S substitution in all modular group I proteins tested eliminated fH binding (FIGS. 11 and 10 and Table 6), the R41S mutation in fHbp ID 19, 22 and 77 from variant 2 group (modular groups III or VI) did not eliminate fH binding (FIG. 12, panels A, C and E, and Table 7).

Example 12. Synthetic fHbp Chimeric Proteins that do not Bind Human fH

Figure 18:
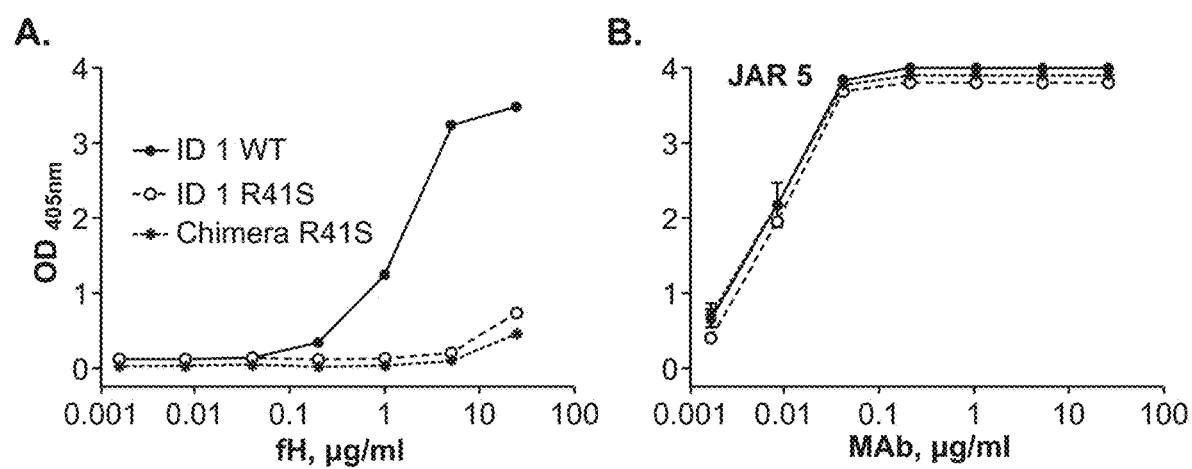

A fHbp chimera I (Beernink and Granoff (2008) *Infect. Immun.* 76:2568-75) is shown as the last modular schematic in FIG. 16. The junction point at which part of fHbp ID 1 (variant 1, modular group I) is fused to part of fHbp 77 (variant 2, modular group VI) is G136, which resides in segment $V_C$. In FIG. 16, $V_C$ is depicted as half gray and half white in the chimeric protein to represent the fusion of a α lineage sequence to a β lineage sequence in that segment. When the R41S substitution was introduced into variant 2 fHbp protein, there was no effect on fH binding (FIG. 12, panels A, C, and E). In contrast, when the R41S substitution was inserted in the fHbp chimera I protein, the mutation eliminated fH binding. (FIG. 18). This results was not anticipated since the only amino acid differences between the respective $V_A$ segments of chimera I and fHbp ID 77 was one amino acid residue (Gly30 in the chimeric antigen instead of Ser30; FIG. 19). In the $V_C$ segment, there were differences in eight of the residues between positions 98 and 135 (FIG. 19), which may explain why the R41S mutation eliminated fH binding in the chimeric protein but not in the natural variant 2 proteins (shown schematically in FIG. 16; and complete amino acid sequence shown in FIG. 19A). These observations implicate residues in this portion of the $V_C$ region as being important for stability of the fHbp-fH complex in fHbps in variant 2 group.

Example 13. Effect of Additional Amino Acid Substitutions in fHbp ID 77 (Modular Group VI) on Binding of fH Alanine mutations at positions K113, K119, D121, were introduced into fHbp ID 77 (Modular Group VI, antigenic variant group 2). As noted above, the residue position number is based on fHbp ID 1. fHbps were produced as described above in Materials and Methods.

The ability of these mutants to bind to human fH were tested by ELISA as described above in Example 2 and compared to the corresponding wild-type fHbp. Introducing the K119A mutation increased fH binding approximately 4-fold compared to wildtype fHbp ID 77 (FIG. 20, Panel A); K113A had no effect on fH binding (FIG. 20, Panel A) while D121A decreased fH binding by about 4-fold compared with binding of fH by wildtype fHbp ID 77 (FIG. 20, Panel A). Anti-fHbp JAR 31 bound to all three mutants, which indicated that respective amino acid substitutions did not affect the epitope recognized by this mAb.

Double amino acid substitutions, R41S/K113A, R41S/K119A and R41S/D121A were also constructed in fHbp ID 77. The R41S/K119A mutant showed about 5-fold decrease in fH binding by ELISA (FIG. 21, Panel A), while the R41S/K113A and R41S/D121 mutant had about 10-fold less binding to fH than the wildtype fHbp ID 77 (FIG. 21, Panel A and Table 6). Anti-fHbp mAb JAR 31 showed similar binding with all three of these double mutants of ID 77 and the wildtype fHbp ID 77, which indicated that there were similar amounts of each of the fHbp variants adhered to the microtiter wells and that these amino acid substitutions did not affect the epitope recognized by this mAb.

A triple amino acid substitution R41S/K113A/D121A was introduced in fHbp ID 77. This triple mutant exhibited no fH binding (FIG. 22, Panel A). The mutant fHbp retained binding to JAR 31 (FIG. 22, Panel C), but eliminated JAR 4 binding (FIG. 22, Panel B). In contrast, the K113A/D121A double mutant had approximately 10-fold decreased binding of fH, which indicated that these substitutions in addition to the R41S substitution contributed to the loss of fH binding.

Example 14. Effect of Amino Acid Substitutions in fHbp ID 22 (Modular Group III) on Binding of fH fHbp ID 22 is representative of fHbp sequence variants in modular group III (variant group 2, FIG. 16). Mutations were introduced in fHbp ID 22 at positions R80, D211, E218, D248, G236 (Table 6), and R41, Q38, A235, Q126, D201 and E202 (Table 7). The fHbp mutants were produced as described above. Specifically, R80A, D211A, E218A, E248A, R41S, Q38A, Q126A, G236I, A235G, D201A, and E202A substitutions were introduced singly into fHbp ID 22. In addition, T221A/H223A double substitutions were introduced into fHbp ID 22. The mutants were then characterized for fH binding and binding to anti-fHbp mAbs by ELISA (Tables 6 and 7).

The ability of these mutants to bind to human fH was tested as described above in Example 2, and compared to the ability of wild-type fHbp ID 22 to bind to human fH. The results are shown in FIG. 23, panels A-C and summarized in Tables 6 and 7. As shown in FIG. 23 panels A and B, the D211A, R80A, E218A, and E248A substitutions in fHbp ID22 reduced binding to fH by more than 50-fold compared with binding fH by the wildtype fHbp ID 22 (See also Table 6). As shown in FIG. 23 panel C, the R41S, Q38A, and Q126A substitutions did not significantly reduce binding to fH (<4-fold; see also Table 7).

As shown in FIG. 24, panels A and B, the R80A, D211A, E218A, and E248A mutants of fHbp ID22 retained binding to MAb JAR31, indicating that the JAR31 epitope is preserved in each of these mutants.

As shown in FIG. 25, panels A and B, the D211A and the E218A mutants of fHbp ID 22 retained binding to MAb JAR4, indicating that the JAR4 epitope is preserved in these mutants. As shown in FIG. 25 the R80A mutant did not retain binding to MAb JAR4 (panel A), and the E248A mutant showed reduced binding to MAb JAR4 (panel B).

As shown in FIG. 26, panels A and B, the R80A, D211A, E218A, and E248A mutants of fHbp ID 22 retained binding to MAb JAR35, indicating that the JAR35 epitope is preserved in each of these mutants.

As shown in FIG. 27, panel A, the T221A/H223A double substitution and the G236I single substitution in fHbp ID 22 reduced binding to human fH by more than 50-fold compared with binding of fH by wildtype fHbp ID 22 (See also Table 6). As shown in FIG. 27, the T221A/H223A mutant in fHbp ID 22 retained binding to MAb JAR31 (panel B), MAb JAR 35 (panel C), and MAb JAR 4 (panel D), which indicates that the JAR31, JAR35, and JAR4 epitopes are preserved in the T221A/H223A mutant. As shown in FIG. 27, the G236I mutant in fHbp ID 22 retained binding to MAb JAR 35 (panel C), but exhibited reduced binding to MAb JAR 31 (panel B), and had little or no binding to JAR 4 (panel D).

As shown in FIG. 28, panel A, the R41S, Q38A, and A235G single substitutions in fHbp ID 22 did not significantly reduce binding to human fH. As shown in FIG. 28, the R41S, Q38A, and A235G mutants retained binding to MAb JAR31 (panel B), and to MAb JAR 35 (panel C), indicating that the JAR31 and JAR35 epitopes are preserved in each of the R41S, Q38A, and A235G mutants.

As shown in FIG. 29, panel A, the Q126A, D201A, and E202A single substitutions in fHbp ID 22 did not significantly reduce binding to human fH. As shown in FIG. 29, panel B, the Q126A, D201A, and E202A mutants retained binding to MAb JAR35, which indicated that the JAR35 epitope is preserved in each of these mutants.

The effect of various single and double amino acid substitutions on the ability of fHbp ID 1, ID 22, and ID 77 to bind to human fH, and to bind to various monoclonal antibodies, is summarized in Tables 6 and 7.

TABLE 6

Mutations that decrease fH binding

| Background fHbp Sequence Variant (modular group*) | Amino Acid Mutation | Fold-Decrease in fH binding (FIG. Number) | Anti-fHbp MAb Reactivity¶ | | | |
|---|---|---|---|---|---|---|
| | | | JAR5 | JAR4 | JAR31 | JAR35 |
| ID 1 (I) | None (WT) | 0 | 2 | 2 | 0 | 0 |
| | R41S | >50 (F10) | 2 | 2 | NA | NA |
| | R41A | >50 (F10) | 2 | Not Done | NA | NA |
| | R130A | >50 (F15) | 2 | 1 | NA | NA |
| | H119A | >10 (F15) | 2 | 1 | NA | NA |
| | E218A | >50† (F4) | 2 | 2 | NA | NA |
| | E239A | >10† (F4) | 2 | 2 | NA | NA |
| | E218A/E239A | >50† (F4) | 2 | 2 | NA | NA |
| ID 4 (I) | R41S | >50 (F11) | 2 | 2 | NA | NA |
| ID 9 (I) | R41S | >50 (F11) | 2 | 2 | NA | NA |
| ID 74 (I) | R41S | >50 (F11) | 2 | 2 | NA | NA |
| ID 15 (IV) | None (WT) | 0 | 2 | 0 | 0 | 0 |
| | S41P | >50 (F17) | 2 | NA | 0 | NA |
| ID 22 (III) | None (WT) | 0 | 0 | 2† | 2 | 2 |
| | R80A | >50 (F23) | NA | 0 | 2 | 2 |
| | D211A | >50 (F23) | NA | 2 | 2 | 2 |
| | E218A | >50 (F23) | NA | 2 | 2 | 2 |
| | E248A | >50 (F23) | NA | 1 | 2 | 2 |
| | G236I | >50 (F27) | NA | 0 | 1 | 2 |
| | T220A/H222A | >50 (F27) | NA | 2 | 2 | 2 |

TABLE 6-continued

Mutations that decrease fH binding

| Background fHbp Sequence Variant (modular group*) | Amino Acid Mutation | Fold-Decrease in fH binding (FIG. Number) | Anti-fHbp MAb Reactivity¶ | | | |
|---|---|---|---|---|---|---|
| | | | JAR5 | JAR4 | JAR31 | JAR35 |
| ID 77 (VI) | None (WT) | 0 | 0 | 2† | 2 | 0 |
| | R41S/K113A | >10 (F21) | NA | 1 | 2 | NA |
| | R41S/K119A | >5 (F21) | NA | 1 | 2 | NA |
| | R41S/D121A | >10 (F21) | NA | 1 | 2 | NA |
| | R41S/K113A/D121A | >50 (F22) | NA | 0 | 2 | NA |

*Modular group based on lineages of five variable segments, see FIG. 16. Modular group I and IV are in the antigenic variant 1 group; modular groups III and VI are in antigenic variant group 2.
¶Compared with binding of mAb to respective wildtype sequence variant; 0, no significant binding by MAb; 1, diminished binding (>30% decrease), 2, similar or higher binding (<30% decrease).
‡JAR 4 binds about 30% less to variant 2 fHbp (i.e., ID 22 or 77) than to variant 1 (i.e., ID 1)
†FIG. 5 of U.S. Patent Publication No. 2006/0029621
**NA, not applicable; for mAb reactivity, the antibody does not bind to respective wildtype sequence variant

TABLE 7

Mutations that do not significantly decrease fH binding

| Background fHbp Sequence Variant (Modular Group*) | Amino Acid Mutation | Fold-Decrease in fH binding* (FIG. No.) | Anti-fHbp MAbs | | | |
|---|---|---|---|---|---|---|
| | | | JAR5 | JAR4 | JAR31 | JAR35 |
| ID 1 (I) | None (wildtype) | 0 | 2 | 2 | 0 | 0 |
| | K241E | 0 (F14) | 2 | 2 | NA | NA |
| | Q87A | 0 | 2 | 2 | NA | NA |
| | Q113A | 0 | 2 | 2 | NA | NA |
| | I114A/S117A | 0 | 2 | 2 | NA | NA |
| | G121R | 0 | 2 | 2 | NA | NA |
| ID 15 (IV) | None (Wildtype) | 0 | 2 | 0 | 0 | 0 |
| | E241K | 0 (F14) | 2 | NA | NA | NA |
| ID 19 (VI) | None (wildtype) | 0 | 0 | 2 | | |
| | R41S | 0 (F12) | NA | 1 | 2 | NA |
| ID 22 (III) | Q38A | 0 (F28) | NA | 1 | 2 | 2 |
| | R41S | 0 (F28) | NA | 1 | 2 | 2 |
| | A235G | 0 (F28) | NA | 1 | 2 | 2 |
| | Q126A | 0 (F29) | NA | 2 | 2 | 2 |
| | D201A | 0 (F29) | NA | 1 | 1 | 2 |
| | E202A | 0 (F29) | NA | 1 | 2 | 2 |
| ID 77 (VI) | R41S | 0 (F12) | NA | ND*** | 2 | NA |
| | K113A | 0 (F20) | NA | ND | 2 | NA |
| | K119A | 0 (F20) | NA | ND | 2 | NA |
| | D121A | 0 (F20) | NA | ND | 2 | NA |

*Modular group based on lineages of five variable segments, see FIG. 16. Modular group I and IV are in the antigenic variant 1 group; modular groups III and VI are in antigenic variant group 2.
*Compared with fH binding by respective wildtype fHbp variant.
¶Compared with binding to respective wildtype sequence variant; 0, no significant binding by mAb; 1, diminished binding (>30% decrease), 2, similar or higher binding (<30% decrease)
**NA, not applicable; mAb does not bind to respective wildtype sequence variant
***ND, not tested As shown in FIG. 30, panel A, the E218A single substitutions in fHbp ID 28 reduced binding to human fH compared with binding of fH by wildtype fHbp ID 28. Also as shown in FIG. 30, panel A, the E197A, K245A, and D201A single substitutions in fHbp ID 28 did not significantly reduce binding to fH. FIG. 30, panel B shows binding of mouse polyclonal anti-fHbp ID28 antiserum to the various proteins (WT fHbp; and E197A, K245A, and D201A single substitutions in fHbp ID 28). The data presented in FIG. 30, panel B indicate that the various fHpb are present on the ELISA plate in similar quantities. As shown in FIG. 30, panels C and D, the E218A mutant bound to JAR 31 and JAR 33 MAbs, indicating that the overall conformations of the epitopes recognized by these MAbs are retained.

The overall immunogenicity of the fHbp mutants can be determined by administering the mutants as vaccines to wildtype mice whose native fH does not bind to the mutant or wildtype vaccines. The data generated in this model provide an overall assessment of whether or not the epitopes important in eliciting serum bactericidal antibodies are retained in the mutant vaccine. For example, the E218A/E239A mutant in fHbp ID 1 eliminated binding with human fH but in multiple studies had impaired ability to elicit bactericidal antibody responses in WT mice (Table 2, above). The immunogenicity experiments are carried out as described above in Example 1. The titers of IgG and bactericidal antibodies are measured and compared to the corresponding levels found in mice administered with the corresponding wild-type and/or negative controls. If the critical epitopes needed for eliciting bactericidal activity are retained by the mutant vaccine, the expectation is that the levels of antibody elicited in the wildtype mice will not be significantly different than the levels elicited by the corresponding wild-type fHbp vaccine.

Example 15. Induction of Bactericidal Response by fHbp Variants

Wildtype BALB/c mice (whose fH does not bind to the WT fHbp) were immunized intraperitoneally with three doses of recombinant fHbp vaccines, with each dose separated by three-week intervals. Each dose contained 10 µg of recombinant fHbp and 300 µg Al(OH)$_3$ in a volume of 100 µl (final buffer composition was 10 mM Histidine, 150 mM NaCl, pH 6.5). Blood samples were obtained by cardiac puncture three weeks after the third dose.

Serum bactericidal titers were measured against group B strain H44/76 (ID 1) or group W-135 strain Ghana 04/07 (ID 22) using IgG depleted human complement (Beernink et al, J Immunology 2011). Not Different, geometric mean titers (GMTs) between mutant and respective WT vaccine were not significantly different (P>0.10 by T test on log 10 transformed titers).

The data are shown in FIGS. 31-33. FIG. 31 shows serum bactericidal titers of mice immunized with mutants of fHbp ID 1 vaccines with decreased binding with human fH. Each symbol represents the titer of an individual mouse measured against group B strain H44/76 (ID 1). Horizontal lines represent geometric mean titers. The respective GMTs of each of the mutant vaccines were not significantly different than that elicited by the WT fHbp ID 1 vaccine (P>0.10).

FIG. 32 shows serum bactericidal titers of mice immunized with mutant fHbp ID 22 vaccines with decreased binding with human fH. Each symbol represents the bactericidal titer of an individual mouse measured against group W-135 strain Ghana 7/04 (ID 22). Horizontal lines represent geometric mean titers. Upper panel. Mutant vaccines (D211A, E218A, E248A and T221A/H223A) with GMTs that were not significantly different than that of WT ID 22 vaccine (P>0.10). Lower panel, Mutant vaccines (R80A and G236I) that elicited significantly lower GMTs than that of WT ID 22 vaccine (P<0.05).

FIG. 33 shows serum bactericidal titers of mice immunized with mutant fHbp ID 77 vaccine with decreased binding with human fH. Each symbol represents the bactericidal titer of an individual mouse measured against group W-135 strain Ghana 7/04 (ID 22). Horizontal lines represent geometric mean titers. Mice immunized with the triple R41S/K113A/D121A mutant ID 77 vaccine had a significantly lower GMT than mice immunized with WT vaccine (P<0.05).

Table 8 summarizes the immunogenicity data shown in FIGS. 31-33. Not Different, geometric mean titers (GMTs) between mutant and respective WT vaccine were not significantly different (P>0.10 by T test on log 10 transformed titers).

TABLE 8

Immunogenicity of fHbp mutants with decreased fH binding

| | | Bactericidal Activity | | |
|---|---|---|---|---|
| fHbp ID | fHbp Vaccine | No of Mice | Strain | Titers vs. Respective WT |
| 1 | WT | 14 | H44/76 | n/a |
| 1 | R41S | 14 | H44/76 | Not Different |
| 1 | R41A | 14 | H44/76 | Not Different |
| 1 | R130A | 12 | H44/76 | Not Different |
| 1 | E239A | 12 | H44/76 | Not Different |
| 22 | WT | 10 | Ghana 04/07 | n/a |
| 22 | D211A | 10 | Ghana 04/07 | Not Different |
| 22 | E218A | 10 | Ghana 04/07 | Not Different |
| 22 | E248A | 10 | Ghana 04/07 | Not Different |
| 22 | T221A/H223A | 10 | Ghana 04/07 | Not Different |
| 22 | R80A | 10 | Ghana 04/07 | Lower |
| 22 | G236I | 10 | Ghana 04/07 | Lower |
| 77 | WT | 12 | Ghana 04/07 | n/a |
| 77 | R41S/K113A/D121A | 12 | Ghana 04/07 | Lower |

Example 16. Sequence Alignments

FIGS. 34 and 35 present an amino acid sequence alignments of fHbp ID 1 (SEQ ID NO:1), fHbp ID 22 (SEQ ID NO:2), fHbp ID 77 (SEQ ID NO:4), fHbp ID 28 (SEQ ID NO:3), and ID1/ID77 chimera (SEQ ID NO:8) amino acid sequences. ID 28 is shown as a reference sequence for fHbp variant group 3. Factor H binding interface residues (highlighted in gray) are as described in Schneider et al. ((2009) *Nature* 458:890-3) described as hydrogen bond or ionic interactions. GEHT (SEQ ID NO:27) at position 136 to 139 represents the junction point between ID 1 and ID 77 for the chimeric fHbp.

FIG. 35. Alignment of fHbp ID 1 (SEQ ID NO:1), fHbp ID 22 (SEQ ID NO:2), fHbp ID 77 (SEQ ID NO:4), fHbp ID 28 (SEQ ID NO:3), and ID1/ID77 chimera (SEQ ID NO:8) amino acid sequences. Residues highlighted in gray indicate residues mutated and summarized in Table 7.

Table 9, below, summarizes MAb reactivity of fHbp ID 1, ID 22, ID 77, and ID 28.

TABLE 9

| ID | Variant | Modular Group | MAb Reactivity |
|---|---|---|---|
| 1 | 1 | I | JAR 4, JAR 5 |
| 22 | 2 | III | JAR 4, JAR 31, JAR 35 |
| 77 | 2 | VI | JAR 4, JAR 31, JAR 35 |
| 28 | 3 | II | JAR 31, JAR 33 |

Example 17. Efficacy of Inhibition of fH/fHbp Binding Correlates with Bactericidal Activity; and the Role of NspA Materials and Methods Murine Anti-fHbp mAbs.

The hybridoma cell lines producing murine fHbp-specific monoclonal antibodies (mAbs) JAR 3 (IgG3), JAR 5 (IgG2b) and mAb502 (IgG2a; Giuliani et al. (2005) *Infect. Immun.* 73:1151; and Scarselli et al. (2009) *J. Mol. Biol.* 386:97) were used. Control mAbs included SEAM 12 (Granoff et al. (1998) *J. Immunol.* 160:5028), which reacts with the group B capsule, and an anti-PorA P1.7 (NIBSC code 01/514, obtained from the National Institute for Biological Standards and Control, Potters Bar, United Kingdom).

Human IgG1 Chimeric Mouse Anti-fHbp mAbs.

RNA isolated from the hybridoma cells was converted into cDNA using an Omniscript RT Kit (Qiagen), according to the manufacturer's instructions. cDNA was amplified using immunoglobulin heavy (H) and light (L) chain-specific primers (Wang et al. (2000) *Infect. Immun.* 68:1871) and inserted into the pGem vector (Promega) for sequencing. Based on the determined sequences, specific primers were designed to facilitate the insertion of the murine VH and VL sequences into a modified FRT bicistronic eukaryotic expression vector (Invitrogen). For each antibody, the murine VL sequence was inserted downstream of a human kappa L chain leader sequence, and in frame with a human kappa L chain constant sequence. The murine VH sequence was inserted downstream from a human H chain leader sequence, and in frame with a complete human IgG1 constant region sequence. The vector utilized an Internal Ribosomal Entry Segment (IRES) sequence between the VH and VL sequences to facilitate balanced translation of both chains. The DNA sequences of all constructs were verified prior to transfection.

Flp-In CHO cells (Invitrogen) were plated at $3.5 \times 10^5$ cells per well (in 2 mL Flp-In medium) in Nunclon Delta 6-well plates and then incubated at 37° C., 5% $CO_2$ overnight. Once cells reached 80% confluence they were transfected with pOG44 and the FRT vector containing the VH and VL inserts (9:1 ratio) using the TransFast transfection reagent (Promega). Forty-eight hours after transfection, the cells were trypsinized and placed in a fresh 6-well plate under drug selection with 600 μg/ml hygromycin. Transfected cells were adapted to serum-free suspension culture using Excell 302 medium (Sigma Aldrich), and grown for approximately 2 weeks. Antibody from the cell culture supernatant was concentrated prior to purification using a 200 ml stirred cell (Amicon) and applying nitrogen gas pressure. Antibody was purified using HiTrap protein G columns (GE Healthcare) followed by extensive dialysis against PBS. BSA was added to a final concentration of 1% and aliquots were stored to −30° C.

ELISA.

Concentrations of the human IgG1-mouse chimeric mAbs were determined by a capture ELISA with goat anti-human κ chain specific antibody (Biosource) bound to wells of a microtiter plate. Bound human IgG was detected by goat anti-human IgG antibody conjugated with alkaline phosphatase (Invitrogen). Antibody concentrations were assigned by comparison with concentration-dependent binding of a human IgG1 standard (monoclonal κ chain antibody from human myeloma, Sigma). Binding of the anti-fHbp mAbs to fHbp was measured by ELISA with recombinant fHbp on the plate. The secondary detecting antibody was goat anti-human κ chain specific antibody conjugated with alkaline phosphatase (Biosource).

Surface Plasmon Resonance.

The kinetics of binding of the human-mouse chimeric mAbs to fHbp was measured by surface plasmon resonance with immobilized recombinant fHbp (500 or 1000 response units) on CM5 chips (GE Healthcare, Piscataway, N.J.), which was performed via amine coupling (Amine Coupling kit, GE Healthcare). Kinetics of binding were determined at mAb concentrations ranging from 0.016 to 50 μg/ml (0.1 μM to 333 μM) using a Biacore T/100 instrument (GE Healthcare, Piscataway, N.J.).

Binding to *N. meningitidis* by Flow Cytometry.

Binding of the chimeric mAbs to the surface of live encapsulated bacteria was measured with strain H44/76 (B:15:P1.7,16; ST -32), which is a relatively high expresser of fHbp ID 1 (Welsch et al. (2008) *J. Infect. Dis.* 197:1053; Welsch et al. (2004) *J. Immunol.* 172:5606). In some experiments, isogenic knockout (KO) mutants of H44/76 in which fHbp, NspA or both proteins were not expressed, were tested. The respective genotypes were fHbp:Erm, NspA: Spc, and fHbp:Erm/NspA:Spc (Lewis et al. (2010) *PLoS Pathog.* 6:e1001027). The binding assay was performed as previously described except that test or control antibodies were incubated together with the cells for 1 hr at room temperature instead of 2 hrs on ice. Antibody bound to the bacteria was detected by CF488A goat anti-human IgG (BioTium).

Inhibition of Binding of fH.

The ability of the anti-fHbp mAbs to inhibit binding of fH to fHbp was measured by ELISA. Wells of a microtiter plate were coated with recombinant fHbp (2 μg/ml). Dilutions of the mAbs were added and incubated at 37° C. for 2 hrs, followed by human fH (Complement Tech.), 2 μg/ml, which was incubated for an additional 1 hour at room temperature. After washing with PBS-0.05% Tween 20, bound fH was detected by a sheep polyclonal antiserum to fH (Abcam) followed by donkey anti-sheep IgG antibody (Sigma Aldrich) conjugated with alkaline phosphatase. The results were expressed as the percentage of inhibition of fH binding in the presence of an anti-fHbp mAb compared with fH binding in the absence of the mAb.

The ability of the anti-fHbp mAbs to inhibit binding of fH to the surface of live bacterial cells was measured by flow cytometry. H44/76 bacteria were incubated with 50 μg/ml of anti-fHbp mAb and different concentrations of purified fH for 30 mins at room temperature. After washing the cells, bound fH was detected by a sheep polyclonal antiserum to fH (Lifespan Bioscience) followed by donkey anti-sheep IgG antibody (Invitrogen) conjugated with green-fluorescent Alexa Fluor 488 dye. In some experiments 20% IgG-depleted human serum, which contained 90 μg/ml of fH, was used as the source of human fH. To avoid bacteriolysis, the human serum was heated for 30 mins at 56° C. to inactivate heat-labile complement components essential for bacteriolysis. This heat treatment did not affect fH activity.

Human Complement Sources.

The primary complement source for measurement of bactericidal activity and C4b deposition was serum from a healthy adult with normal total hemolytic complement activity and no detectable serum bactericidal antibodies against the test strain. To eliminate non-bactericidal IgG antibodies, which might augment or inhibit the activity of the test mAbs, the complement source was depleted of IgG using a protein G column (HiTrap Protein G, GE Life Sciences, Piscataway, N.J.). A 1-ml aliquot of human serum was passed over a protein G column (1 ml HiTrap Protein G, GE Life Sciences, Piscataway, N.J.) equilibrated with PBS and the flow-through fraction was collected. Adequacy of IgG depletion was monitored by an IgG capture ELISA, and CH50 activity was assayed with a commercial assay (EZ Complement CH50 test kit, Diamedix Corp., Miami, Fla.). To avoid bacteriolysis when measuring C4b deposition, the complement source was depleted of C6 using an anti-human complement C6 affinity column, as previously described (Plested and Granoff (2008) *Clin. Vaccine Immunol.* 15:799). In some experiments, commercial human complement sources that had been depleted of fH or C1q (Complement Tech.), which was also depleted of IgG as described above, were used.

Serum Bactericidal Assay.

Bactericidal activity was measured as previously described (Beernink et al. (2009) *J. Infect. Dis.* 199:1360) using log-phase bacteria of group B strain H44/76 and 20% human serum depleted of IgG as a complement source. Immediately before performing the assay, the anti-fHbp mAbs were centrifuged for two hours at 100,000×g to remove aggregates. Bactericidal activity ($BC_{50\%}$) was defined by the mAb concentration that resulted in a 50% decrease in CFU/ml after 60-min incubation in the reaction mixture compared with the CFU/ml in negative control wells at time zero.

C1q-Dependent, C4b Deposition on *N. meningitidis*.

Flow cytometry was used to measure deposition of human C4b on the surface of live bacteria of group B strain H44/76. The bacteria were grown as described above for the bactericidal assay and were incubated with 5% C1q-depleted human serum (Complement Tech.) that had also been depleted of complement C6 to avoid bacteriolysis (See above). Different concentrations of the chimeric human-mouse anti-fHbp mAbs were added with or without 20 µg/ml of purified C1q protein (Complement Tech.). Human C4b bound to bacteria was detected with fluorescence isothiocyanate-conjugated anti-human C4b (Meridian Life Science).

Results

JAR 3 and JAR 5 mAbs inhibit binding of each other to fHbp, and recognize overlapping epitopes that involve glysine and lysine at positions 121 and 122, respectively. The respective epitopes recognized by the two paratopes were differentiated by dissimilar binding by Western blot with different fHbp amino acid sequence variants. The murine hybridomas JAR 3 and JAR 5 were derived from the same VH and VL germline genes, but differed in sequence in their respective CDR regions (with the exception of VL CDR2). The murine mAb502 was encoded by different VH and VL germline genes than those of JAR 3 or JAR 5. mAb502 recognizes a conformational epitope requiring an arginine at position 204, and does not inhibit binding of JAR 3 or JAR 5 to fHbp. Thus, mAb502 recognizes an fHbp epitope distinct from those recognized by the JAR mAbs. The Genbank accession numbers for vL and vH genes of mAb502 are EU835941 and EU835942, respectively. The GenBank accession numbers for VL and VH regions of JAR3 and JAR5 antibodies are as follows: JF715928, JAR3 variable heavy chain; JF715929, JAR3 variable light chain; JF715926, JAR5 variable heavy chain; and JF715927, JAR5 variable light chain.

FIG. 36. Model of fHbp in a complex with a fragment of fH, based on the coordinates of the crystal structure (Schneider et al. (2009) *Nature* 458:890). Spatial relationship of the amino acid residues previously reported to affect binding of anti-fHbp mAb502, and JAR 3 and JAR 5 to fHbp fH fragment, light gray, is shown in complex with fHbp.

The Three Human IgG1 Mouse Chimeric Anti fHbp mAbs have Similar Binding Characteristics.

Three human-mouse chimeric anti-fHbp antibodies were constructed, in which each of the JAR 3, JAR 5 and mAb502 paratopes were paired with a human IgG1 constant region. In an ELISA with recombinant fHbp adsorbed to the wells of a microtiter plate, the three mAbs showed similar respective binding (FIG. 37, Panel A). By surface plasmon resonance, the respective kinetics of binding with 200, 500 or 1000 RU of immobilized fHbp were similar for the three mAbs, which were each tested at concentrations from 0.016 to 2.25 µg/ml. Representative data for 0.25 µg/ml (1.7 µM) of mAb and 1000 RU of immobilized fHbp ID 1 are shown in Panel B. Although mAb502 showed lower peak binding to fHbp than JAR 3 or JAR 5, the respective association rates, $K_a$, were similar (4.25E+06, 2.26E+06 and 1.19E+06, for JAR 3, JAR 5 and mAb 502, respectively). The dissociation rates were slow for all three mAbs, which precluded calculation of accurate dissociation constants. The order of magnitude of the $K_d$ values for each of the mAbs was E -05.

mAb binding to the surface of live bacteria of group B strain H44/76 was measured by indirect fluorescence flow cytometry. At mAb concentrations between 0.8 and 40 µg/ml, the respective binding of the three mAbs was indistinguishable from each other. The binding results obtained with 4 µg/ml are shown in FIG. 37, Panel C. Binding was not affected by the presence of heat-inactivated 20% IgG-depleted human serum, which contained ~90 µg/ml of human fH (Compare FIG. 37, Panel D with FIG. 37, Panel C).

FIGS. 37-D. Binding of fHbp-specific mAbs to fHbp. A. ELISA. Bound IgG was detected with an anti-human kappa light chain-specific alkaline phosphatase conjugated antibody. B. Surface plasmon resonance. Binding of anti-fHbp mAbs (0.25 µg/ml) to immobilized recombinant fHbp (1000 RU). C. Flow cytometry. Binding of anti-fHbp mAbs (4 µg/ml) with live bacterial cells of *N. meningitidis* group B strain H44/76. JAR 3, black dotted line; JAR 5, gray line; mAb502, black line. An irrelevant mAb (100 µg/ml) was a negative control (gray filled histogram). The binding curves of the three anti-fHbp mAbs are superimposed. D. Flow cytometry. Same mAb concentrations as in Panel C with the addition of 20% IgG-depleted human serum as a source of human fH (~90 µg/ml).

All Three Human-Mouse Chimeric mAbs Activate the Human Classical Complement Pathway but Only JAR 3 and JAR 5 have Bactericidal Activity.

Activation of the classical complement pathway is initiated when IgG binds to the bacterial surface and there is sufficient antigen-antibody complex to allow proximate Fc regions of the antibody to engage C1q, which in turn activates C4b. C4b binding to the surface of live *N. meningitidis* cells of group B strain H44/76 was measured as a surrogate for C1q binding and C4b activation, and as a marker for classical complement pathway activation.

When the source of complement was 5% C1q-depleted human serum that had also been depleted of IgG, there was negligible C4b deposition elicited by the anti-fHbp mAbs (FIG. 38, Panel A). When 20 µg/ml of purified C1q was added back to the reaction mixture, each of the mAbs activated C4b deposition (FIG. 38, Panel B). Although binding of each of the mAbs activated the classical complement pathway only JAR 3 and JAR 5 had complement-mediated bactericidal activity (FIG. 38, Panel C). The mean concentrations±SE for 50% killing in three assays were 9±0.85 µg/ml for JAR 3; 15±2 µg/ml for JAR 5 (P=0.024), and >100 µg/ml for mAb502 (P<0.0003 compared to JAR 3 or JAR 5).

FIGS. 38A-C. C1q-dependent complement activation on encapsulated group B bacteria of strain H44/76. A. Flow cytometry. Activation of C4b deposition by 4 µg/ml of mAb and complement (5% IgG-depleted human serum) that had been depleted of C1q. Anti-fHbp mAb JAR 3, black dotted line; JAR 5, gray line; mAb502, black line, and an irrelevant human mAb (100 µg/ml; gray filled histogram) (data for each are superimposed). B. Flow cytometry. Same symbols and conditions as in Panel A except for the addition of 20 µg/ml of purified C1q protein to the reactions. C. Bactericidal activity. Survival of bacteria after incubation for 60 min at 37° C. with each of the mAbs and complement (20% IgG-depleted human serum).

Chimeric mAbs JAR 3 and JAR 5, but not mAb502, Inhibit Binding of fH.

In previous studies, murine mAbs JAR 3 and JAR 5 inhibited binding of fH to fHbp whereas murine mAb502 did not inhibit fH binding. By ELISA, the human IgG1 chimeric JAR 3 and JAR 5 mAbs also inhibited binding of fH to fHbp while the chimeric mAb502 did not inhibit fH binding (FIG. 39, Panel A). When 20% heat-inactivated IgG-depleted human serum was the source of fH, 50 µg/ml of chimeric JAR 3 or JAR 5, but not mAb502, inhibited binding of fH to the surface of live bacterial cells (FIG. 39, Panel B). As little as 2 µg/ml of JAR 3 or JAR 5 also inhibited binding of fH (Panel C) although inhibition was less complete than with 50 µg/ml of the mAb (Panel B).

FIGS. 39A-C. Inhibition of fH binding by anti-fHbp mAbs. A. ELISA: fH (4 µg/ml) with solid-phase recombinant fHbp. B and C. Flow cytometry, with live bacterial cells of group B strain H44/76; Light gray filled area, bacteria with fH (~90 µg/ml) in 20% IgG-depleted human serum without a mAb; black solid line, bacteria with serum fH+mAb502, 50 µg/ml; dotted black line, bacteria with serum fH+JAR 3, 50 µg/ml; gray solid line, bacteria with serum fH+JAR 5, 50 µg/ml; dark gray filled area, bacteria without fH or mAb as a negative control. fH binding was detected with an fH-specific sheep antibody. C. Same conditions as in Panel B except that 2 µg/ml of each of the anti-fHbp mAbs was tested instead of 50 µg/ml.

The correlation observed between bactericidal activity and mAb inhibition of fH binding does not necessarily prove that inhibition was responsible for the greater bactericidal activity of JAR 3 or JAR 5 than mAb502. For example, the spatial relationships of fHbp epitopes on the surface of the bacteria that are recognized by anti-fHbp mAbs that inhibited fH binding are different than those of epitopes recognized by anti-fHbp mAbs that did not inhibit fH binding (compare, for example, the positions of the amino acid residues previously reported to affect binding of mAb502 (Scarselli et al. (2009) *J Mol Biol* 386:97-108) with those of JAR 3 and JAR 5 (Beernink et al. (2008) *Infect Immun* 76:4232-4240)(FIG. 36). These spatial differences could potentially affect the formation of a functional membrane attack complex independent of fH down-regulation.

To determine whether the differences in the locations of the respective epitopes affected bactericidal activity independent of fH inhibition, anti-fHbp bactericidal activity was measured with fH-depleted complement (20% human serum that also had been depleted of IgG). In the absence of fH, all three mAbs showed similar complement-mediated bactericidal activity ($BC_{50\%}$, 1.2 to 1.4 µg/ml, Table 10). In contrast, when purified human fH was added to the reaction mixture, mAb502 was no longer bactericidal ($BC_{50\%}$>100 µg/ml, Panel B). Adding fH to the reaction mixture also decreased bactericidal activity of two control murine mAbs reactive with the group B capsule or PorA (compare respective $BC_{50\%}$ values measured with fH depleted complement, Panel C, with those with fH-repleted complement, Panel C) but the effect of fH repletion was less pronounced than with the anti-fHbp mAbs.

TABLE 10

Anti-fHbp mAb bactericidal activity measured with fH-depleted human complement

| | Bactericidal Activity ($BC_{50\%}$, µg/ml)* | | | |
|---|---|---|---|---|
| | fH-depleted Complement | | fH-repleted Complement | |
| | Mean | Range | Mean | Range |
| Human IgG1 chimeric mouse anti-fHbp mAbs | | | | |
| JAR 3 | 1.4 | 0.8-2.0 | 15.2 | 12.5-18 |
| JAR 5 | 1.25 | 1.0-1.5 | 23.5 | 22-25 |
| mAb502 | 1.25 | 0.75-1.5 | >100 | >100 |
| Control mouse IgG2a mAbs | | | | |
| Anti-PorA P1.7 | 0.5 | 0.3-0.7 | 1.05 | 1.0-1.1 |
| Anti-capsular, SEAM 12 | 0.18 | 0.15-0.2 | 1.15 | 1.0-1.2 |

*Data are mean and respective ranges of the concentrations of the mAbs that gave 50% killing after 1 hr incubation with complement ($BC_{50\%}$) in two independent assays. For fH repleted complement, 50 µg/ml of fH was added.

Elimination of fH Binding to NspA Enhances Bactericidal Activity of Anti-fHbp mAbs JAR 3 and JAR 5, but not mAb502.

The much lower concentrations of anti-fHbp mAbs required for bacteriolyis with fH-depleted than fH-repleted complement suggested that when fH was present, inhibition of fH binding by JAR 3 or JAR 5 was incomplete (for example, because of binding of fH by a second meningococcal ligand such as NspA (Lewis et al. (2010) *PLoS Pathog.* 6:e1001027). To investigate binding of fH independent of binding to the fHbp ligand, fH binding was measured with an isogenic mutant of group B strain H44/76 in which the gene encoding fHbp had been inactivated (fHbp KO strain). A second mutant in which both the fHbp and NspA genes had been inactivated served as a control for a possible contributory effect of NspA.

By flow cytometry, the two mutants and the parent strain showed similar respective binding with a control murine anti-PorA P1.7 mAb (FIG. 40, Panel A). As expected, there was much less binding of fH (100 µg/ml) with the fHbp KO mutant than with the WT strain (compare black line with gray line in FIG. 40, Panel B). In the absence of both fHbp and NspA expression (dashed line), fH binding was indistinguishable from the negative control WT bacteria without added fH (light gray filled histogram). Similar respective results were obtained when 20% IgG-depleted human serum was used as the source of fH (FIG. 40, Panel C).

FIGS. 40A-C. Binding of fH to mutants of group B H44/76 with genetic inactivation of fHbp expression or expression of both fHbp and NspA. A. Anti-PorA mAb (P1.7, 20 µg/ml). Black line, WT; gray line, fHbp KO; dashed line, fHbp KO combined with NspA KO. B. Binding of purified human fH (100 µg/ml). Designation as in panel A. C. Binding of fH in human serum (20%, IgG-depleted). Designation as in Panel A. Results were replicated in two independent assays.

To determine a possible contribution of fH binding to NspA (and corresponding down-regulation of complement activation) to the high anti-fHbp mAb concentrations required for bacteriolysis in the presence of fH, anti-fHbp bactericidal activity was measured with an isogenic NspA KO mutant (FIG. 41). With chimeric JAR 3 or JAR 5, which inhibited binding of fH to fHbp, there was significantly greater killing of the NspA KO mutant than the control WT strain (FIG. 41, Panels A and B, respectively). In contrast, chimeric mAb502, which did not inhibit fH binding, had no bactericidal activity against either strain (FIG. 41, Panel C). Two control mouse mAbs, anti-PorA and anti-capsular, showed similar respective bactericidal activity against the WT and mutant NspA KO strains (FIG. 41, Panels D and E, respectively).

FIGS. 41A-E. Bactericidal activity of anti-fHbp mAbs measured against a mutant of group B H44/76 with genetic inactivation of NspA expression. Survival of bacteria after incubation for 60 min at 37° C. with each of the mAbs and 20% IgG-depleted human serum as a complement source. Open triangles, NspA KO mutant; closed triangles, control WT strain. A. Chimeric JAR 3. B. Chimeric JAR 5. C. Chimeric mAb502. D. Control murine anti-Por A mAb (P 1.7). E. Control murine mAb, SEAM 12, reactive with group B capsule. Results are from three independent dilutions of the mAbs performed in two experiments. Where indicated, respective survival for WT and NspA KO strains incubated at mAb dilution was significantly different (*$P \leq 0.02$; **$P<0.001$).

Importance of Binding fH by fHbp on Anti-NspA mAb Bactericidal Activity.

As noted above, using a NspA KO mutant of group B strain H44/76, the data showed that in the absence of fH bound to NspA, anti-fHbp mAbs that inhibited fH binding (JAR 3 or JAR 5) had greater bactericidal activity than when tested against a wildtype strain with NspA expression. The reverse experiment was also conducted: an anti-NspA mAb AL12 (Moe et al, *Infect. Immun.* (2002) 70:6021) was tested against a fHbp knockout mutant of a group A strain (Senegal 1/99). As shown in FIG. 42, the fHbp KO mutant was 50-fold more susceptible to killing by the anti-NspA mAb than the WT strain. In contrast, there was no significant enhanced susceptibility of the fHbp KO mutant to killing by a control mAb to PorA P1.9. Bactericidal activity of the mAbs was measured with human complement (IgG-depleted human serum).

Further Data that Inhibition of fH by Anti fHbp Antibodies is Important for Bactericidal Activity.

Eight of nine African meningococcal isolates tested were susceptible to bactericidal activity of an antiserum from mice immunized with a prototype native outer membrane vesicle (NOMV) vaccine prepared from a mutant of group B strain H44/76 with over-expressed fHbp ID 1 (Table 11). In contrast, all nine isolates were resistant to the antiserum from mice immunized with the recombinant fHbp ID 1 vaccine (bactericidal titers <1:10), and only one of the nine isolates was killed by the control antiserum from mice immunized with the NOMV vaccine from the fHbp KO mutant (X5, titer 1:36). Mixing the NOMV fHbp KO antiserum with the antiserum to the recombinant fHbp ID 1 vaccine did not increase bactericidal activity against any of the test strains (Table 11). Thus, the anti-fHbp antibodies elicited by the NOMV vaccine with over-expressed fHbp appeared to be responsible for the bactericidal activity against the isolates with fHbp sequence variants that did not matched the fHbp ID 1 in the NOMV vaccine. There also was no evidence of cooperative bactericidal activity between antibodies to fHbp and antibodies to other antigens in the NOMV vaccine.

TABLE 11

Bactericidal activity of sera of mice immunized with a native outer membrane vesicle vaccine from group B strain H44/76 with over-expressed fHbp ID 1.

| Test Strain (fHbp ID)* | Recombinant fHbp Vaccine 1/Serum Titer | | NOMV Vaccine 1/Serum Titer | |
|---|---|---|---|---|
| | Homologous fHbp** | fHbp ID 1 | fHbp KO | Over-expressed fHbp ID 1 |
| A3 (ID 5) | <10 | <10 | <10 | 132 |
| A14 (ID 5) | <10 | <10 | <10 | 114 |
| W1 (ID 9) | <10 | <10 | <10 | <10 |
| W3 (ID 9) | 818 | <10 | <10 | 43 |
| X3 (ID 74) | 12204 | <10 | <10 | 574 |
| X5 (ID 74) | 4066 | <10 | 36 | 640 |
| X7 (ID 74) | 7680 | <10 | <10 | 324 |

*Strains A3 and A14 are capsular group A, W1 and W3 are capsular group W-135, and X3, X5 and X7 are capsular group X; All strains were clinical isolates from patients with meningococcal disease from Sub-Saharan Africa
Bactericidal activity (human complement) of stored sera from mice immunized in a previously published study (Koeberling Vaccine 2007, supra) with recombinant fHbp or NOMV vaccines prepared from mutants of group B strain H44/76 with over-expressed of fHbp ID 1. Titers are means of the serum dilution for 50% decrease in CFU/ml after one hr incubation with human complement as measured in at least two independent assays.
**Titer with respective recombinant fHbp vaccine ID 5, 9 or 74 of that of the test strain The Broad Serum Cross-Reactive Anti fHbp Bactericidal Activity Induced by the Mutant NOMV Vaccine is Associated with Higher Anti fHbp Antibody Responses and Greater Blocking of Binding of fH to fHbp than the Recombinant fHbp Vaccine.

By ELISA, the mice immunized with the NOMV vaccine from the mutant with over-expressed fHbp ID 1 had higher serum anti-fHbp ID 1 antibody concentrations than mice immunized with the recombinant fHbp ID 1 vaccine (respective geometric means of 2203 and 746 U/ml, P<0.02, FIG. 43, Panel A). By ELISA, the sera from the mice immunized with the mutant NOMV vaccine also showed greater inhibition of binding of fH to fHbp ID 4, which was the sequence variant expressed by group A strains (FIG. 43, Panel B, P<0.05 at each dilution tested). The increased fH inhibition was not only a result of the higher serum anti-fHbp concentrations in the mutant NOMV vaccine group since on average the anti-fHbp antibody concentration required for inhibition of fH in this group was nearly 4-fold lower than in the recombinant fHbp vaccine ID 1 group (respective geometric means of 1.17 vs. 4.04 U/ml, P<0.05, FIG. 43, Panel C).

FIG. 43, Panel A Anti-fHbp antibody responses to vaccination as measured by ELISA (Panel A), and the ability of serum anti-fHbp antibodies to inhibit binding of fH to fHbp (Panels B and C, also by ELISA). Mice were immunized with recombinant fHbp ID 1 vaccine (filled triangles), or NOMV vaccines prepared from mutants of group B strain H44/76 with over-expressed of fHbp ID 1 (open circles) or a fHbp knock-out (filled circles). For the recombinant fHbp vaccine and the NOMV vaccine with over-expressed fHbp ID 1, each symbol (Panel A and C) represents the result of an individual mouse (10 mice per vaccine group). For the NOMV fHbp KO vaccine, each symbol represents the results of testing pooled sera from 3 to 4 individual animals. A) Anti-fHbp ID 1 antibody concentrations in arbitrary units per ml. NOMV OE vaccine group had higher geometric mean concentration (horizontal line) than mice immunized with the recombinant fHbp vaccine (p=0.02). B) Inhibition of binding of fH to fHbp ID 4, which was heterologous to fHbp ID 1 in the vaccines. At all dilutions, the mean inhibitory activity of the group given the NOMV vaccine from the mutant with over-expressed fHbp (open circles) was higher than the recombinant fHbp vaccine group (filled triangles; p<0.05). C) Serum anti-fHbp ID 1 antibody concentration for 50% inhibition of binding of fH to fHbp ID 4 (96% amino acid identity with ID 1). The geometric mean anti-fHbp antibody concentration for 50% inhibition of fH binding was lower for the NOMV OE fHbp group (open circles) than the recombinant fHbp vaccine group (filled triangles, p<0.05).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A nucleic acid encoding a non-naturally occurring factor H binding protein (fHbp) comprising an amino acid sequence, wherein the amino acid sequence is at least 95% identical to the entire length of the amino acid sequence set forth in SEQ ID NO:1 and comprises the substitution of the arginine at position 41 with serine.

2. The nucleic acid according to claim 1, wherein the non-naturally occurring fHbp differs from the amino acid sequence of SEQ ID NO:1 by 1 to 10 amino acids.

3. A recombinant expression vector comprising the nucleic acid of claim 1.

4. A recombinant expression vector comprising the nucleic acid of claim 2.

5. A genetically modified host cell comprising the nucleic acid of claim 1.

6. A genetically modified host cell comprising the nucleic acid of claim 2.

7. A genetically modified host cell comprising the recombinant expression vector of claim 3.

8. A genetically modified host cell comprising the recombinant expression vector of claim 4.

9. The genetically modified host cell of claim 5, wherein the genetically modified host cell is a mammalian host cell.

10. The genetically modified host cell of claim 5, wherein the genetically modified host cell is *Escherichia coli* (*E. coli*).

11. The genetically modified host cell of claim 5, wherein the genetically modified host cell is a yeast cell.

12. The genetically modified host cell of claim 5, wherein the genetically modified host cell is *Neisseria meningitidis* bacterium.

13. The genetically modified host cell of claim 12, wherein the *Neisseria meningitidis* bacterium comprises a genetic modification that results in decreased or no detectable toxic activity of lipid A.

14. The genetically modified host cell of claim 6, wherein the genetically modified host cell is *Neisseria meningitidis* bacterium.

15. The genetically modified host cell of claim 14, wherein the *Neisseria meningitidis* bacterium comprises a genetic modification that results in decreased or no detectable toxic activity of lipid A.

16. The genetically modified host cell of claim 7, wherein the genetically modified host cell is *Neisseria meningitidis* bacterium.

17. The genetically modified host cell of claim 16, wherein the *Neisseria meningitidis* bacterium comprises a genetic modification that results in decreased or no detectable toxic activity of lipid A.

18. The genetically modified host cell of claim 8, wherein the genetically modified host cell is *Neisseria meningitidis* bacterium.

19. The genetically modified host cell of claim 18, wherein the *Neisseria meningitidis* bacterium comprises a genetic modification that results in decreased or no detectable toxic activity of lipid A.

* * * * *

SEQUENCE LISTING

<160> NUMBER OF SEQ ID NOS: 31

<210> SEQ ID NO 1
<211> LENGTH: 255
<212> TYPE: PRT
<213> ORGANISM: Neisseria meningitidis

<400> SEQUENCE: 1

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 2
<211> LENGTH: 254

```
<212> TYPE: PRT
<213> ORGANISM: Neisseria meningitidis

<400> SEQUENCE: 2

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 3
<211> LENGTH: 262
<212> TYPE: PRT
<213> ORGANISM: Neisseria meningitidis

<400> SEQUENCE: 3

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95
```

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 4
<211> LENGTH: 254
<212> TYPE: PRT
<213> ORGANISM: Neisseria meningitidis

<400> SEQUENCE: 4

Cys Ser Ser Gly Gly Gly Gly Val Ala Ala Asp Ile Gly Ala Arg Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
            245                 250

<210> SEQ ID NO 5
<211> LENGTH: 263
<212> TYPE: PRT
<213> ORGANISM: Neisseria meningitidis

<400> SEQUENCE: 5

Cys Ser Ser Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
            35                  40                  45

Gly Thr Leu Thr Leu Ser Ala Gln Gly Ala Glu Arg Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Thr Ala Asn Gly Ile Arg His
                245                 250                 255

Ile Gly Leu Ala Ala Lys Gln
            260

<210> SEQ ID NO 6
<211> LENGTH: 255
<212> TYPE: PRT
<213> ORGANISM: Neisseria meningitidis

<400> SEQUENCE: 6

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asn Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Arg Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Asp Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Tyr Gly Lys Ile Glu His Leu Lys Ser Pro Glu Leu Asn Val Asp
            180                 185                 190

Leu Ala Ala Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Lys Thr Ala Asn Gly Ile Arg His Ile Gly Leu Ala Ala Lys Gln
                245                 250                 255

<210> SEQ ID NO 7
<211> LENGTH: 255
<212> TYPE: PRT
<213> ORGANISM: Neisseria meningitidis

<400> SEQUENCE: 7

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu

```
                130               135               140
Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
                195                 200                 205

Ser Gly Ser Val Leu Tyr Asn Gln Asp Glu Lys Gly Ser Tyr Ser Leu
            210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 8
<211> LENGTH: 254
<212> TYPE: PRT
<213> ORGANISM: Artificial Sequence
<220> FEATURE:
<223> OTHER INFORMATION: Chimera fHbp ID 1 and ID 77

<400> SEQUENCE: 8

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ala Phe Asn Gln Leu
        130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
            210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
```

-continued

```
                    245                 250

<210> SEQ ID NO 9
<211> LENGTH: 1231
<212> TYPE: PRT
<213> ORGANISM: Homo sapiens

<400> SEQUENCE: 9

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365
```

```
Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
            435                 440                 445

Ser Lys Ser Ser Ile Asp Ile Glu Asn Gly Phe Ile Ser Glu Ser Gln
450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
            515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
                580                 585                 590

Leu Lys Phe Ser Cys Lys Pro Gly Phe Thr Ile Val Gly Pro Asn Ser
            595                 600                 605

Val Gln Cys Tyr His Phe Gly Leu Ser Pro Asp Leu Pro Ile Cys Lys
            610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
                660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
            690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
770                 775                 780

Glu Gly Trp Ile His Thr Val Cys Ile Asn Gly Arg Trp Asp Pro Glu
```

-continued

```
            785                 790                 795                 800
Val Asn Cys Ser Met Ala Gln Ile Gln Leu Cys Pro Pro Pro Gln
                    805                 810                 815

Ile Pro Asn Ser His Asn Met Thr Thr Thr Leu Asn Tyr Arg Asp Gly
                820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
        850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Lys Met
    1010                1015                1020

Asp Gly Ala Ser Asn Val Thr Cys Ile Asn Ser Arg Trp Thr Gly Arg
1025                1030                1035                1040

Pro Thr Cys Arg Asp Thr Ser Cys Val Asn Pro Pro Thr Val Gln Asn
                1045                1050                1055

Ala Tyr Ile Val Ser Arg Gln Met Ser Lys Tyr Pro Ser Gly Glu Arg
            1060                1065                1070

Val Arg Tyr Gln Cys Arg Ser Pro Tyr Glu Met Phe Gly Asp Glu Glu
        1075                1080                1085

Val Met Cys Leu Asn Gly Asn Trp Thr Glu Pro Pro Gln Cys Lys Asp
    1090                1095                1100

Ser Thr Gly Lys Cys Gly Pro Pro Pro Ile Asp Asn Gly Asp Ile
1105                1110                1115                1120

Thr Ser Phe Pro Leu Ser Val Tyr Ala Pro Ala Ser Ser Val Glu Tyr
                1125                1130                1135

Gln Cys Gln Asn Leu Tyr Gln Leu Glu Gly Asn Lys Arg Ile Thr Cys
            1140                1145                1150

Arg Asn Gly Gln Trp Ser Glu Pro Pro Lys Cys Leu His Pro Cys Val
        1155                1160                1165

Ile Ser Arg Glu Ile Met Glu Asn Tyr Asn Ile Ala Leu Arg Trp Thr
    1170                1175                1180

Ala Lys Gln Lys Leu Tyr Ser Arg Thr Gly Glu Ser Val Glu Phe Val
1185                1190                1195                1200

Cys Lys Arg Gly Tyr Arg Leu Ser Ser Arg Ser His Thr Leu Arg Thr
                1205                1210                1215
```

Thr Cys Trp Asp Gly Lys Leu Glu Tyr Pro Thr Cys Ala Lys Arg
            1220                1225                1230

<210> SEQ ID NO 10
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 10

Thr Ala Pro Leu Asp His Lys Asp Lys Gly Leu Gln Ser Leu Thr Leu
1               5                   10                  15

Asp Gln Ser Val Arg Lys Asn Glu Lys Leu Lys Leu Ala Ala Gln Gly
            20                  25                  30

Ala Glu Lys Thr Tyr Gly Asn Gly Asp Ser Leu Asn Thr Gly Lys Leu
        35                  40                  45

Lys Asn
    50

<210> SEQ ID NO 11
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 11

Thr Ala Pro Leu Asp His Lys Asp Lys Ser Leu Gln Ser Leu Thr Leu
1               5                   10                  15

Asp Gln Ser Val Arg Lys Asn Glu Lys Leu Lys Leu Ala Ala Gln Gly
            20                  25                  30

Ala Glu Lys Thr Tyr Gly Asn Gly Asp Ser Leu Asn Thr Gly Lys Leu
        35                  40                  45

Lys Asn
    50

<210> SEQ ID NO 12
<211> LENGTH: 53
<212> TYPE: PRT
<213> ORGANISM: Artificial Sequence
<220> FEATURE:
<223> OTHER INFORMATION: Synthetic polypeptide

<400> SEQUENCE: 12

Thr Ala Pro Leu Asp His Lys Asp Lys Gly Leu Lys Ser Leu Thr Leu
1               5                   10                  15

Glu Asp Ser Ile Ser Gln Asn Gly Thr Leu Thr Leu Ser Ala Gln Gly
            20                  25                  30

Ala Glu Arg Thr Phe Lys Ala Gly Asp Lys Asp Asn Ser Leu Asn Thr
        35                  40                  45

Gly Lys Leu Lys Asn
            50

<210> SEQ ID NO 13
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 13

```
Thr Ala Pro Leu Asp His Lys Asp Lys Gly Leu Lys Ser Leu Thr Leu
1               5                   10                  15

Glu Asp Ser Ile Ser Gln Asn Gly Thr Leu Thr Leu Ser Ala Gln Gly
                20                  25                  30

Ala Glu Lys Thr Tyr Gly Asn Gly Asp Ser Leu Asn Thr Gly Lys Leu
            35                  40                  45

Lys Asn
    50
```

<210> SEQ ID NO 14
<211> LENGTH: 53
<212> TYPE: PRT
<213> ORGANISM: Artificial Sequence
<220> FEATURE:
<223> OTHER INFORMATION: Synthetic polypeptide

<400> SEQUENCE: 14

```
Thr Ala Pro Leu Asp His Lys Asp Lys Gly Leu Lys Ser Leu Thr Leu
1               5                   10                  15

Glu Asp Ser Ile Pro Gln Asn Gly Thr Leu Thr Leu Ser Ala Gln Gly
                20                  25                  30

Ala Glu Lys Thr Phe Lys Ala Gly Asp Lys Asp Asn Ser Leu Asn Thr
            35                  40                  45

Gly Lys Leu Lys Asn
            50
```

<210> SEQ ID NO 15
<211> LENGTH: 174
<212> TYPE: PRT
<213> ORGANISM: Neisseria meningitidis

<400> SEQUENCE: 15

```
Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
                20                  25                  30

His Ala Lys Ala Ser Ser Ser Leu Gly Ser Ala Lys Gly Phe Ser Pro
            35                  40                  45

Arg Ile Ser Ala Gly Tyr Arg Ile Asn Asp Leu Arg Phe Ala Val Asp
    50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Val Gly Val Arg Val Lys Phe
                165                 170
```

<210> SEQ ID NO 16
<211> LENGTH: 19

```
<212> TYPE: PRT
<213> ORGANISM: Artificial Sequence
<220> FEATURE:
<223> OTHER INFORMATION: Synthetic polypeptide

<400> SEQUENCE: 16

Met Asn Arg Thr Ala Phe Cys Cys Leu Ser Leu Thr Thr Ala Leu Ile
1               5                   10                  15

Leu Thr Ala

<210> SEQ ID NO 17
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 17

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val
65

<210> SEQ ID NO 18
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 18

Phe Leu Leu Ala Val
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 19

Gly Ser Gly Gly Ser
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 20

Gly Gly Gly Ser
1

<210> SEQ ID NO 21
<211> LENGTH: 4
```

<212> TYPE: PRT
<213> ORGANISM: Artificial Sequence
<220> FEATURE:
<223> OTHER INFORMATION: Synthetic polypeptide

<400> SEQUENCE: 21

Gly Gly Ser Gly
1

<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 22

Gly Gly Ser Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 23

Gly Ser Gly Ser Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 24

Gly Ser Gly Gly Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 25

Gly Gly Gly Ser Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 26

Gly Ser Ser Ser Gly
1               5

<210> SEQ ID NO 27
<211> LENGTH: 4
<212> TYPE: PRT

<213> ORGANISM: Artificial Sequence
<220> FEATURE:
<223> OTHER INFORMATION: Synthetic polypeptide

<400> SEQUENCE: 27

Gly Glu His Thr
1

<210> SEQ ID NO 28
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 28

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val
65

<210> SEQ ID NO 29
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 29

Val Ala Ala Asp Ile Gly Ala Arg Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val
65

<210> SEQ ID NO 30
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 30

Val Tyr Lys Gln Ser His Ser Ala Leu Thr Ala Phe Gln Thr Glu Gln
1               5                   10                  15

Ile Gln Asp Ser Glu His Ser Gly Lys Met Val Ala Lys Arg Gln Phe
                20                  25                  30

Arg Ile Gly Asp Ile Ala Gly Glu His Thr Ser Phe Asp Lys Leu Pro
            35                  40                  45

Glu Gly Gly Arg Ala Thr Tyr Arg Gly Thr Ala Phe

```
<210> SEQ ID NO 31
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 31

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
            20                  25                  30

Arg Ile Gly Asp Ile Val Gly Glu His Thr Ser Phe Gly Lys Leu Pro
        35                  40                  45

Lys Asp Val Met Ala Thr Tyr Arg Gly Thr Ala Phe
        50                  55                  60
```